US007264959B2

(12) United States Patent
Ohta et al.

(10) Patent No.: US 7,264,959 B2

(45) Date of Patent: Sep. 4, 2007

(54) **SYNTHASE OF CEREULIDE PRODUCED BY *BACILLUS CEREUS*, GENE ENCODING THE SAME AND METHOD OF DETECTING CEREULIDE**

(75) Inventors: Michio Ohta, Kasugai (JP); Norio Agata, Nagoya (JP)

(73) Assignee: Bio Control Institute Limited, Kuwana-Shi (JP)

( * ) Notice: Subject to any disclaimer, the term of this patent is extended or adjusted under 35 U.S.C. 154(b) by 0 days.

(21) Appl. No.: 10/513,786

(22) PCT Filed: May 16, 2003

(86) PCT No.: PCT/JP03/06132

§ 371 (c)(1), (2), (4) Date: Nov. 16, 2004

(87) PCT Pub. No.: WO03/097821

PCT Pub. Date: Nov. 27, 2003

(65) Prior Publication Data

US 2005/0260589 A1 Nov. 24, 2005

(30) Foreign Application Priority Data

May 17, 2002 (JP) ............................ 2002-142398

(51) Int. Cl.

| | |
|---|---|
| ***C12N 1/20*** | (2006.01) |
| ***C12N 9/00*** | (2006.01) |
| ***C12N 15/70*** | (2006.01) |
| ***C12Q 1/68*** | (2006.01) |
| ***C07H 21/04*** | (2006.01) |

(52) U.S. Cl. ...................... 435/252.3; 435/6; 435/69.1; 435/183; 435/320.1; 536/23.2; 536/24.3; 536/24.33; 536/91.2

(58) Field of Classification Search ................ 435/183, 435/23.2, 252.3

See application file for complete search history.

(56) References Cited

U.S. PATENT DOCUMENTS

2001/0053519 A1* 12/2001 Fodor et al. .................. 435/6

FOREIGN PATENT DOCUMENTS

| | | | |
|---|---|---|---|
| CA | 2401268 | | 10/2001 |
| DE | 19937241 | | 2/2001 |
| DE | EP1508622 | * | 2/2005 |
| WO | WO99/51764 | | 10/1999 |

OTHER PUBLICATIONS

Ehling-Schulz et al. Identification and partial characterization of the nonribosomal peptide synthetase gene responsible for cereulide production in emetic *Bacillus cereus*, Appl Environ Microbiol. Jan. 2005;71(1):105-13.*

EMBL Accession No. Q5IRA4, Cereulide peptide synthetase, created May 10, 2005, alignment with SEQ ID No. 1.*

N. Agata, et al.; "*Bacillus cereus* no Oto Dokuso Gosei Idenshi no Kaiseki;" *Japanese Journal of Bacteriology*; vol. 58; No. 1; Feb. 28, 2003; p. 142, WS-8-7.

N. Agata, et al.; "Production of *Bacillus cereus* emetic toxin (cereulide) in various foods;" *Int. J. Food Microbiol.*; vol. 73; No. 1; Feb. 2002; pp. 23-27.

Agata, N. et al; "A novel dodecadepsipeptide, cereulide isolated from *Bacillus cereus* causes vacuole formation in Hep-2 cells"; FEMS Microbiol. Lett 121 (1994) , pp. 31-34.

Kathrin, M. et al; "Toxic and non-toxic strains of the cyanobacterium *Microcystis aeruginosa* contain sequences homologous to peptide synthetase genes"; FEMS Microbiol. Lett. 135 (1996); pp. 295-303.

Agata, N., et al; "*Bacillus cercus* no Oto Dokuso Gosei Idenshi no Kaiseki"; JP J.Bacteriol. vol. 58, No. 1 (Feb. 28, 2003) p. 142-WS-8-7 and English Translation.

Agata, N. et al; "Production of *Bacillus cereus* emetic toxin (cereulide) in various foods"; Int. J. Food. Microbiol., vol. 73, No. 1 (Feb. 2002); pp. 23-27.

Agata, N. et al; "A novel dodecadepsipeptide, cereulide, is an emetic toxin of *Bacillus cereus*"; FEMS Microbiol. Lett. 129 (1995) pp. 17-20.

Agata, N. et al; "Exotoxins of *Bacillus sereus* associated with Food Poisoning" JP J.Bacteriol. 51 (1996), pp. 993-1002.

Agata, N. et al; "Growth Conditions of and Emetic Toxin Production by *Bacillus cereus* in a Defined Medium with Amino Acids" Microbiol. Immunol. 43(1) (1999); pp. 15-18.

Agata, N. et al; "Production of an Emetic Toxin, Cereulide, Is Associated with a Specific Class of *Bacillus cereus*"; Current Microbiology; vol. 33 (1996); pp. 67-69.

Supplementary European Search Report dated Jan. 4, 2005.

XP-002336542—"Forward PCR primer used to detect expression of human ion-11 cDNA;" Nov. 19, 2001.

XP-002336543—"Sequence 15 from patent US5840536;" Oct. 6, 1999.

XP-002261512—Andersson et al; "A Novel Sensitive Bioassay for Detection of *Bacillus cereus* Emetic Toxin and Related Depsipeptide Ionophores;" Applied and Environmental Microbiology, Apr. 1988; pp. 1338-1343.

(Continued)

*Primary Examiner*—Sheridan Swope
*Assistant Examiner*—Iqbal Chowdhury
(74) *Attorney, Agent, or Firm*—Kratz, Quintos & Hanson, LLP

(57) ABSTRACT

It is intended to provide a method of conveniently and quickly detecting cereulide which is an emetic toxin produced by *Bacillus cereus*. Cereulide is detected using the presence of cereulide synthase in a specimen as an indication. The presence of cereulide synthase is examined by detecting a nucleic acid encoding this enzyme or by an immunological method with the use of an antibody specific to the enzyme.

10 Claims, 2 Drawing Sheets

OTHER PUBLICATIONS

XP-002261514—Finlay et al; "Semiautomated Metabolic Staining Assay for *Bacillus cereus* Emetic Toxin;" Applied and Environmental Microbiology, Apr. 1999; pp. 1811-1812.

XP-009021158—Schraft et al; "P-86-Identification of DNA Sequences to Emetic *Bacillus cereus*;" 96th ASM General Meeting; May 19, 1996; p. 384.

XP-002336476—Haggblom et al; "Quantitative Analysis of Cereulide, the Emetic Toxin of *Bacillus cereus*, Produced under Various Conditions;" Applied and Environmental Microbiology, May 2002, pp. 2479-2483.

XP-002261513—Ripabelli et al; "Epidemiological typing of *Bacillus cereus* by amplified fragment length polymorphism;" Letters in Applied Microbiology, 2000, 30, pp. 358-363.

XP-002261511—Hansen et al; "Detection of Enterotoxic *Bacillus cereus* and *Bacillus thuringiensis* Strains by PCR Analysis;" Applied and Environmental Microbiology, Jan. 2001; pp. 185-189.

XP-002094834—Stachelhaus et al; "Modular structure of genes encoding multifunctional peptide synthetases required for non-ribosomal peptide synthesis;" FEMS Microbiology Letters 125 (1995) pp. 3-14.

XP-002265711—Agata et al; "Identification and Molecular Characterization of the Genetic Locus for Biosynthesis of the Emetic Toxin, Cereulide, of *Bacillus cereus*;" Abstract, American Society for Microbiology, 2002; p. 1.

Supplementary European Search Report dated Aug. 8, 2005.

* cited by examiner

ST0 1 2 3 4

SYNTHASE OF CEREULIDE PRODUCED BY *BACILLUS CEREUS*, GENE ENCODING THE SAME AND METHOD OF DETECTING CEREULIDE

This application is a 371 US filing of PCT/JP03/06132, filed May 16, 2003.

TECHNICAL FIELD

The present invention relates to an emetic toxin (cereulide) produced by *Bacillus cereus* and a method of detecting cereulide. The present invention can be used for detecting cereulide in clinical laboratory tests, food inspection, or the like.

BACKGROUND ART

It is known that heat-treatment is invalid to *Staphylococcus aureus* diarrhea toxin and *Bacillus cereus* emetic toxin among bacterial toxins that contaminate into foods to cause food poisoning because they are heat resistant toxins. As to *Staphylococcus aureus* toxin that is extremely important in food hygiene, the detection method thereof is established. Meanwhile, any appropriate methods of detecting *Bacillus cereus* emetic toxin have never been developed to date. Since *Bacillus cereus* forms spores that are resistant to heating at 100° C. for 30 minutes, it is difficult to perfectly kill them by boiling. Therefore, contamination due to *Bacillus cereus* emetic toxin is a problem not only in unheated foods but also in heated foods. *Bacillus cereusis* known worldwide as a bacterium causing food poisoning, and also in Japan, many food poisoning cases due to this bacterium has been reported. In 1994, the emetic toxin (named as "cereulide") was isolated and purified from *Bacillus cereus* and the chemical structure thereof was determined (Agata, N., et al FEMS Microbiol. Lett. 121, 31-34 (1994)). Accordingly, a method of detecting cereulide by using HEp-2 cells was developed (Agata, N., et al FEMS Microbiol. Lett. 121, 31-34 (1994)).

Herein, clarifying the presence of an emetic toxin (cereulide) in foods and other specimens is very important in management of food manufacture according to HACCP, and the development of methods of detecting thereof has been demanded worldwide. However, any methods of carrying out detection of *Bacillus cereus* and detection of cereulide simply and rapidly have never been developed to date. Since the method using HEp-2 cells as mentioned above also requires skilled technique and has difficulty in simple and rapid detection and in treating a large number of specimens simultaneously. Furthermore, in a case where the specimen is vomit, feces, foods or smear samples of a patient, before identification of *Bacillus cereus*, procedures from enrichment culture, isolation culture through pure culture and confirmatory culture have to be carried out. Each culture step needs 18 to 24 hours and about no less than 4 days in total time required.

The present invention has been made under the above-mentioned circumstances, it is an object of the present invention to provide polypeptide and nucleic acid, etc. that can be used for detecting cereulide, and a method of rapidly detecting cereulide using the polypeptide and nucleic acid, etc.

DISCLOSURE OF INVENTION

The present inventors have investigated earnestly in view of the above-mentioned problems. As a result, firstly, they found out enzymes involved in biosynthesis of cereulide and at the same time succeeded in identification thereof. When they compared the base sequence of gene encoding this enzyme with the corresponding gene possessed by *Bacillus cereus* that does not produce cereulide, they found a sequence different between both sequences. They reached finding that the use of this different part makes it possible to detect cereulide. The present invention was made based on the above-mentioned findings and it provides the following configurations.

[1] A polypeptide having an amino acid sequence of SEQ ID NO: 1, or a polypeptide having a sequence in which a part of the amino acid sequence of SEQ ID NO: 1 is modified and which has a synthesis activity of cereulide.

[2] A polypeptide having an amino acid sequence of SEQ ID NO: 3, or a polypeptide having a sequence in which a part of the amino acid sequence of SEQ ID NO: 3 is modified and which has a functional structure of the polypeptide responsible for a synthesis of cereulide.

[3] A nucleic acid encoding either of the polypeptides described in [1].

[4] A nucleic acid encoding either of the polypeptides described in [2].

[5] A vector carrying the nucleic acid described in [3] or [4].

[6] A transformant transformed with the vector described in [5].

[7] A nucleic acid having at least a part of a sequence of a region directly responsible for a synthesis activity of cereulide in a base sequence of SEQ ID NO: 6, or at least a part of the sequence complementary to the base sequence of the region.

[8] A nucleic acid having at least a part of a base sequence of SEQ ID NO: 7 or at least a part of a sequence complimentary to the base sequence.

[9] A nucleic acid having at least a part of a sequence complimentary to a region directly responsible for a synthesis activity of cereulide in a base sequence of SEQ ID NO: 8.

[10] A nucleic acid having at least a part of a sequence complimentary to a base sequence of SEQ ID NO: 9.

[11] A pair of nucleic acids designed so as to specifically amplify a DNA region including at least a part of a region directly responsible for a synthesis activity of cereulide in DNA encoding a polypeptide having a synthesis activity of cereulide.

[12] A solid phase nucleic acid obtained by fixing the nucleic acid described in any of [7] to [10] to an insoluble support.

[13] An antibody which specifically binds to cereulide synthase.

[14] An antibody that has a binding activity to polypeptide containing an amino acid sequence of SEQ ID NO: 1 and does not have a binding activity to polypeptide including an amino acid sequence of SEQ ID NO: 2.

[15] A kit for detecting cereulide, including the nucleic acid described in any of [7] to [10], the nucleic acid described in [11], or the solid phase nucleic acid described in [12].

[16] A kit for detecting cereulide, comprising:

a pair of the nucleic acids described in [11];

an enzyme for amplifying DNA; and a DNA synthesis reagent.

[17] A kit for detecting cereulide, comprising:

the antibody described in [13] or [14]; and an antigen-antibody reaction reagent.

[18] A method of detecting cereulide, the method including steps of examining the presence of (a) or (b) in a specimen, (a) a polypeptide having an amino acid sequence of SEQ ID NO: 1, or a polypeptide having a sequence in which a part of the amino acid sequence of SEQ ID NO: 1 is modified and which has a synthesis activity of cereulide; and (b) a nucleic acid encoding either of the polypeptide described in (a).

[19] A method of detecting cereulide, the method including the following steps of:

(i) carrying out a DNA amplification reaction by using a pair of the nucleic acids described in [11] using DNA in a specimen as a template; and (ii) detecting the amplified DNA.

[20] A method of detecting cereulide, the method including the following steps of:

(iii) preparing cDNA using mRNA in the specimen as a template;

(iv) carrying out a DNA amplification reaction by using a pair of the nucleic acids described [11]; and (v) detecting the amplified DNA.

[21] A method of detecting cereulide, the method including the following steps of:

(I) bringing a specimen into contact with the antibody described in [13] or [14]; and (II) detecting an antigen-antibody reaction product after the step (I).

[22] The method of detecting cereulide described in any one of [18] to [21], wherein the following steps are carried out as a pretreatment:

(A) a step of inoculating a specimen in a growth medium of *Bacillus cereus* and culturing thereof.

[23] The method of detecting cereulide described in any one of [18] to [21], wherein the following steps are carried out as a pretreatment:

(A) a step of inoculating a specimen in a growth medium of *Bacillus cereus* and culturing thereof; and (B) lysing or breaking the cultured *Bacillus cereus.*

Note here that the DNA of the present invention is not limited to a double stranded DNA and is intended to include a single stranded DNA (sense strand and antisense strand). Furthermore, the DNA of the present invention includes DNA having arbitrary base sequences considering the codon degeneracy. Furthermore, the configuration of DNA is not limited and includes a cDNA, a genome DNA, and a synthetic DNA.

Furthermore, in the present invention, polypeptide means a polypeptide in a broad sense and is used as a term including a peptide bond of plural amino acids, which are linked by peptide bond, and includes oligopeptide, polypeptide in a narrow sense and protein.

In the present invention, an emetic toxin produced by *Bacillus cereus* is referred to as cereulide.

BEST MODE FOR CARRYING OUT THE INVENTION

Figure 1:
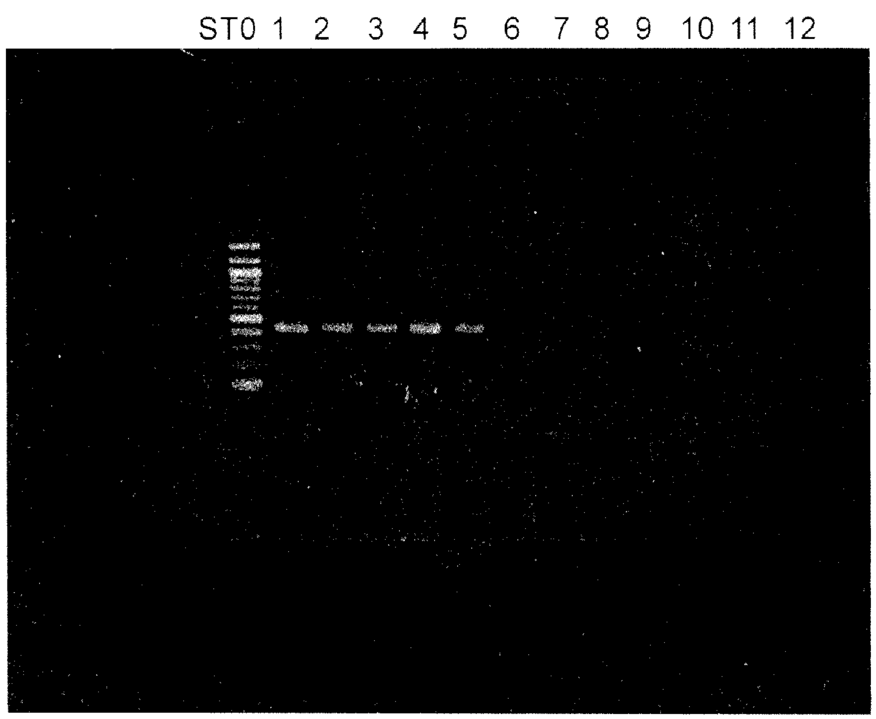
FIG. 1 shows a state of a stained gel in which the gel was obtained by subjecting a PCR amplified product to electrophoresis in an Example of the present invention. The results of solutions after PCR reaction of electrophoresis are shown, where NC7401 strain, NC-T strain, NC-G15 strain, NC327 strain, NC-1-55 strain (strains mentioned above are cereulide-producing strains), ATCC14579 strain, B-4ac strain, PHLS2668 strain, PHLS4433 strain, NC1225 strain (strains mentioned above are cereulide non-producing strain), *Bacillus thuringiensis* (HD73) and *Bacillus sabtilus* (ATCC21332) are shown in this order from the left lane.

The first aspect of the present invention relates to a polypeptide having a synthesis activity of cereulide (hereinafter, also referred to as "cereulide synthase"). The cereulide synthase provided by the present invention contains an amino acid sequence of SEQ ID NO: 1. This enzyme was identified by using a cDNA library of *Bacillus cereus* as shown in Examples mentioned below. *Cereus* synthase is responsible for synthesis of cereulide and found only in *Bacillus cereus* producing cereulide. Therefore, the presence of this enzyme in a specimen reflects the presence of the production of cereulide. Thus, cereulide synthase is useful in that it serves as an index for detecting cereulide.

On the other hand, if an antibody specifically binding to cereulide synthase can be obtained, by an immunological method using this antibody, the detection of the enzyme, that is, the detection of cereulide can be carried out. Therefore, the polypeptide (cereulide synthase) provided by the present invention is useful in that it can be used as an immunogen (antigen) for producing such an antibody.

Herein, a polypeptide containing an amino acid sequence obtained by modifying a part of the amino acid sequence of SEQ ID NO: 1 (hereinafter, referred to as "modified polypeptide") may be used for detecting cereulide similarly to the above-mentioned polypeptide as long as the polypeptide has a synthesis activity of cereulide. An example of such a polypeptide includes a polypeptide containing amino acid sequence of SEQ ID NO: 1 in which a conformation responsible for a synthesis activity of cereulide is conserved.

Herein, "a part of the amino acid sequence is modified" means that one or a plurality of amino acids are deleted, substituted, added and/or inserted in the amino acid sequence. The position of the amino acid to be modified is not particularly limited as long as the synthesis activity of cereulide is maintained. Furthermore, modification may be carried out in a plurality of positions. The number of amino acids to be modified is, for example, a number corresponding to 10% or less of the number of whole amino acids, preferably 5% or less of the number of whole amino acids, and furthermore preferably 1% or less of the number of whole amino acids. The above-mentioned modified polypeptide can be produced by using a well-known genetic engineering technique.

As shown in the below-mentioned Examples, a polypeptide including amino acid sequence of SEQ ID NO: 1 is thought to consist of four domains. In the present invention, these domains are referred to as CRS1, CRS2, CRS3 and CRS4 from the side of N-terminal. From the results obtained by the present inventors, the domains characteristic to cereulide-producing bacteria were CRS3 (1805 to 2824 positions of amino acid sequence) and CRS4 (2825 to 3704 positions of amino acid sequence). Therefore, it was thought that these domains were directly responsible for cereulide biosynthesis. Thus, it is thought that a polypeptide containing either or both of these domains is an antigen particularly effective for producing an antibody specific to cereulide synthase. Consequently, the present invention also provides a polypeptide containing amino acid sequences set forth in SEQ ID NO: 3, SEQ ID NO: 4 or SEQ ID NO: 5. Note here that in these polypeptides, apart of amino acids may be modified as long as a functional structure responsible to cereulide biosynthesis thereof is maintained.

Note here that unless otherwise specified, in the following explanation, "a region directly responsible to cereulide biosynthesis" means a region consisting of amino acids at 1805 to 3704 in the amino acid sequence set forth in SEQ ID NO: 1, that is, regions of CRS3 and CRS4 (in the case of DNA, a DNA region encoding CRS3 and CRS4).

In the polypeptide of the present invention, polypeptides that are present in the natural world can be prepared as a natural polypeptide by way of an operation such as extraction, purification and the like. For example, it can be prepared from a cell of *Bacillus cereus* producing cereulide.

Furthermore, the polypeptide (including a modified polypeptide) of the present invention can be prepared as a recombinant polypeptide by using a genetic technology. That is to say, it can be prepared by transforming an appropriate host cell with a DNA encoding the polypeptide of the present invention and collecting polypeptides expressed in a transformant. The collected polypeptide can be appropriately purified in accordance with the purpose. When it is purified as a recombinant polypeptide, various modifications can be carried out. For example, DNA encoding the polypeptide of the present invention and the other appropriate DNA are simultaneously inserted into a vector, so that it is possible to obtain a recombinant polypeptide in which the polypeptide of the present invention and a peptide or polypeptide encoded by the other DNA are linked to each other. Such modification makes it possible to simplify the extraction and purification of the recombinant polypeptide or addition of the biological function.

The polypeptide of the present invention can be also prepared by a chemical synthesis. For example, it can be synthesized by a solid phase method, etc. that is a well-known peptide synthesizing method.

The second aspect of the present invention provides a nucleic acid encoding the above-mentioned polypeptide of the present invention. A specific example of such nucleic acid may include DNA having a base sequence of SEQ ID NO: 6 or SEQ ID NO: 7, or RNA set forth in SEQ ID NO: 8 or SEQ ID NO: 9. Alternatively, the example includes DNA in which a part of these DNAs, etc. is modified. Herein, the phrase "a part of . . . is modified" means that a part of bases constituting DNA or RNA is deleted, substituted, inserted or added. The number of bases to be modified is, for example, 1 to 100, preferably 1 to 20, and furthermore preferably, 1 to 10.

The nucleic acid of the present invention can be used as a sample in detecting cereulide. That is to say, it is useful in that it can give an index of the presence of cereulide. Furthermore, the nucleic acid of the present invention is useful in that it can be used in a process for preparing an antigen for producing an antibody capable of binding to the above-mentioned polypeptide of the present invention, that is to say, an antibody that can be used for detection of cereulide.

The above-mentioned nucleic acid can be produced by appropriately using a probe and primer, etc. capable of specifically hybridizing to genes encoding cereulide synthase (DNA having a base sequence of SEQ ID NO: 6) from an appropriate genome DNA library or a cDNA library, or a bacterial extract of cereulide-producing bacteria. Furthermore, they can be synthesized by a PCR method by using at least a part of genes encoding cereulide synthase as a template and using dNTP (dATP, dGTP, dCTP and dTTP) as a material.

A genome DNA library or cDNA library for preparing the DNA of the present invention can be produced according to a conventional method from, for example, *Bacillus cereus* strain NC7401.

The present invention also provides a vector carrying the above-mentioned DNA (including modified DNA) of the present invention. Any vectors can be used as long as it can carry the DNA of the present invention. However, it is preferable that in accordance with the purpose of use (cloning, expression of polypeptides) and considering kinds of host cells, an appropriate vector is selected. The insertion of DNA into the vector in the present invention can be carried out, for example, by using a well-known method using restriction enzyme and DNA ligase (Molecular Cloning, Third Edition, 1.84, Cold Spring Harbor Laboratory Press, New York).

The present invention further provides a transformant carrying the above-mentioned DNA (including modified DNA) of the present invention. That is to say, it relates to a transformant obtained by transforming a host cell with the DNA of the present invention. For example, the DNA of the present invention can be transformed by incorporating it into a host cell by a well-known gene incorporating method such as a potassium phosphate method, electroporation (Potter, H. et al., Proc. Natl. Acad. Sci. U.S.A. 81, 7161-7165 (1984)), lipofection (Felgner, P. L. et al., Proc. Natl. Acad. Sci. U.S.A. 84, 7413-7417 (1984)), microinjection (Graessmann, M. & Graessmann, A., Proc. Natl. Acad. Sci. U.S.A. 73,366-370 (1976)), and the like. Furthermore, the transformant of the present invention can be obtained by transforming the host cell with the vector of the present invention. It is possible to use various kinds of host cells in accordance with the purposes and, for example, it is possible to use a procaryotic cell such as *Escherichia coli*, and an eucaryotic cell such as yeast. In a case where a system of *Escherichia coli* is used, pET vector (Novagen) such as pET-3c and pET-8c, etc., pBAD plasmid (Invitrogen), pGEX plasmid (Amersham Pharmacia biotech), and the like can be used as a vector.

By culturing the transformant of the present invention under appropriate conditions, a large amount of expression products (polypeptides) of the DNA of the present invention can be produced. This expression product can be used for producing antibodies that can be used for detecting, for example, cereulide synthase. Note here that by expressing as an fused protein (peptide) with His-Tag consisting of several histidines, β-D-galactosidase, GST (glutathione S-transferase), thioredoxin, maltose binding protein, Myc, Xpress, FLAG, and the like, the expression products can be easily purified.

The third aspect of the present invention relates to a method of detecting cereulide, and the method includes the steps for examining the presence of (a) or (b). (a): a polypeptide including an amino acid sequence of SEQ ID NO: 1, or a polypeptide including a sequence in which a part of the amino acid sequence of SEQ ID NO: 1 is modified and which has a synthesis activity of cereulide, or (b) a nucleic acid encoding either of the polypeptides described in (a). Note here that since the presence of cereulide in a specimen means the presence of *Bacillus cereus* producing cereulide, the term "a method of detecting cereulide" is used as a same meaning as the term "a method of detecting the presence of *Bacillus cereus* producing cereulide."

The method of examining the presence of (a) is not particularly limited. However, it is possible to use an immunological method using an antibody specific to the polypeptide to be detected.

Similarly, a method of examining the presence of (b) is not particularly limited. It is possible to use, for example, a method using a nucleic acid primer and/or a nucleic acid probe specific to the nucleic acid encoding the polypeptide to be detected, or a PCR (polymerase chain reaction) method using a pair of primers (nucleic acid) designed to specifically amplify a region specific to cereulide synthase and the modification method thereof or application method (PCR-RFLP (restriction fragment length polymorphism) method, RT-PCR (reverse transcriptase PCR) method, etc.), a Southern blotting hybridization method, a dot hybridization method (Southern, E., J. Mol. Biol. 98, 503-517(1975)), a northern blotting method, and the like.

Hereinafter, more specific examples of the methods of detecting cereulide provided by the present invention will be described. Firstly, as an example using nucleic acid amplification reaction such as a PCR method, etc., a method including the following (i) and (ii) can be used. (i) a step of carrying out a DNA amplification reaction using a pair of nucleic acids designed so as to specifically amplify a DNA region including at least a part of a region (for example, DNA region consisting of a base sequence of SEQ ID NO: 7) directly responsible for a synthesis activity of cereulide in DNA (for example, DNA consisting of a base sequence of SEQ ID NO: 6) encoding a polypeptide having a synthesis activity of cereulide by using DNA in a specimen as a template, and (ii) a step of detecting an amplified DNA. Furthermore, as a method using a RT-PCR method, a method including (iii), (iv) and (v) can be used. (iii) a step of preparing cDNA using mRNA in a specimen as a template; (iv) a step of carrying out DNA amplification reaction using a pair of nucleic acids designed so as to specifically amplify a DNA region including at least a part of a region directly responsible for a synthesis activity of cereulide in DNA encoding a polypeptide having a synthesis activity of cereulide; and (v) a step of detecting the amplified DNA.

Since an amplified region specified by a pair or primers is required to have a size capable of being amplified by a PCR method etc., the size is preferably about 4000 bp or less. Meanwhile, when the amplified region is too small, it becomes difficult to differentiate between the amplified product and a dimer of the primer, the size is preferably 50 bp or more. Furthermore, for effective amplification, it is preferable that the size of the amplification region is about 100 bp to 1000 bp.

A temperature for denaturing a double stranded nucleic acid in a PCR method etc. is about 90° C. to about 95° C. An annealing temperature for hybridizing a primer is, for example, about 37° C. to about 65° C., and polymerization temperature is, for example, about 50° C. to 80° C. In the PCR method and the modification method thereof, etc., a cycle including the heat denaturing, annealing and polymerization is repeated until the amplification products are detectable. The amplification product can be detected by using an agarose electrophoresis. That is to say, it is possible to confirm the presence and the length of a nucleic acid fragment amplified by subjecting an enzyme reaction solution to agarose electrophoresis. From the results of this electrophoresis, it is possible to determine the presence of nucleic acid having a sequence recognized by a primer in a specimen, thus making it possible to determine the presence of cereulide, that is to say, the presence of *Bacillus cereus* producing cereulide. For detecting the amplification product, in addition to the agarose electrophoresis, other electrophoresis and various chromatographies can be used.

Nucleic acids (for a primer or for a probe) that can be used in the method of detecting cereulide of the present invention is not particularly limited as long as they can be used for specifically detecting genes encoding cereulide synthase. For example, an example of the nucleic acid may include a nucleic acid containing at least a part of a sequence of a region directly responsible for a synthesis activity of cereulide in a base sequence of SEQ ID NO: 6, or a nucleic acid containing at least a part of a sequence complementary to the base sequence of the above-mentioned region. Herein, "a region directly responsible for a synthesis activity of cereulide" concretely means a region encoding CRS3 and CRS4, that is to say, a region having a base sequence of SEQ ID NO: 7. Similarly, in a case where mRNA in a specimen is used as a subject to be detected, it is possible to use a nucleic acid containing at least a part of a sequence complementary to a base sequence of a region directly responsible for a synthesis activity of cereulide in a base sequence of SEQ ID NO: 8. More concrete example may include a nucleic acid containing at least a part of a sequence complimentary to a base sequence of SEQ ID NO: 9.

As the probe and primer, in accordance with the analyzing method, a DNA fragment or a RNA fragment can be appropriately used in accordance with the analyzing method. The base length of the probe and primer may be a length capable of exhibiting a respective function, respectively. The base length of the primer is 10 bp or more, preferably 15 bp or more, concretely about 10 to 30 bp, and preferably about 15 to 25 bp when the selectivity or detection sensitivity and reproducing property are considered.

Note here that a primer may have some mismatch with respect to a sequence that is used as a template as long as the primer can specifically hybridizes to a subject to be amplified and amplify a targeted DNA fragment. The extent of the mismatch is 1 to several, preferably 1 to 5, and furthermore preferably 1 to 3. Also as in the probe, the probe may have some mismatch with respect to a sequence to be detected as long as the mismatch doesn't affect the detection.

Followings are concrete examples of the nucleic acids (primer set) that can be used for the method of detecting cereulide using a method with amplification of the specific DNA region, for example, a PCR method, etc.

```
Primer set 1
Sense strand primer:
5'-GGTGAATTGTGTCTGGGAGG-3'        (SEQ ID NO: 10)

Antisense strand primer:
5'-ATTTTTATTAAGAGGCAATG-3'        (SEQ ID NO: 11)

Primer set 2
Sense strand primer:
5'-GTCAAGATAAGAGGCTTCCGAATT-3'    (SEQ ID NO: 12)

Antisense strand primer:
5'-AATGGAATGACCACCAAGCT-3'        (SEQ ID NO: 13)

Primer set 3
Sense strand primer:
5'-AGGAAGTTCCGTTTGTGGAC-3'        (SEQ ID NO: 14)

Antisense strand primer:
5'-CACATAACCTTTTGCAACTC-3'        (SEQ ID NO: 15)

Primer set 4
```

-continued

```
Sense strand primer:
5'-GGCGAACTATGTGTTGGTGG-3'        (SEQ ID NO: 16)

Antisense strand primer:
5'-TAAAGAGTCACCACCATAAG-3'        (SEQ ID NO: 17)

Primer set 5
Sense strand primer:
5'-ACGTCAGGCAGTACTGGAAA-3'        (SEQ ID NO: 18)

Antisense strand primer:
5'-TTCGATGCGGAATCCACGAA-3'        (SEQ ID NO: 19)
```

Nucleic acid (primer and probe) of the present invention can be synthesized by a well-known method such as a phosphodiester method. Furthermore, as a labeling material and labeling method in a case where it is used as a probe, well-known labeling materials and labeling methods can be employed. Herein, examples of the labeling materials may include a radioisotope such as $^{32}$P, a fluorescent material such as fluorescein isothiocyanate, tetramethylrhodamine isothiocyanate, and the like; and examples of the labeling method may include 5' labeling method using alkaline phosphatase and T4 polynucleotide kinase, 3' labeling method using T4DNA polymerase and Klenow fragment, a nick-translation method, a random primer method (Molecular Cloning, Third Edition, Chapter 9, Cold Spring Harbor Laboratory Press, New York), and the like.

Next, a method of detecting cereulide using immunological method will be explained. An example of the method of detecting cereulide using immunological method may include a method including: I) a step of bringing a specimen into contact with an antibody specific to cereulide synthase; and II) a step of detecting antigen-antibody reaction product after the step I (step II). Herein, “an antibody specific to cereulide synthase” means an antibody having a binding property specific to cereulide synthase. Concrete examples thereof include an antibody that has a binding property to a polypeptide containing an amino acid sequence of SEQ ID NO: 1 and does not have a binding property to a polypeptide containing an amino acid sequence of SEQ ID NO: 2. Class of antibodies to be used is not particularly limited and antibodies classified into, for example, IgG class, IgM class, etc. can be used. Furthermore, antibody fragments such as Fab, Fab', F(ab')2, scFv, dsFv, etc. may be used.

Herein, an example of the measuring method may include qualitative or quantitative method such as, for example, an ELISA (Enzyme-linked immunosorbent assay) method, radioimmunoassay, FACS, an immunoprecipitation method, immuno blotting, and the like. Furthermore, as kinds of antigen-antibody reactions, either of a method of competitively reacting cereulide synthase in a specimen and additionally added cereulide synthase with respect to an antibody specific to cereulide synthase (competitive method) and a method that does not react competitively (noncompetitive method) may be employed.

It is preferable to use a monoclonal antibody as an antibody specific to cereulide synthase. It is advantageous because high sensitive measurement can be carried out due to high specificity of monoclonal antibody. Furthermore, it is preferable to use a sandwich method using two kinds of antibodies recognizing epitopes that are specific to cereulide synthase and different from each other from the viewpoint of sensitivity and specificity.

It is possible to use antibody in a solid phase. As an insoluble support used for making a solid phase, water-insoluble materials, for example, resin such as polystyrene resin, polycarbonate resin, silicon resin, nylon resin, etc. or glass, and the like may be used, and the material is not particularly limited. This insoluble support can support antibodies by physical adsorption or chemical adsorption.

Examples of the labeled material to be used in immunoassay may include enzyme such as peroxidase, alkaline phosphatase, β-D-galactosidase, glucose oxidase, glucose-6-phosphate dehydrogenase and micro peroxidase, etc.; fluorescent material such as fluorescein isothiocyanate (FITC), tetramethylrhodamine isothiocyanate (TRITC) and europium, etc.; chemiluminescent material such as luminal, isoluminol and acridinium derivatives, etc.; coenzyme such as NAD; biotin; and radioactive substance such as $^{131}$I and $^{125}$I, and the like. In particular, with a method in which biotin is used as a labeled material and avidin (for example, avidin peroxidase) labeled with fluorescent dye or enzyme is reacted, measurement with higher sensitivity can be carried out.

A monoclonal antibody specifically binding to cereulide synthase can be obtained by a conventional method. Hereinafter, an example of the method of producing a monoclonal antibody will be described. Firstly, cereulide synthase is obtained and used as an antigen. Animal such as a mouse is immunized with this antigen. Thereafter, antibody-producing cells are extracted from the immunized animal and the extracted cells are fused with myeloma cells so as to obtain hybridoma cells. Subsequently, these hybridomas are made to be monoclonal, and then clones producing antibodies specifically binding to cereulide synthase is selected.

As the antigen, cereulide synthase that was isolated and purified from bacterial body of *Bacillus cereus* producing cereulide can be used. Furthermore, a base sequence encoding cereulide synthase is used, and a recombinant polypeptide obtained by using an expression system such as *Escherichia coli* can be used.

As an immunization method, for example, the following procedure may be employed: the above-mentioned antigen is mixed with Freund’s complete adjuvant or Freund’s incomplete adjuvant to be emulsified; a mouse is immunized with the emulsified antigen by intraperitoneal, subcutaneous, or intramuscular injection several times at predetermined intervals. An example of animals to be immunized includes rat, hamster, rabbit, guinea pig, chicken, sheep, goat, etc. in addition to mouse. After completion of immunization, the spleen is extracted from an immunized animal and antibody-producing cells are obtained. The antibody-producing cells may be collected from the lymph node, peripheral blood, etc.

The kinds of myeoma cells to be used are not particularly limited and appropriate myeloma cells can be selected with regard to an animal to be used. It is preferable to use myeloma cells derived from animals that are the same kinds of antibody-producing cells. For example, in a case where a mouse is used, myeloma cell line PAI can be used. Cell fusion is carried out by mixing an antibody-producing cells and myeloma cells at a predetermined ratio, and then adding polyethylene glycol thereto and stirring thereof. Furthermore, cell fusion can be carried out by using electrical pulse.

In order to select only hybridomas in which cell fusion was carried out, a general HAT medium (a selective medium containing a predetermined ratio of hypoxanthine, aminopterin, and thymidine) can be carried out. A culture containing hybridoma is cultivated in a container such as a 96-well plate so as to be selected later.

Next, a culture supernatant in each container was collected, and hybridoma producing antibody to cereulide synthase was selected by an ELISA method, etc. using cereulide synthase. An antibody-positive hybridoma in a container is cloned by limiting dilution technique so as to obtain a monoclonal hybridoma cell line.

A desired antibody can be obtained by purifying culture of hybridoma. Furthermore, after amplifying hybridomas to a desired number or more, the hybridomas are transplanted into a peritoneal cavity of an animal (for example, a mouse) and allowed to proliferate ascites fluid, and then the ascites fluid is purified, thereby obtaining a desired antibody. For purifying the above-mentioned culture or purifying the ascites fluid, affinity chromatography using protein G, protein A, etc. is preferably used. Furthermore, affinity chromatography in which an antigen is made into a solid phase can be used. Furthermore, ion exchange chromatography, gel filtration chromatography, ammonium sulfate fractionation, and centrifugation, and the like can be used. These methods can be used solely or in any combination thereof.

Whether or not the antibody obtained by the above-mentioned method specifically recognize cereulide synthase can be confirmed by, for example, an ELISA method using plate in which cereulide synthase is made into a solid phase.

The nucleic acid (primer or probe) used in the method of detecting cereulide of the present invention can be used in a state in which it is fixed to an insoluble support. Similarly, the antibody used in the method of detecting cereulide of the present invention can be used in a state in which it is fixed to an insoluble support. By processing the insoluble support to be used in making a solid phase in a shape of chip, beads, etc., it is possible to carry out the detection of cereulide in the specimen simply by using these fixed nucleic acid or fixed antibody.

The further aspect of the present invention provides a kit that can be used for detection of cereulide. That is to say, by using nucleic acid (including a pair of nucleic acids, solid phase nucleic acid) used for detection of cereulide, it is possible to construct a kit for detecting cereulide. The kit for detecting cereulide may include an enzyme for amplifying nucleic acid (for example, DNA synthase used for, for example, a PCR method) or nucleic acid (dATP, dCTP, dGTP, and dTTP) as a substrate, reaction reagent, and the like. Furthermore, as a standard material, it can contain cereulide synthase (which may also include a partial purified product), and intracellular extract (which may also include partial purified product) in a cereulide-producing cell line.

According to the above-mentioned kit for detecting cereulide, cereulide can be detected by targeting a nuclide acid in the specimen, but a kit for detecting cereulide by targeting a polypeptide in a specimen, i.e., cereulide synthase can be constructed. Such a kit contains the above-mentioned antibody specific to cereulide synthase (including a solid-phase antibody). Besides, a kit can be constructed including a secondary antibody bonded to the antibody, antigen-antibody reaction reagent (buffer, chromogenic substrate, chromogenic reagent, chromogenic reaction stopping solution, etc.) and the like. Furthermore, a kit may include cereulide synthase (which may also include a partially purified product) and intracellular extract of a cereulide-producing cell line (which may also include a partially purified product) as a standard material.

Specimens used for a method of detecting cereulide of the present invention are not particularly limited. Examples of the specimen may include specimens, various foods, vomit or faces of human or animals, smear samples, or the like. These specimens are subjected to a treatment with enzyme such as lysozyme, a pressure treatment, a heat treatment or ultra sonic treatment, etc. Bacterial bodies in the specimen are lysed or broken with such treatment. However, if it can be expected that cytoplasmic membrane of *Bacillus cereus* in the specimen is broken at the point when the specimen is collected, the lysing treatment is not necessary.

Herein, it is preferable that samples from the subject to be examined have been cultured in advance by using a growth medium (selective medium). By employing this culturing step, detection with higher reliability can be carried out.

Note here that in a case where a subject to be examined is in a liquid state, samples can be directly used in a treatment such as lysis or culture process. However, in a case where a subject to be examined is in a solid state, it is preferable that bacterial bodies are extracted by using an appropriate solvent once, and then it is used in such treatment.

Hereinafter, the present invention will be described in more detail with reference to Examples.

EXAMPLE 1

Cloning of Emetic Toxin (Cereulide) Synthase from *Bacillus Cereus* Genome DNA Library From *Bacillus cereus* NC7401 strain (deposited in Nagoya City Public Health Research Institute, National Institute of Health Sciences), a phage library was produced by using EMBL3 (Promega Corporation). About 400 of the resultant white plaques were screened, and a region specifically conserved in amino acid synthase without through a ribosome, which was a DNA fragment specifically amplified using BSC I (GGAATTCCTTAAAIGCIGGAGGAGCI-TATGTGCCGCTTGATCC: SEQ ID NO: 20) and II (GGAATTCCTTTIGGITTICClGTTGTIC-ClGAIGTGTAAAT: SEQ ID NO: 21) as primers, was analyzed by a Southern hybridization method. Note here that a probe obtained by labeling a DNA fragment, which was amplified by a PCR method using chromosome DNA of NC7401 strain as a template and using BSC I and II as primers, with DIG Labeling Kits (Roche Diagnostics) was used. As a result of analysis, a plurality of insert DNA with a large expression amount are selected and they are cut by a restriction enzyme SalI and subcloned into a multi-cloning site of a cloning vector pHSG299 (TAKARA SHUZO CO., LTD.).

EXAMPLE 2

Analysis of Sequence of Emetic Toxin (Cereulide) Synthase cDNA

The sequence of each of the subcloned DNA fragments was analyzed by a cycle sequence reaction using an automatic sequencer (Applied Biosystem). By analyzing sequence information of each DNA fragment while considering overlapped sequences, a full-length DNA sequence and an amino acid sequence of cereulide synthase were determined (SEQ ID NO: 1). When this sequence was investigated in detail, cereulide synthase consists of four domains, each of which synthesizes one amino acid respectively. Two domains at N-terminus were conserved widely also in cereulide strains that do not produce cereulide, but two domains at C-terminus are specific to strains producing cereulide.

EXAMPLE 3

Detection of Cereulide Using PCR Method (3-1) Preparation of Specimen

Specimens were prepared from *Bacillus cereus* (cereulide-producing strains and cereulide non-producing strains: 5 strains each) shown in a Table of FIG. 1 in accordance with the following procedures. As a control group, *Bacillus thuringienesis* and *Bacillus subtilis* were used.

Each bacterial body was respectively inoculated in an appropriate enrichment medium (LB medium) and cultured under aerobic conditions at 37° C. over night, followed by collecting bacterial bodies from 1.5 ml of cultured medium by centrifugation. The collected bacterial bodies were washed with 10 mM Tris buffer (pH7.5) once, and then suspended in 0.5 ml solution in which lysozyme was dissolved in the buffer so that the concentration became 1 mg/ml, which was allowed to stand in this state at 37° C. for 10 minutes to be lysed. Subsequently, equivalent amount of phenol saturated with the above-mentioned buffer was added to the lysate and stirred sufficiently. Centrifugation was carried out, followed by collecting a supernatant solution and subjecting it to ethanol precipitation treatment so as to precipitate the nucleic acid components. The resultant precipitate was dissolved in 1 ml of the above-mentioned buffer. This solution was used as a specimen in the detection method mentioned below.

(3-2) Synthesis of Primer for PCR

Based on the base sequence information of cereulide synthase shown in SEQ ID NO: 6, a sequence specific to the cereulide-producing strain was selected and the following primers (oligonucleotide) were chemically synthesized.

```
Sense strand primer:
5'-GGTGAATTGTGTCTGGGAGG-3'   (SEQ ID NO: 10)

Antisense strand primer:
5'-ATTTTTATTAAGAGGCAATG-3'   (SEQ ID NO: 11)
```

(3-3) PCR Method

A reaction solution (about 30 μl in total) was prepared by adding 16.05 μl of sterile distilled water, 3 μl of 10× reaction buffer, 4.8 μl of dNTP solution, 1.5 μl of sense strand primer, 1.5 μl of antisense strand primer, and 0.150 μl of heat resistant DNA polymerase into 3 μl of each of the above-mentioned specimen. Note here that the composition of 10× reaction buffer consists of 500 mM KCl, 100 mM Tris-HCl (pH8.3), 15 mM $MgCl_2$ and 0.1% (w/v) gelatin. The dNTP solution was a solution obtained by mixing dATP, dCTP, dGTP and dTTP so that the respective final concentration became 1.25 mM. Furthermore, each primer was an aqueous solution (50 DU/ml) of chemically synthesized purification material obtained in (3-2). As a heat resistant DNA polymerase, Taq DNA polymerase (5 unit/ml: Perkin Elmer Cetus) was used.

The PCR was carried out under the following conditions: heat denaturation: 94° C. for 1 minute, annealing: 55° C. for 1 minute, and polymerization reaction: 72° C. for 1 minute. A process from heat denaturation to polymerization reaction by way of annealing was defined as 1 cycle. This cycle was carried out 35 times. Note here that PCR reaction was carried out by the use of DNA Thermal Cycler (Perkin Elmer Cetus).

(3-4) Detection of PCR Amplification Product

In order to detect amplified DNA fragments from PCR reaction solution, agarose electrophoresis was carried out under the following conditions. As an agarose gel, a gel having a gel concentration of 2% (w/v) was used. Staining of gel after electrophoresis was carried out by the use of ethidium bromide (0.5 μg/ml). The electrophoresis was carried out under the conditions: applied voltage: 100V, and electrophoresis time: 30 minutes. The other conditions and operation methods of electrophoresis followed a method described in Molecular Cloning, Third Edition, Cold Spring Harbor Laboratory Press, New York.

FIG. 1 shows a stained gel. In FIG. 1, the results of solutions after PCR reaction of electrophoresis are shown in which NC7401 strain, NC-T strain, NC-G15 strain, NC327 strain, NC-I-55 strain (strains mentioned above are cereulide-producing strains), ATCC14579 strain, B-4ac strain, PHLS2668 strain, PHLS4433 strain, NC1225 strain (strains mentioned above are cereulide non-producing strain), *Bacillus thuringiensis* (HD73), *Bacillus sabtilus* (ATCC21332) are shown in this order from the left lane. As shown in FIG. 1, in the cereulide-producing strain (lanes 1 to 5), it is shown that PCR amplification product of about 450 bp was obtained. Meanwhile, in the cereulide non-producing strain and *Bacillus thuringiensis* HD73, *Bacillus sabtilus* ATCC21332, bands corresponding to this PCR amplification product were not detected. From the above-mentioned results, it was confirmed that by the methods according to this Example, the cereulide-producing strain, that is, the cereulide could be specifically detected.

EXAMPLE 4

Micro Detection of Cereulide-Producing *Bacillus cereus* by Using PCR Method (4-1) Calculation of the Amount of DNA in Specimen By using *Bacillus cereus* NC7401 strain shown in a Table of FIG. 1, specimen was prepared in accordance with the method shown in (3-1) of Example 3 to obtain a purified DNA preparation. Then, the amount of DNA in this preparation was calculated by measuring absorbance at the wavelength of 260 nm.

(4-2) Detection of PCR Amplification Product

Figure 2:
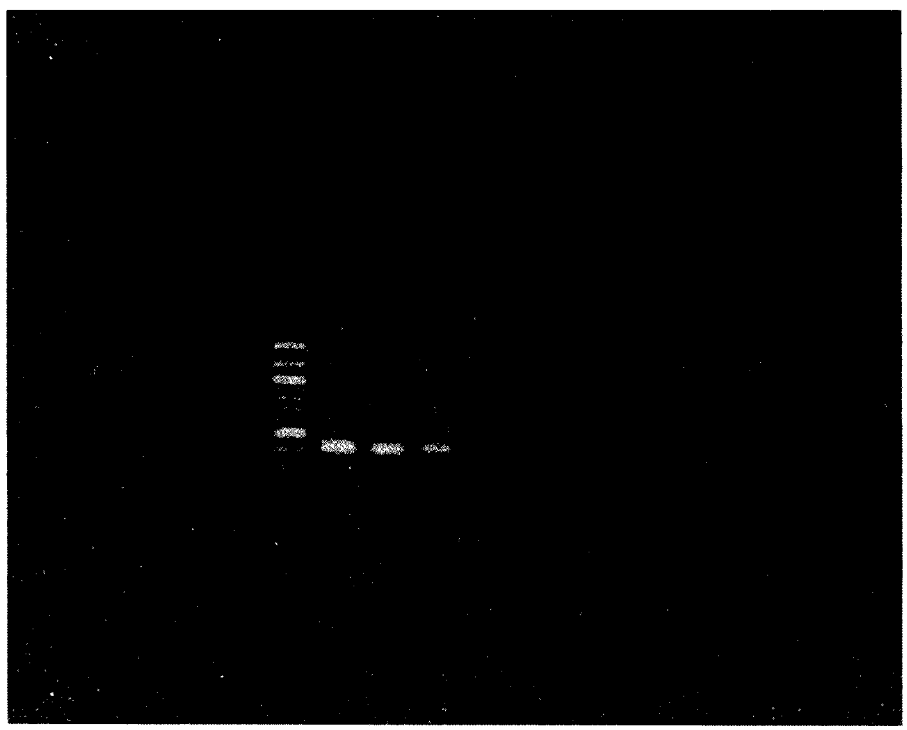
FIG. 2 shows a state of a stained gel obtained by subjecting PCR amplified products having different DNA concentrations to electrophoresis. Lanes No. 1, 2, 3 and 4 are lanes showing PCR amplified products from samples of 300 ng, 3 ng and 0.3 ng are subjected to electrophoresis, respectively.

By diluting a specimen with reference to the amount of DNA calculated in (4-1), samples respectively containing DNA in the amount of 300 ng (number of molecules: about $1\times10^{2}$), 30 ng (number of molecules: about $1\times10^{1}$), 3 ng (number of molecules: about 1) and 0.3 ng (number of molecules: about $1\times10^{-1}$) were prepared. By using these samples, PCR reaction was carried out by the methods described in (3-2) and (3-3) of Example 3, followed by detection of a PCR amplification product by the method described in (3-4). FIG. 2 shows a state of a stained gel obtained by subjecting each of the PCR amplified products to electrophoresis. Lanes No. 1, 2, 3 and 4 are lanes showing PCR amplified products from samples of 300 ng, 3 ng and 0.3 ng are subjected to electrophoresis respectively. Even in lane 3, i.e., in a case where a sample containing 3 ng of DNA was used, a band of interest can be confirmed. This means that DNA amount corresponding to 1 to several molecules of *Bacillus cereus* chromosome is detected. Thus, theoretically, if several molecules of the cereulide-producing *Bacillus cereus* are present in the specimen, the presence of the cereulide-producing *Bacillus cereus*, that is, cereulide can be detected.

The present invention is not limited to the description of the above embodiments. A variety of modifications, which are within the scopes of the following claims and which are achieved easily by a person skilled in the art, are included in the present invention.

INDUSTRIAL APPLICABILITY

The present invention provides the amino acid sequence and the base sequence of an emetic toxin (cereulide) produced by *Bacillus cereus*, thereby making it possible to detect cereulide using a nucleic acid probe and an antibody. The use of the antibody or nucleic acid probe specific to cereulide enables simple and rapid detection of cereulide. In one example of the detection method of the present invention shown in Examples, it took about 3 hours to amplify nucleic acid in a specimen and about 30 minutes to obtain the detection results thereafter. Thus, it was possible to detect cereulide, which had never been detected conventionally, for extremely short time.

Furthermore, according to the method of the present invention, it is possible to detect cereulide with high sensitivity. This means that cereulide can be detected from a small amount of detection and that a pretreatment of specimens can be simplified. Furthermore, in the method of detecting cereulide, instead of detecting cereulide directly, the presence of cereulide synthase is examined, and from the results, the presence of cereulide in the specimen is determined. As the characteristics common to strains producing cereulide in *Bacillus cereus*, it is thought that they have a cereulide synthase activity identified in the present invention and, that is to say, the cereulide-producing strain necessarily contains cereulide synthase genes. Moreover, since no other species that produce the same toxin as cereulide has been known, by allowing cereulide synthase or gene encoding thereof to be a target for detection, it is possible to specifically or selectively detect the presence of cereulide in a specimen (the presence of cereulide-producing bacteria). Therefore, result with high reliability can be obtained and so the present invention becomes suitable for food evaluation and clinical laboratory tests.

We claim:

1. An isolated nucleic acid whose sequence consists of a coding sequence encoding the polypeptide having the amino acid sequence of SEQ ID NO: 1.

2. A vector whose sequence comprises the nucleic acid sequence described in claim 1.

3. An isolated cell transformed with the vector described in claim 2.

4. A composition consisting of a pair of nucleic acids, wherein each nucleic acid of said pair is an isolated nucleic acid whose sequence consists of at least 15 nucleotides or more of a sequence encoding a polypeptide having cereulide synthesis activity in the nucleotide sequence of SEQ ID NO: 6, or at least 15 nucleotides or more of the sequence complementary to said encoding sequence region, said pair of nucleic acids being designed so as to specifically amplify a DNA region comprising at least a part of a region encoding a polypeptide having cereulide synthesis activity.

5. A kit for detecting a cereulide polynucleotide, comprising:

the pair of the nucleic acids described in claim 4;

an enzyme for amplifying DNA; and a DNA synthesis reagent.

6. The isolated cell of claim 3, wherein the cell is a procaryotic cell.

7. The isolated cell of claim 3, wherein the cell is an eucaryotic cell.

8. A composition consisting of an isolated nucleic acid whose sequence consists of at least 30 bp or more of a sequence of a region encoding a polypeptide having cereulide synthesis activity in the nucleotide sequence of SEQ ID NO: 6, or at least 30 bp or more of the sequence complementary to the nucleotide sequence of the region, wherein the nucleic acid has 30 bp or more of a sequence of SEQ ID NO: 7, or 30 bp or more of the sequence complementary to the nucleotide sequence of SEQ ID NO: 7.

9. A composition consisting of an isolated nucleic acid whose sequence consists of at least 15 contiguous nucleotides or more of a sequence of a region encoding a polypcptide having cereulide synthesis activity in the nucleotide sequence of SEQ ID NO: 6, or at least 15 bp or more of the sequence complementary to the nucleotide sequence of the region, wherein the nucleic acid has the nucleotide sequence of any one selected from the group consisting of SEQ ID NO:10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 19.

10. A kit for detecting a cereulide polynucleotide, comprising the nucleic acid described in claim 9.

* * * * *

SEQUENCE LISTING

```
<160> NUMBER OF SEQ ID NOS: 21

<210> SEQ ID NO 1
<211> LENGTH: 3704
<212> TYPE: PRT
<213> ORGANISM: Bacillus cereus

<400> SEQUENCE: 1

Phe Ile Lys Ser Met Asn Gln Leu Gly Lys Ser Lys Asn Leu His Asn
1               5                   10                  15

Gly Gly Met Met Glu Met Lys Arg Val Glu Glu His Asp His Ile His
            20                  25                  30

Val Leu Asn Glu Ile Glu Asn Glu Cys Glu Arg Arg Tyr Gly Arg Ser
        35                  40                  45

Asn Ile Ala Ile Met Leu Glu Lys His Gly Val His Glu Gln Pro Leu
    50                  55                  60

His Ile Glu Asp Leu Phe His Glu Val Glu Met Gln Glu His Ser Arg
65                  70                  75                  80

Val Ser Arg His Glu Thr Val Leu Met Thr Asp Lys Gln Cys Ile Asp
                85                  90                  95

Glu Ser Gly Lys Pro Leu Ala Leu Arg Phe Gly Glu Pro Leu His Leu
            100                 105                 110

Asp Asp Cys Thr Pro Lys Thr Leu Gln Glu Ile Leu Lys Arg Ala Ala
        115                 120                 125

Lys Gln Ala Lys Asp Lys Gly Met Thr Phe Val Tyr Glu Asp Gly His
    130                 135                 140

Glu Glu Tyr Leu Ser Tyr Gln Glu Met Leu Ala Asp Ala Glu Arg Leu
145                 150                 155                 160

Leu Lys Gly Leu Arg Asn Leu Gly Ile Gln Pro Gly Glu Ser Ile Leu
                165                 170                 175

Phe Gln Phe Lys Asp Asn Lys His Phe Val Thr Ala Phe Trp Ala Cys
            180                 185                 190

Ile Leu Gly Gly Phe Leu Pro Thr Pro Leu Gly Thr Ala Pro Ile Tyr
        195                 200                 205
```

-continued

```
Ser Glu Gln Asn Ala Gln Val Leu Lys Leu Tyr Asn Thr Trp Gln Leu
    210                 215                 220

Leu Glu Gln Pro Ile Ile Leu Thr Glu Phe Glu Leu Lys Glu Glu Ile
225                 230                 235                 240

Ala Ala Ile Arg Thr Thr Leu Gln Arg Gln Glu Ile Val Ile His Ser
                245                 250                 255

Ile Glu Asn Val Met Asp Thr Ala Arg Asp Thr Asn Trp Phe Pro Cys
            260                 265                 270

Thr Glu Asp Thr Ile Val Leu Asn Leu Leu Thr Ser Gly Ser Thr Gly
        275                 280                 285

Val Pro Lys Cys Val Gln His Lys Ser Lys Ser Ile Ile Ala Arg Thr
    290                 295                 300

Val Ser Asn Cys Ile Asp Arg Gln Leu Asp Glu Lys Glu Val Ser Leu
305                 310                 315                 320

Asn Trp Met Pro Leu Asp His Val Gly Gly Ile Val Met Cys His Ile
                325                 330                 335

Arg Asp Thr Tyr Leu Met Cys Gln Gln Val Asn Cys Leu Ile Ser Ala
            340                 345                 350

Phe Ile Glu Asn Pro Leu Asn Trp Leu His Trp Ile Asp Ala Tyr Ser
        355                 360                 365

Ala Thr Phe Thr Trp Ala Pro Asn Phe Ala Phe Ser Leu Ile Asn Gln
    370                 375                 380

Tyr Glu Glu Glu Ile Lys Ser Ser Ser Trp Asn Leu Ser Ser Met Arg
385                 390                 395                 400

Tyr Ile Val Asn Gly Gly Glu Ala Val Ile Ser Ser Val Gly Met Lys
                405                 410                 415

Phe Leu Gln Leu Leu Gln Gln His Gln Leu Pro Ser Asn Cys Leu Ile
            420                 425                 430

Pro Thr Phe Gly Met Ser Glu Val Ser Ser Gly Ile Ile Glu Cys His
        435                 440                 445

Ser Phe Tyr Thr Gln Thr Thr Asn Thr Gly Met Leu Tyr Val Asp Lys
    450                 455                 460

Asn Ser Leu Asp Gly Asn Leu Gln Phe Thr Tyr Glu Gly His Gln Asn
465                 470                 475                 480

Ala Ile Val Phe Thr Glu Val Gly Arg Pro Met Pro Gly Ile Gly Ile
                485                 490                 495

Arg Ile Val Asp Glu Asp Asn Gln Cys Leu Ser Glu Asp Arg Ile Gly
            500                 505                 510

Arg Phe Gln Ile His Gly Pro Thr Val Met Asn Gly Tyr Phe Lys Asn
        515                 520                 525

Asp Glu Ala Asn Ala Glu Ser Phe Thr Glu Asp Gly Trp Phe Asp Ser
    530                 535                 540

Gly Asp Leu Gly Phe Ile His Asn Gly Asn Leu Val Ile Thr Gly Arg
545                 550                 555                 560

Lys Lys Asp Met Ile Val Val His Gly Ala Asn Tyr Tyr Asn Tyr Glu
                565                 570                 575

Ile Glu Ala Leu Val Glu Gln Val Pro Gly Val Glu Thr Thr Phe Val
            580                 585                 590

Cys Ala Thr Ser Val Lys Ser Ala Glu Gly Ala Glu Glu Leu Ala Ile
        595                 600                 605

Phe Phe Val Pro Val Ile Asn His Val Ser Val Met Phe Ala Thr Met
    610                 615                 620

Gln Gln Ile Lys Gln Ile Val Ala Arg Lys Met Gly Ile Thr Pro Lys
```

-continued

```
625                 630                 635                 640

Val Ile Ile Pro Ile Gln Lys Glu Ala Phe Phe Lys Thr Asp Ser Gly
                645                 650                 655

Lys Ile Thr Arg Asn Ala Phe Gln Lys Gln Phe Glu Asn Gly Ala Tyr
            660                 665                 670

Arg Glu Ile Thr Gln Lys Ile Asp Cys His Leu Gln Asn Glu Lys Thr
        675                 680                 685

Leu Ser Gln Trp Phe Tyr Arg Glu Lys Leu Val Glu Ser Lys Leu Gly
    690                 695                 700

Lys Ser Val Ser Ser Gln Lys Glu Thr Tyr Val Phe Phe Arg Gln Gly
705                 710                 715                 720

Lys Ser Phe His His Val Leu Lys Glu Lys Leu Thr Gln His Ser Val
                725                 730                 735

Val Ile Val Asp Val Gly Glu Thr Phe Gly Glu Ile His Pro Asn His
            740                 745                 750

Tyr Gln Ile Asn Pro Lys Asn Lys Met Asp Tyr Val Arg Leu Phe Glu
        755                 760                 765

Glu Leu Ala Lys Arg Asn Val Glu Asp Gln Val Phe His Leu Leu His
    770                 775                 780

Ala Trp Asn Tyr Cys Asp Thr Val Pro Thr Phe Arg Ser Val Glu Asp
785                 790                 795                 800

Leu Ala Asn Ala Gln Tyr Leu Gly Val Phe Ser Val Met Phe Ala Leu
                805                 810                 815

Gln Ala Ile Met His Ala Lys Leu Pro Leu Arg Arg Val Thr Val Ile
            820                 825                 830

Ala Thr Asn Ser Val Gly Leu Glu Ala Lys Glu Met Asn Tyr Ser Cys
        835                 840                 845

Ser Thr Leu Glu Gly Tyr Val Lys Thr Leu Pro Ala Glu Phe Glu Asn
    850                 855                 860

Leu Gln Val Lys Tyr Ile Asp Ile Glu Gly Lys Asp Ile Gln Phe Asp
865                 870                 875                 880

Thr Glu Thr Val Trp Lys Glu Leu Gln Gln Glu Thr Ile Pro Val
                885                 890                 895

Val Leu Tyr Arg Asp Glu Lys Arg Tyr Lys Ile Gly Leu Glu Lys Val
            900                 905                 910

Pro Met Leu Glu Gln Lys Glu Lys Asn Ile Pro Phe Gln Gln Gln Gly
        915                 920                 925

Phe Tyr Ile Ile Thr Gly Gly Leu Gly Gly Leu Gly Thr Leu Val Ala
    930                 935                 940

Lys Leu Leu Leu Glu Arg Tyr Ser Ala Asn Val Leu Leu Leu Gly Arg
945                 950                 955                 960

Thr Glu Ile Glu Thr Asn Ala Glu Lys Met Arg Leu Leu Asp Ser Leu
                965                 970                 975

Lys Glu Tyr Glu Gln Tyr Gly Gly Thr Val Gln Tyr Lys Met Cys Asn
            980                 985                 990

Val Met Asp Leu Asp Ala Met Arg  Lys Val Val His Ser  Gln Glu Glu
        995                 1000                1005

Arg Leu  Gln Gln Lys Val Asn  Gly Ile Ile His Leu  Ala Gly Ile
    1010                1015                1020

Ile Gln  Glu Ile Leu Ile Glu  Lys Gln Thr Glu Lys  Glu Leu His
    1025                1030                1035

Ala Met  Phe Glu Ala Lys Val  Tyr Ala Ser Trp Val  Leu His Glu
    1040                1045                1050
```

-continued

```
Ile Val  Lys Glu Arg Gln Asp  Cys Leu Tyr Ile Thr  Thr Ser Ser
    1055                 1060                 1065

Ala Arg  Thr Leu Leu Pro Gly  Met Thr Ile Ser Ala  Tyr Cys Ser
    1070                 1075                 1080

Ala Asn  Arg Phe Val Glu Asn  Phe Ala Tyr Tyr Gln  Arg Ser Gln
    1085                 1090                 1095

Asn Val  Asn Ser Tyr Cys Phe  Ser Trp Ser Phe Trp  Asn Glu Ile
    1100                 1105                 1110

Gly Met  Gly Thr Asn Leu Leu  Ile Lys Asn Ala Leu  Ile Ala Lys
    1115                 1120                 1125

Gly Phe  Gln Leu Ile Asp Asp  Gln Lys Gly Ile Tyr  Ser Leu Leu
    1130                 1135                 1140

Ala Gly  Leu Lys Gly Asn Glu  Pro Asn Val Phe Val  Gly Ile Asn
    1145                 1150                 1155

His Glu  Lys Glu Glu Met Ala  His Leu Ile Gly Thr  Glu Glu Gln
    1160                 1165                 1170

Glu Thr  Gln Gln Leu Thr Ile  Tyr Ile Thr Pro Glu  Tyr Leu His
    1175                 1180                 1185

Ile Leu  Glu Glu Val Phe Ser  Ile Leu Asn Arg Glu  Glu Phe Gly
    1190                 1195                 1200

Gly Leu  Glu Lys Glu Ile Val  Ile Leu Pro Lys Leu  Pro Leu Asp
    1205                 1210                 1215

Glu Tyr  Gly Lys Val Asp Gln  Thr Arg Leu Ala His  Ala Ser Asp
    1220                 1225                 1230

Ser Arg  Phe Gly Lys Lys Gln  His Ile Val Pro Arg  Asn Asp Ile
    1235                 1240                 1245

Glu Glu  Lys Ile Ala Phe Ile  Trp Glu Gly Leu Leu  Asn Lys Lys
    1250                 1255                 1260

Asp Ile  Ser Val Leu Asp His  Phe Phe Glu Leu Gly  Gly Asp Ser
    1265                 1270                 1275

Leu Lys  Ala Thr Gln Met Ile  Ser Ala Leu Lys Lys  Asn Phe Ala
    1280                 1285                 1290

Val Thr  Ile Thr Gln Gln Glu  Phe Phe Gln Ser Ser  Thr Val Glu
    1295                 1300                 1305

Glu Leu  Ala Ser Leu Val Glu  Lys Lys Leu Ser Arg  Thr Arg Thr
    1310                 1315                 1320

His Glu  Met Asp Ile Val Thr  Phe Ser Asp Arg Gly  Asn Val Val
    1325                 1330                 1335

Glu Met  Ser Ser Ala Gln Lys  Arg Gln Trp Phe Leu  Tyr Glu Met
    1340                 1345                 1350

Asp Arg  Glu Asn Pro Tyr Tyr  Asn Asn Thr Leu Val  Ile Arg Leu
    1355                 1360                 1365

Thr Gly  Glu Ile His Leu Pro  Ile Leu Arg Ser Ser  Ile Ile Glu
    1370                 1375                 1380

Leu Val  Asn Lys His Glu Thr  Leu Arg Thr Thr Phe  Val Met Val
    1385                 1390                 1395

Asp Gly  Ile Pro Ser Gln Ile  Ile Ala Asp Glu Glu  Leu Val Glu
    1400                 1405                 1410

Ile Glu  Glu Ile Asp Leu Lys  His Leu Ser Ala Glu  Glu Thr Leu
    1415                 1420                 1425

Gln Lys  Leu Glu Gly Leu Arg  Gln Arg Glu Ala Asn  Thr Ala Phe
    1430                 1435                 1440
```

-continued

```
Lys Ile  Glu Asn Ser Ala Phe  Arg Ala Lys Val Ile  Leu Ile Asp
    1445                 1450                 1455

Glu Lys  Arg Val Glu Ile Leu  Leu Ser Val His His  Ile Val Ser
    1460                 1465                 1470

Asp Gly  Trp Ser Met Gly Ile  Leu Val Lys Asp Ile  Ala Glu Ile
    1475                 1480                 1485

Tyr Glu  Asp Ile Arg Gln Trp  Gly Glu Ser Lys Gln  Glu Pro Leu
    1490                 1495                 1500

Pro Ile  Gln Tyr Ala Asp Tyr  Thr Leu Trp Gln Asn  Glu Phe Met
    1505                 1510                 1515

Lys Gly  Glu Glu Phe Ser Lys  Gln Leu Ser Tyr Trp  Lys Glu Lys
    1520                 1525                 1530

Leu Ala  Glu Asp Ile Pro Val  Leu Asp Leu Pro Leu  Asp Lys Pro
    1535                 1540                 1545

Arg Pro  Pro Ile Gln Thr Tyr  Arg Gly Lys Val Lys  Thr Phe Thr
    1550                 1555                 1560

Leu His  Glu Asn Met Thr Arg  Met Leu Lys Glu Ile  Cys Gln Glu
    1565                 1570                 1575

Glu Glu  Cys Thr Leu Phe Met  Leu Leu Leu Ser Ala  Phe Ser Ser
    1580                 1585                 1590

Leu Leu  His Arg Tyr Thr Gly  Gln Glu Asp Leu Val  Val Gly Ser
    1595                 1600                 1605

Leu Val  Ala Asn Arg Asn Arg  Glu Gln Ile Glu Lys  Leu Ile Gly
    1610                 1615                 1620

Phe Phe  Val Asn Thr Leu Pro  Leu Arg Ile Asn Leu  His Arg Glu
    1625                 1630                 1635

Met Gln  Phe Thr Glu Leu Leu  Ser Gln Val Lys Lys  Thr Thr Ile
    1640                 1645                 1650

Asp Ala  Tyr Asp His Gln Asp  Val Pro Phe Glu Leu  Leu Val Asp
    1655                 1660                 1665

Glu Leu  Gln Ile Glu Arg Asp  Ser Ser Arg Asn Ala  Leu Phe Gln
    1670                 1675                 1680

Val Leu  Phe Val Leu Gln Asn  Ala Gln Leu Gln Ala  Val Asp Leu
    1685                 1690                 1695

Glu Lys  Ala Thr Met Glu Leu  Glu Ile Leu Asp Ser  Asp Thr Ala
    1700                 1705                 1710

Lys Phe  Asp Met Ser Val Gln  Ile Phe Glu Leu Glu  Asp Thr Leu
    1715                 1720                 1725

Ser Ile  Lys Leu Glu Tyr Asn  Thr Asp Leu Phe Phe  Asp Asp Thr
    1730                 1735                 1740

Ile Glu  Arg Phe Leu Ala His  Tyr Glu Thr Ile Leu  Ala Ser Val
    1745                 1750                 1755

Ile His  Asn Gln Lys Ala Lys  Ile Gly Glu Leu Ser  Ile Leu Pro
    1760                 1765                 1770

Gln Ser  Glu Tyr Thr Lys Leu  Val Ser Glu Trp Asn  Glu Lys Ser
    1775                 1780                 1785

Ala Thr  Tyr Asn Gly Asn Gln  Cys Ile His Glu Leu  Phe Glu Ala
    1790                 1795                 1800

Ala Val  His Lys Thr Pro Ser  Ala Thr Ala Leu Ile  Tyr Arg Asn
    1805                 1810                 1815

Lys Glu  Met Thr Tyr Glu Asp  Val Asn Ala Gln Ala  Asn Ala Leu
    1820                 1825                 1830

Ala His  Lys Leu Arg Asp Ala  Gly Val Gly Pro Asn  Gln Val Val
```

-continued

```
    1835                1840                1845

Gly Val  Leu Cys Asp Arg Ser  Phe Glu Met Val Val  Gly Ile Leu
    1850                1855                1860

Ala Val  Leu Lys Ala Gly Gly  Ala Tyr Leu Pro Ile  Asp Thr Ala
    1865                1870                1875

Tyr Pro  Met Gln Arg Thr Glu  Tyr Val Leu Gln Asn  Ser Glu Ala
    1880                1885                1890

Thr Ile  Leu Leu Thr Lys Glu  Cys Tyr Leu Lys Glu  Ser Leu Asp
    1895                1900                1905

Phe Glu  Gly Glu Val Phe Tyr  Leu Asp Asp Ala Arg  Leu Phe Glu
    1910                1915                1920

Gly Asp  Arg Arg Asp Leu Gln  Asn Ile Asn Asn Pro  Thr Asn Leu
    1925                1930                1935

Ala Tyr  Ile Ile Tyr Thr Ser  Gly Ser Thr Gly Asn  Pro Lys Gly
    1940                1945                1950

Val Met  Val Ala His Gln Ser  Val Val Asn Leu Leu  Leu Asp Leu
    1955                1960                1965

Gln Glu  Lys Tyr Pro Val Leu  Ala Glu Asp Lys His  Leu Leu Lys
    1970                1975                1980

Thr Thr  Tyr Thr Phe Asp Val  Ser Val Ala Glu Ile  Phe Gly Trp
    1985                1990                1995

Phe His  Ala Gly Gly Thr Leu  Val Ile Ala Gly His  Gly Asp Glu
    2000                2005                2010

Lys Asp  Pro Glu Lys Leu Ile  Gln Leu Ile Gln Cys  His Lys Val
    2015                2020                2025

Thr His  Ile Asn Phe Val Pro  Ser Met Leu His Ala  Met Leu Gln
    2030                2035                2040

Ala Leu  Asp Glu Lys Asp Phe  Ala Ile Met Asn Arg  Leu Lys Tyr
    2045                2050                2055

Ile Ile  Val Ala Gly Glu Ala  Val Ser Pro Glu Leu  Cys Asn Arg
    2060                2065                2070

Leu Tyr  Ala His Cys Pro Asn  Val Lys Leu Glu Asn  Leu Tyr Gly
    2075                2080                2085

Pro Thr  Glu Gly Thr Ile Tyr  Ala Thr Gly Phe Ser  Ile His Lys
    2090                2095                2100

Glu Met  Asn Val Ala Asn Val  Pro Ile Gly Lys Pro  Leu Ser His
    2105                2110                2115

Val Glu  Thr Tyr Ile Leu Asp  Gln Asn Asn Gln Ile  Val Pro Ile
    2120                2125                2130

Gly Val  Pro Gly Glu Leu Cys  Leu Gly Gly Ile Cys  Val Ala Lys
    2135                2140                2145

Gly Tyr  Met Lys Glu Pro Val  Leu Thr Glu Glu Lys  Phe Val Val
    2150                2155                2160

Asn Pro  Met Lys Gln Ser Glu  Arg Met Tyr Arg Thr  Gly Asp Leu
    2165                2170                2175

Val Arg  Trp Leu Ala Asp Gly  Asn Ile Glu Tyr Leu  Gly Arg Ile
    2180                2185                2190

Asp Asn  Gln Val Lys Ile Arg  Gly Phe Arg Ile Glu  Leu Gly Glu
    2195                2200                2205

Ile Glu  Ala Ala Ile Ala Ala  Leu Glu Asp Val Val  Gln Thr Ile
    2210                2215                2220

Val Thr  Thr Met Thr Asp His  Lys Gly Ala Asn Lys  Ile Val Ala
    2225                2230                2235
```

-continued

```
Tyr Val Val Ser Glu Lys Tyr Asp Glu Glu Arg Ile Arg Glu His
    2240                2245                2250

Val Lys Lys Thr Leu Pro Gln Tyr Met Val Pro Ser Tyr Phe Val
    2255                2260                2265

Ser Met Lys Ala Leu Pro Leu Asn Lys Asn Gly Lys Val Asp Arg
    2270                2275                2280

Lys Gln Leu His Ser Val Asp Leu Tyr Glu Thr Ser Met Asp Thr
    2285                2290                2295

Val Ile Val Gly Pro Arg Asn Glu Lys Glu Ala Met Leu Ser Val
    2300                2305                2310

Ile Trp Gln Glu Leu Leu Gly Leu Glu Asn Ile Ser Val His Asp
    2315                2320                2325

Asn Phe Phe Lys Leu Gly Gly His Ser Ile Asn Ala Thr Gln Leu
    2330                2335                2340

Val Ser Lys Ile Tyr Ser Val Cys Arg Val Arg Met Pro Leu Lys
    2345                2350                2355

Asn Val Phe Gln Tyr Thr Thr Leu Ala Thr Met Ala Arg Val Leu
    2360                2365                2370

Glu Glu Leu Leu Val Ser Ala Val Asp Glu Val Ala Val Thr Thr
    2375                2380                2385

Glu Arg Ile Pro Lys Ile Leu Pro Arg Thr Tyr Tyr Asp Leu Ser
    2390                2395                2400

Tyr Ser Gln Gln Arg Ile Tyr Phe Leu Ser Thr Met Glu Lys Glu
    2405                2410                2415

Thr Asn Tyr Tyr Asn Ile Leu Gly Ala Trp Asp Ile Tyr Gly Lys
    2420                2425                2430

Leu Asp Val Thr Leu Phe Glu Lys Ala Ile Gln Leu Leu Met Lys
    2435                2440                2445

Lys His His Ser Leu Arg Ala Thr Phe Glu Ile Val Asp Gly Lys
    2450                2455                2460

Pro Val Gln Ile Ile His Asp Asp Met Glu Ile Pro Val Gln Phe
    2465                2470                2475

Ile Asp Leu Thr Val Met Pro Glu Gly Leu Arg Ile Glu Glu Val
    2480                2485                2490

Asp Glu Leu Met Leu Lys Glu Ser Lys Arg Val Tyr Asn Leu Ala
    2495                2500                2505

Asn Gly Pro Leu Met His Cys Thr Ile Val Lys Ile Lys Glu Gly
    2510                2515                2520

Glu His Val Leu Leu Ile Gly Gln His His Ile Ile Ser Asp Gly
    2525                2530                2535

Trp Ser Leu Gly Ile Phe Val Lys Glu Leu Asn Glu Met Tyr Asp
    2540                2545                2550

Ala Phe Val Gln His Lys Pro Val Ala Glu Thr Pro Ser Thr Ile
    2555                2560                2565

Ser Ile Met Asp Phe Thr Ala Trp His Asn Ser Lys Val Asp Glu
    2570                2575                2580

Asp Gln Asp Asp Arg Gln Tyr Trp Leu Gln Arg Phe Glu Gly Glu
    2585                2590                2595

Leu Pro Thr Leu Glu Leu Pro Thr Asp Arg Gln Arg Pro Leu Leu
    2600                2605                2610

Lys Thr Tyr His Gly Asp Thr Leu Ser Tyr Lys Val Asn Ser Gln
    2615                2620                2625
```

-continued

```
Leu His Gln Lys Leu Lys Asp Phe Ser His Ala Asn Gly Val Thr
    2630                2635                2640

Met Phe Met Thr Leu Leu Thr Ala Tyr Asn Ile Met Leu Asn Lys
    2645                2650                2655

Leu Thr Asn Glu Thr Asp Ile Val Val Gly Ser Pro Val Ala Gly
    2660                2665                2670

Arg Asn Glu Pro Glu Ser Lys Asp Leu Ile Gly Met Phe Val Asn
    2675                2680                2685

Thr Leu Ala Leu Arg Ser His Leu Gly Asp Asn Pro Thr Val Asp
    2690                2695                2700

Val Leu Leu Lys Gln Ile Lys Gln Asn Thr Leu Glu Ala Tyr Asn
    2705                2710                2715

His Gln Asp Tyr Pro Phe Asp Lys Leu Val Asp Asp Leu Asp Pro
    2720                2725                2730

His Arg Asp Leu Ser Arg Thr Pro Ile Phe Gln Val Met Met Gly
    2735                2740                2745

Tyr Met Asn Met Pro Leu Met Val Ala Phe Arg Glu Ala Glu Val
    2750                2755                2760

Arg Glu Arg Phe Val Arg His Lys Val Ala Arg Phe Asp Leu Thr
    2765                2770                2775

Leu His Val Phe Glu Asp Glu Asp Gln Met Lys Ile Phe Phe Glu
    2780                2785                2790

Tyr Asn Thr Asp Leu Phe Asp Glu Ser Thr Ile Met Arg Trp Gln
    2795                2800                2805

Asn His Phe Glu Thr Leu Leu Gln Glu Ile Val Ser Asn Pro Thr
    2810                2815                2820

Lys Arg Ile Ser Glu Leu Asn Ile Leu Thr Asn Glu Glu Lys Tyr
    2825                2830                2835

Glu Ile Leu Glu Met Asn Asn Asn Ser Thr Glu Tyr Pro Gln His
    2840                2845                2850

Glu Ser Val Ala Glu Ile Phe Arg Glu Thr Lys Ile Lys His Gln
    2855                2860                2865

Ala Lys Leu Ala Ile Thr Tyr Lys Asp Arg Lys Leu Thr Tyr Ala
    2870                2875                2880

Glu Leu Ser Glu Lys Ala Asn Ala Leu Ala His Thr Leu Lys Arg
    2885                2890                2895

Arg Gly Val Ala Gln His Asp Val Val Gly Ile Val Ala Glu Arg
    2900                2905                2910

Ser Pro Glu Thr Ile Ile Gly Ile Leu Ala Ile Leu Lys Val Gly
    2915                2920                2925

Ala Ile Tyr Leu Pro Ile Asp Pro Lys Leu Pro Gln Leu Thr Leu
    2930                2935                2940

Gln His Ile Trp Arg Asp Ser Gly Ala Lys Val Leu Leu Gly Lys
    2945                2950                2955

Asn Glu Thr Thr Val Glu Val Gly Lys Glu Val Pro Phe Val Asp
    2960                2965                2970

Ile Glu Gly Asp Lys Gly Lys Gln Glu Glu Leu Val Cys Pro Ile
    2975                2980                2985

Ser Pro Glu Asp Thr Ala Tyr Ile Met Tyr Thr Ser Gly Ser Thr
    2990                2995                3000

Gly Lys Pro Lys Gly Val Met Val Thr His Arg Asn Ile Val Arg
    3005                3010                3015

Leu Val Lys Asn Thr Asn Phe Val Ser Leu Gln Glu Gln Asp Val
```

-continued

```
    3020                3025                3030

Leu Leu  Gln Thr Gly Ser Leu  Thr Phe Asp Ala Ala  Thr Phe Glu
    3035                3040                3045

Ile Trp  Gly Ala Leu Leu Asn  Gly Leu Thr Leu His  Leu Val Glu
    3050                3055                3060

Asp Tyr  Val Ile Leu Asp Gly  Glu Ala Leu Gln Glu  Glu Ile Gln
    3065                3070                3075

Gln Asn  Lys Ala Thr Ile Met  Trp Val Ser Ala Pro  Leu Phe Asn
    3080                3085                3090

Gln Leu  Ala Asp Gln Asn Pro  Ala Met Phe Thr Gly  Ile Lys Gln
    3095                3100                3105

Leu Leu  Ile Gly Gly Asp Val  Leu Ser Pro Lys His  Ile Asn Lys
    3110                3115                3120

Val Met  Asp His Cys Ala Pro  Ile Asn Ile Ile Asn  Gly Tyr Gly
    3125                3130                3135

Pro Thr  Glu Asn Thr Thr Phe  Ser Thr Ser Phe Val  Ile Asp Gln
    3140                3145                3150

Met Tyr  Gln Asp Ser Ile Pro  Ile Gly Thr Pro Ile  Ala Asn Ser
    3155                3160                3165

Ser Ala  Tyr Ile Leu Asp Val  His Gln Asn Ile Gln  Pro Ile Gly
    3170                3175                3180

Val Val  Gly Glu Leu Cys Val  Gly Gly Asp Gly Val  Ala Lys Gly
    3185                3190                3195

Tyr Val  Asn Leu Glu Gln Leu  Thr Glu Glu Arg Phe  Ile Ala Asp
    3200                3205                3210

Pro Phe  Leu Lys Gly Ser Thr  Met Tyr Arg Thr Gly  Asp Tyr Val
    3215                3220                3225

Lys Leu  Leu Pro Asn Gly Asn  Ile Gln Tyr Ile Gly  Arg Val Asp
    3230                3235                3240

Asn Gln  Val Lys Ile Arg Gly  Phe Arg Ile Glu Leu  Glu Ala Ile
    3245                3250                3255

Met Asn  Thr Leu Lys Gln Cys  Glu Ser Ile Lys Asp  Val Ile Val
    3260                3265                3270

Val Val  Gln Glu Gln Asn Gly  Tyr Lys Thr Leu Val  Ala Tyr Val
    3275                3280                3285

Val Gly  Glu Glu Ser Leu Ser  Ile Glu Thr Val Arg  Ala Tyr Ala
    3290                3295                3300

Lys Lys  His Leu Ala Glu Tyr  Met Val Pro Ser Gln  Phe Ile Phe
    3305                3310                3315

Ile Glu  Glu Ile Pro Leu Ser  Ile Asn Gly Lys Val  Gln Tyr Ser
    3320                3325                3330

Lys Leu  Pro Lys Val Gln Glu  Val Leu His Lys Lys  Val Glu Thr
    3335                3340                3345

Leu Leu  Pro Glu Asn Arg Leu  Glu Glu Ile Ile Leu  Arg Val Tyr
    3350                3355                3360

Arg Asp  Val Leu Glu Lys Glu  Asp Phe Gly Val Thr  Asp Ser Phe
    3365                3370                3375

Phe Ala  Tyr Gly Gly Asp Ser  Leu Leu Ser Ile Gln  Val Val Ser
    3380                3385                3390

Met Leu  Lys Lys Glu Glu Ile  Ala Val Asp Pro Lys  Met Ile Phe
    3395                3400                3405

Met His  Thr Thr Val Arg Glu  Leu Ala Lys Ala Cys  Glu Asn Arg
    3410                3415                3420
```

-continued

```
Pro Val  Met Glu Glu Thr Lys  Arg Thr Glu Lys Asp  Tyr Leu Ile
    3425                3430                3435

Gln Met  Arg Glu Gly Ser Glu  Glu Asp Ser Cys Ile  Ile Phe Ala
    3440                3445                3450

Pro Pro  Ala Gly Gly Thr Val  Leu Gly Tyr Ile Glu  Leu Ala Arg
    3455                3460                3465

Tyr Phe  Glu Gly Ile Gly Asn  Val Tyr Gly Leu Gln  Ala Pro Gly
    3470                3475                3480

Leu Tyr  Asp Asp Glu Glu Pro  Thr Phe Leu Asp Tyr  Asp Glu Leu
    3485                3490                3495

Val Gln  Val Phe Leu Arg Ser  Ile Glu Gly Thr Tyr  Arg Pro Gly
    3500                3505                3510

Gln Asp  Tyr Leu Gly Gly His  Ser Leu Gly Gly His  Ile Ala Phe
    3515                3520                3525

Gly Met  Cys Cys Glu Leu Ile  Lys Gln Gly Lys Ala  Pro Lys Gly
    3530                3535                3540

Leu Leu  Ile Leu Asp Thr Thr  Pro Ser Leu Gln Val  Val Lys Gly
    3545                3550                3555

Ala Lys  Asp Glu Lys Ile Ala  Glu Glu Asp Phe Lys  Met Met Val
    3560                3565                3570

Leu Ala  Ala Gly Ile Gly Asn  Met Met Gly Val Asp  Pro Glu Glu
    3575                3580                3585

Leu Lys  Gln Leu Ser Tyr Glu  Glu Ala Lys Thr Arg  Val Val Ala
    3590                3595                3600

Val Ala  Gln Lys Asp Glu Lys  Leu Lys Thr Phe Ile  Asn Glu Thr
    3605                3610                3615

Tyr Leu  Asp Lys Tyr Leu Lys  Leu Gln Ile His Ser  Leu Leu Met
    3620                3625                3630

Ser Arg  Thr Leu Glu Leu Glu  Lys Thr Gln Leu Asp  Ile Pro Ile
    3635                3640                3645

Lys Val  Phe Lys Thr Gln Phe  His Thr Glu Glu Leu  Val Glu Arg
    3650                3655                3660

Phe Asp  Ala Trp His Asn Tyr  Thr Asn Gln Ala Cys  Thr Phe Ile
    3665                3670                3675

Asp Ile  Pro Gly Thr His Thr  Thr Met Met Arg Leu  Pro His Val
    3680                3685                3690

Lys Glu  Val Ala Lys Lys Ile  Glu Glu Gln Leu
    3695                3700


<210> SEQ ID NO 2
<211> LENGTH: 1804
<212> TYPE: PRT
<213> ORGANISM: Bacillus cereus

<400> SEQUENCE: 2

Phe Ile Lys Ser Met Asn Gln Leu Gly Lys Ser Lys Asn Leu His Asn
1               5                   10                  15

Gly Gly Met Met Glu Met Lys Arg Val Glu Glu His Asp His Ile His
            20                  25                  30

Val Leu Asn Glu Ile Glu Asn Glu Cys Glu Arg Arg Tyr Gly Arg Ser
        35                  40                  45

Asn Ile Ala Ile Met Leu Glu Lys His Gly Val His Glu Gln Pro Leu
    50                  55                  60

His Ile Glu Asp Leu Phe His Glu Val Glu Met Gln Glu His Ser Arg
```

-continued

```
65                  70                  75                  80

Val Ser Arg His Glu Thr Val Leu Met Thr Asp Lys Gln Cys Ile Asp
                85                  90                  95

Glu Ser Gly Lys Pro Leu Ala Leu Arg Phe Gly Glu Pro Leu His Leu
            100                 105                 110

Asp Asp Cys Thr Pro Lys Thr Leu Gln Glu Ile Leu Lys Arg Ala Ala
        115                 120                 125

Lys Gln Ala Lys Asp Lys Gly Met Thr Phe Val Tyr Glu Asp Gly His
    130                 135                 140

Glu Glu Tyr Leu Ser Tyr Gln Glu Met Leu Ala Asp Ala Glu Arg Leu
145                 150                 155                 160

Leu Lys Gly Leu Arg Asn Leu Gly Ile Gln Pro Gly Glu Ser Ile Leu
                165                 170                 175

Phe Gln Phe Lys Asp Asn Lys His Phe Val Thr Ala Phe Trp Ala Cys
            180                 185                 190

Ile Leu Gly Gly Phe Leu Pro Thr Pro Leu Gly Thr Ala Pro Ile Tyr
        195                 200                 205

Ser Glu Gln Asn Ala Gln Val Leu Lys Leu Tyr Asn Thr Trp Gln Leu
    210                 215                 220

Leu Glu Gln Pro Ile Ile Leu Thr Glu Phe Glu Leu Lys Glu Glu Ile
225                 230                 235                 240

Ala Ala Ile Arg Thr Thr Leu Gln Arg Gln Glu Ile Val Ile His Ser
                245                 250                 255

Ile Glu Asn Val Met Asp Thr Ala Arg Asp Thr Asn Trp Phe Pro Cys
            260                 265                 270

Thr Glu Asp Thr Ile Val Leu Asn Leu Leu Thr Ser Gly Ser Thr Gly
        275                 280                 285

Val Pro Lys Cys Val Gln His Lys Ser Lys Ser Ile Ile Ala Arg Thr
    290                 295                 300

Val Ser Asn Cys Ile Asp Arg Gln Leu Asp Glu Lys Glu Val Ser Leu
305                 310                 315                 320

Asn Trp Met Pro Leu Asp His Val Gly Gly Ile Val Met Cys His Ile
                325                 330                 335

Arg Asp Thr Tyr Leu Met Cys Gln Gln Val Asn Cys Leu Ile Ser Ala
            340                 345                 350

Phe Ile Glu Asn Pro Leu Asn Trp Leu His Trp Ile Asp Ala Tyr Ser
        355                 360                 365

Ala Thr Phe Thr Trp Ala Pro Asn Phe Ala Phe Ser Leu Ile Asn Gln
    370                 375                 380

Tyr Glu Glu Glu Ile Lys Ser Ser Ser Trp Asn Leu Ser Ser Met Arg
385                 390                 395                 400

Tyr Ile Val Asn Gly Gly Glu Ala Val Ile Ser Ser Val Gly Met Lys
                405                 410                 415

Phe Leu Gln Leu Leu Gln Gln His Gln Leu Pro Ser Asn Cys Leu Ile
            420                 425                 430

Pro Thr Phe Gly Met Ser Glu Val Ser Ser Gly Ile Ile Glu Cys His
        435                 440                 445

Ser Phe Tyr Thr Gln Thr Thr Asn Thr Gly Met Leu Tyr Val Asp Lys
    450                 455                 460

Asn Ser Leu Asp Gly Asn Leu Gln Phe Thr Tyr Glu Gly His Gln Asn
465                 470                 475                 480

Ala Ile Val Phe Thr Glu Val Gly Arg Pro Met Pro Gly Ile Gly Ile
                485                 490                 495
```

```
Arg Ile Val Asp Glu Asp Asn Gln Cys Leu Ser Glu Asp Arg Ile Gly
            500                 505                 510

Arg Phe Gln Ile His Gly Pro Thr Val Met Asn Gly Tyr Phe Lys Asn
        515                 520                 525

Asp Glu Ala Asn Ala Glu Ser Phe Thr Glu Asp Gly Trp Phe Asp Ser
    530                 535                 540

Gly Asp Leu Gly Phe Ile His Asn Gly Asn Leu Val Ile Thr Gly Arg
545                 550                 555                 560

Lys Lys Asp Met Ile Val Val His Gly Ala Asn Tyr Tyr Asn Tyr Glu
                565                 570                 575

Ile Glu Ala Leu Val Glu Gln Val Pro Gly Val Glu Thr Thr Phe Val
            580                 585                 590

Cys Ala Thr Ser Val Lys Ser Ala Glu Gly Ala Glu Glu Leu Ala Ile
        595                 600                 605

Phe Phe Val Pro Val Ile Asn His Val Ser Val Met Phe Ala Thr Met
    610                 615                 620

Gln Gln Ile Lys Gln Ile Val Ala Arg Lys Met Gly Ile Thr Pro Lys
625                 630                 635                 640

Val Ile Ile Pro Ile Gln Lys Glu Ala Phe Phe Lys Thr Asp Ser Gly
                645                 650                 655

Lys Ile Thr Arg Asn Ala Phe Gln Lys Gln Phe Glu Asn Gly Ala Tyr
            660                 665                 670

Arg Glu Ile Thr Gln Lys Ile Asp Cys His Leu Gln Asn Glu Lys Thr
        675                 680                 685

Leu Ser Gln Trp Phe Tyr Arg Glu Lys Leu Val Glu Ser Lys Leu Gly
    690                 695                 700

Lys Ser Val Ser Ser Gln Lys Glu Thr Tyr Val Phe Phe Arg Gln Gly
705                 710                 715                 720

Lys Ser Phe His His Val Leu Lys Glu Lys Leu Thr Gln His Ser Val
                725                 730                 735

Val Ile Val Asp Val Gly Glu Thr Phe Gly Glu Ile His Pro Asn His
            740                 745                 750

Tyr Gln Ile Asn Pro Lys Asn Lys Met Asp Tyr Val Arg Leu Phe Glu
        755                 760                 765

Glu Leu Ala Lys Arg Asn Val Glu Asp Gln Val Phe His Leu Leu His
    770                 775                 780

Ala Trp Asn Tyr Cys Asp Thr Val Pro Thr Phe Arg Ser Val Glu Asp
785                 790                 795                 800

Leu Ala Asn Ala Gln Tyr Leu Gly Val Phe Ser Val Met Phe Ala Leu
                805                 810                 815

Gln Ala Ile Met His Ala Lys Leu Pro Leu Arg Arg Val Thr Val Ile
            820                 825                 830

Ala Thr Asn Ser Val Gly Leu Glu Ala Lys Glu Met Asn Tyr Ser Cys
        835                 840                 845

Ser Thr Leu Glu Gly Tyr Val Lys Thr Leu Pro Ala Glu Phe Glu Asn
    850                 855                 860

Leu Gln Val Lys Tyr Ile Asp Ile Glu Gly Lys Asp Ile Gln Phe Asp
865                 870                 875                 880

Thr Glu Thr Val Trp Lys Glu Leu Gln Gln Gln Glu Thr Ile Pro Val
                885                 890                 895

Val Leu Tyr Arg Asp Glu Lys Arg Tyr Lys Ile Gly Leu Glu Lys Val
            900                 905                 910
```

-continued

```
Pro Met Leu Glu Gln Lys Glu Lys Asn Ile Pro Phe Gln Gln Gln Gly
        915                 920                 925

Phe Tyr Ile Ile Thr Gly Gly Leu Gly Gly Leu Gly Thr Leu Val Ala
    930                 935                 940

Lys Leu Leu Leu Glu Arg Tyr Ser Ala Asn Val Leu Leu Leu Gly Arg
945                 950                 955                 960

Thr Glu Ile Glu Thr Asn Ala Glu Lys Met Arg Leu Leu Asp Ser Leu
                965                 970                 975

Lys Glu Tyr Glu Gln Tyr Gly Gly Thr Val Gln Tyr Lys Met Cys Asn
            980                 985                 990

Val Met Asp Leu Asp Ala Met Arg  Lys Val Val His Ser  Gln Glu Glu
        995                 1000                 1005

Arg Leu  Gln Gln Lys Val Asn  Gly Ile Ile His Leu  Ala Gly Ile
    1010                 1015                 1020

Ile Gln  Glu Ile Leu Ile Glu  Lys Gln Thr Glu Lys  Glu Leu His
    1025                 1030                 1035

Ala Met  Phe Glu Ala Lys Val  Tyr Ala Ser Trp Val  Leu His Glu
    1040                 1045                 1050

Ile Val  Lys Glu Arg Gln Asp  Cys Leu Tyr Ile Thr  Thr Ser Ser
    1055                 1060                 1065

Ala Arg  Thr Leu Leu Pro Gly  Met Thr Ile Ser Ala  Tyr Cys Ser
    1070                 1075                 1080

Ala Asn  Arg Phe Val Glu Asn  Phe Ala Tyr Tyr Gln  Arg Ser Gln
    1085                 1090                 1095

Asn Val  Asn Ser Tyr Cys Phe  Ser Trp Ser Phe Trp  Asn Glu Ile
    1100                 1105                 1110

Gly Met  Gly Thr Asn Leu Leu  Ile Lys Asn Ala Leu  Ile Ala Lys
    1115                 1120                 1125

Gly Phe  Gln Leu Ile Asp Asp  Gln Lys Gly Ile Tyr  Ser Leu Leu
    1130                 1135                 1140

Ala Gly  Leu Lys Gly Asn Glu  Pro Asn Val Phe Val  Gly Ile Asn
    1145                 1150                 1155

His Glu  Lys Glu Glu Met Ala  His Leu Ile Gly Thr  Glu Glu Gln
    1160                 1165                 1170

Glu Thr  Gln Gln Leu Thr Ile  Tyr Ile Thr Pro Glu  Tyr Leu His
    1175                 1180                 1185

Ile Leu  Glu Glu Val Phe Ser  Ile Leu Asn Arg Glu  Glu Phe Gly
    1190                 1195                 1200

Gly Leu  Glu Lys Glu Ile Val  Ile Leu Pro Lys Leu  Pro Leu Asp
    1205                 1210                 1215

Glu Tyr  Gly Lys Val Asp Gln  Thr Arg Leu Ala His  Ala Ser Asp
    1220                 1225                 1230

Ser Arg  Phe Gly Lys Lys Gln  His Ile Val Pro Arg  Asn Asp Ile
    1235                 1240                 1245

Glu Glu  Lys Ile Ala Phe Ile  Trp Glu Gly Leu Leu  Asn Lys Lys
    1250                 1255                 1260

Asp Ile  Ser Val Leu Asp His  Phe Phe Glu Leu Gly  Gly Asp Ser
    1265                 1270                 1275

Leu Lys  Ala Thr Gln Met Ile  Ser Ala Leu Lys Lys  Asn Phe Ala
    1280                 1285                 1290

Val Thr  Ile Thr Gln Gln Glu  Phe Phe Gln Ser Ser  Thr Val Glu
    1295                 1300                 1305

Glu Leu  Ala Ser Leu Val Glu  Lys Lys Leu Ser Arg  Thr Arg Thr
```

-continued

```
    1310                1315                1320

His Glu  Met Asp Ile Val Thr  Phe Ser Asp Arg Gly  Asn Val Val
    1325                1330                1335

Glu Met  Ser Ser Ala Gln Lys  Arg Gln Trp Phe Leu  Tyr Glu Met
    1340                1345                1350

Asp Arg  Glu Asn Pro Tyr Tyr  Asn Asn Thr Leu Val  Ile Arg Leu
    1355                1360                1365

Thr Gly  Glu Ile His Leu Pro  Ile Leu Arg Ser Ser  Ile Ile Glu
    1370                1375                1380

Leu Val  Asn Lys His Glu Thr  Leu Arg Thr Thr Phe  Val Met Val
    1385                1390                1395

Asp Gly  Ile Pro Ser Gln Ile  Ile Ala Asp Glu Glu  Leu Val Glu
    1400                1405                1410

Ile Glu  Glu Ile Asp Leu Lys  His Leu Ser Ala Glu  Glu Thr Leu
    1415                1420                1425

Gln Lys  Leu Glu Gly Leu Arg  Gln Arg Glu Ala Asn  Thr Ala Phe
    1430                1435                1440

Lys Ile  Glu Asn Ser Ala Phe  Arg Ala Lys Val Ile  Leu Ile Asp
    1445                1450                1455

Glu Lys  Arg Val Glu Ile Leu  Leu Ser Val His His  Ile Val Ser
    1460                1465                1470

Asp Gly  Trp Ser Met Gly Ile  Leu Val Lys Asp Ile  Ala Glu Ile
    1475                1480                1485

Tyr Glu  Asp Ile Arg Gln Trp  Gly Glu Ser Lys Gln  Glu Pro Leu
    1490                1495                1500

Pro Ile  Gln Tyr Ala Asp Tyr  Thr Leu Trp Gln Asn  Glu Phe Met
    1505                1510                1515

Lys Gly  Glu Glu Phe Ser Lys  Gln Leu Ser Tyr Trp  Lys Glu Lys
    1520                1525                1530

Leu Ala  Glu Asp Ile Pro Val  Leu Asp Leu Pro Leu  Asp Lys Pro
    1535                1540                1545

Arg Pro  Pro Ile Gln Thr Tyr  Arg Gly Lys Val Lys  Thr Phe Thr
    1550                1555                1560

Leu His  Glu Asn Met Thr Arg  Met Leu Lys Glu Ile  Cys Gln Glu
    1565                1570                1575

Glu Glu  Cys Thr Leu Phe Met  Leu Leu Leu Ser Ala  Phe Ser Ser
    1580                1585                1590

Leu Leu  His Arg Tyr Thr Gly  Gln Glu Asp Leu Val  Val Gly Ser
    1595                1600                1605

Leu Val  Ala Asn Arg Asn Arg  Glu Gln Ile Glu Lys  Leu Ile Gly
    1610                1615                1620

Phe Phe  Val Asn Thr Leu Pro  Leu Arg Ile Asn Leu  His Arg Glu
    1625                1630                1635

Met Gln  Phe Thr Glu Leu Leu  Ser Gln Val Lys Lys  Thr Thr Ile
    1640                1645                1650

Asp Ala  Tyr Asp His Gln Asp  Val Pro Phe Glu Leu  Leu Val Asp
    1655                1660                1665

Glu Leu  Gln Ile Glu Arg Asp  Ser Ser Arg Asn Ala  Leu Phe Gln
    1670                1675                1680

Val Leu  Phe Val Leu Gln Asn  Ala Gln Leu Gln Ala  Val Asp Leu
    1685                1690                1695

Glu Lys  Ala Thr Met Glu Leu  Glu Ile Leu Asp Ser  Asp Thr Ala
    1700                1705                1710
```

```
Lys Phe  Asp Met Ser Val Gln  Ile Phe Glu Leu Glu  Asp Thr Leu
    1715                 1720                 1725

Ser Ile  Lys Leu Glu Tyr Asn  Thr Asp Leu Phe Phe  Asp Asp Thr
    1730                 1735                 1740

Ile Glu  Arg Phe Leu Ala His  Tyr Glu Thr Ile Leu  Ala Ser Val
    1745                 1750                 1755

Ile His  Asn Gln Lys Ala Lys  Ile Gly Glu Leu Ser  Ile Leu Pro
    1760                 1765                 1770

Gln Ser  Glu Tyr Thr Lys Leu  Val Ser Glu Trp Asn  Glu Lys Ser
    1775                 1780                 1785

Ala Thr  Tyr Asn Gly Asn Gln  Cys Ile His Glu Leu  Phe Glu Ala
    1790                 1795                 1800

Ala


<210> SEQ ID NO 3
<211> LENGTH: 1900
<212> TYPE: PRT
<213> ORGANISM: Bacillus cereus

<400> SEQUENCE: 3

Val His Lys Thr Pro Ser Ala Thr Ala Leu Ile Tyr Arg Asn Lys Glu
1               5                   10                  15

Met Thr Tyr Glu Asp Val Asn Ala Gln Ala Asn Ala Leu Ala His Lys
            20                  25                  30

Leu Arg Asp Ala Gly Val Gly Pro Asn Gln Val Val Gly Val Leu Cys
        35                  40                  45

Asp Arg Ser Phe Glu Met Val Val Gly Ile Leu Ala Val Leu Lys Ala
    50                  55                  60

Gly Gly Ala Tyr Leu Pro Ile Asp Thr Ala Tyr Pro Met Gln Arg Thr
65                  70                  75                  80

Glu Tyr Val Leu Gln Asn Ser Glu Ala Thr Ile Leu Leu Thr Lys Glu
                85                  90                  95

Cys Tyr Leu Lys Glu Ser Leu Asp Phe Glu Gly Glu Val Phe Tyr Leu
            100                 105                 110

Asp Asp Ala Arg Leu Phe Glu Gly Asp Arg Arg Asp Leu Gln Asn Ile
        115                 120                 125

Asn Asn Pro Thr Asn Leu Ala Tyr Ile Ile Tyr Thr Ser Gly Ser Thr
    130                 135                 140

Gly Asn Pro Lys Gly Val Met Val Ala His Gln Ser Val Val Asn Leu
145                 150                 155                 160

Leu Leu Asp Leu Gln Glu Lys Tyr Pro Val Leu Ala Glu Asp Lys His
                165                 170                 175

Leu Leu Lys Thr Thr Tyr Thr Phe Asp Val Ser Val Ala Glu Ile Phe
            180                 185                 190

Gly Trp Phe His Ala Gly Gly Thr Leu Val Ile Ala Gly His Gly Asp
        195                 200                 205

Glu Lys Asp Pro Glu Lys Leu Ile Gln Leu Ile Gln Cys His Lys Val
    210                 215                 220

Thr His Ile Asn Phe Val Pro Ser Met Leu His Ala Met Leu Gln Ala
225                 230                 235                 240

Leu Asp Glu Lys Asp Phe Ala Ile Met Asn Arg Leu Lys Tyr Ile Ile
                245                 250                 255

Val Ala Gly Glu Ala Val Ser Pro Glu Leu Cys Asn Arg Leu Tyr Ala
            260                 265                 270
```

-continued

```
His Cys Pro Asn Val Lys Leu Glu Asn Leu Tyr Gly Pro Thr Glu Gly
        275                 280                 285

Thr Ile Tyr Ala Thr Gly Phe Ser Ile His Lys Glu Met Asn Val Ala
    290                 295                 300

Asn Val Pro Ile Gly Lys Pro Leu Ser His Val Glu Thr Tyr Ile Leu
305                 310                 315                 320

Asp Gln Asn Asn Gln Ile Val Pro Ile Gly Val Pro Gly Glu Leu Cys
                325                 330                 335

Leu Gly Gly Ile Cys Val Ala Lys Gly Tyr Met Lys Glu Pro Val Leu
            340                 345                 350

Thr Glu Glu Lys Phe Val Val Asn Pro Met Lys Gln Ser Glu Arg Met
        355                 360                 365

Tyr Arg Thr Gly Asp Leu Val Arg Trp Leu Ala Asp Gly Asn Ile Glu
    370                 375                 380

Tyr Leu Gly Arg Ile Asp Asn Gln Val Lys Ile Arg Gly Phe Arg Ile
385                 390                 395                 400

Glu Leu Gly Glu Ile Glu Ala Ala Ile Ala Ala Leu Glu Asp Val Val
                405                 410                 415

Gln Thr Ile Val Thr Thr Met Thr Asp His Lys Gly Ala Asn Lys Ile
            420                 425                 430

Val Ala Tyr Val Val Ser Glu Lys Tyr Asp Glu Glu Arg Ile Arg Glu
        435                 440                 445

His Val Lys Lys Thr Leu Pro Gln Tyr Met Val Pro Ser Tyr Phe Val
    450                 455                 460

Ser Met Lys Ala Leu Pro Leu Asn Lys Asn Gly Lys Val Asp Arg Lys
465                 470                 475                 480

Gln Leu His Ser Val Asp Leu Tyr Glu Thr Ser Met Asp Thr Val Ile
                485                 490                 495

Val Gly Pro Arg Asn Glu Lys Glu Ala Met Leu Ser Val Ile Trp Gln
            500                 505                 510

Glu Leu Leu Gly Leu Glu Asn Ile Ser Val His Asp Asn Phe Phe Lys
        515                 520                 525

Leu Gly Gly His Ser Ile Asn Ala Thr Gln Leu Val Ser Lys Ile Tyr
    530                 535                 540

Ser Val Cys Arg Val Arg Met Pro Leu Lys Asn Val Phe Gln Tyr Thr
545                 550                 555                 560

Thr Leu Ala Thr Met Ala Arg Val Leu Glu Glu Leu Leu Val Ser Ala
                565                 570                 575

Val Asp Glu Val Ala Val Thr Thr Glu Arg Ile Pro Lys Ile Leu Pro
            580                 585                 590

Arg Thr Tyr Tyr Asp Leu Ser Tyr Ser Gln Gln Arg Ile Tyr Phe Leu
        595                 600                 605

Ser Thr Met Glu Lys Glu Thr Asn Tyr Tyr Asn Ile Leu Gly Ala Trp
    610                 615                 620

Asp Ile Tyr Gly Lys Leu Asp Val Thr Leu Phe Glu Lys Ala Ile Gln
625                 630                 635                 640

Leu Leu Met Lys Lys His His Ser Leu Arg Ala Thr Phe Glu Ile Val
                645                 650                 655

Asp Gly Lys Pro Val Gln Ile Ile His Asp Asp Met Glu Ile Pro Val
            660                 665                 670

Gln Phe Ile Asp Leu Thr Val Met Pro Glu Gly Leu Arg Ile Glu Glu
        675                 680                 685
```

-continued

```
Val Asp Glu Leu Met Leu Lys Glu Ser Lys Arg Val Tyr Asn Leu Ala
    690                 695                 700

Asn Gly Pro Leu Met His Cys Thr Ile Val Lys Ile Lys Glu Gly Glu
705                 710                 715                 720

His Val Leu Leu Ile Gly Gln His His Ile Ile Ser Asp Gly Trp Ser
                725                 730                 735

Leu Gly Ile Phe Val Lys Glu Leu Asn Glu Met Tyr Asp Ala Phe Val
            740                 745                 750

Gln His Lys Pro Val Ala Glu Thr Pro Ser Thr Ile Ser Ile Met Asp
        755                 760                 765

Phe Thr Ala Trp His Asn Ser Lys Val Asp Glu Asp Gln Asp Asp Arg
    770                 775                 780

Gln Tyr Trp Leu Gln Arg Phe Glu Gly Glu Leu Pro Thr Leu Glu Leu
785                 790                 795                 800

Pro Thr Asp Arg Gln Arg Pro Leu Leu Lys Thr Tyr His Gly Asp Thr
                805                 810                 815

Leu Ser Tyr Lys Val Asn Ser Gln Leu His Gln Lys Leu Lys Asp Phe
            820                 825                 830

Ser His Ala Asn Gly Val Thr Met Phe Met Thr Leu Leu Thr Ala Tyr
        835                 840                 845

Asn Ile Met Leu Asn Lys Leu Thr Asn Glu Thr Asp Ile Val Val Gly
    850                 855                 860

Ser Pro Val Ala Gly Arg Asn Glu Pro Glu Ser Lys Asp Leu Ile Gly
865                 870                 875                 880

Met Phe Val Asn Thr Leu Ala Leu Arg Ser His Leu Gly Asp Asn Pro
                885                 890                 895

Thr Val Asp Val Leu Leu Lys Gln Ile Lys Gln Asn Thr Leu Glu Ala
            900                 905                 910

Tyr Asn His Gln Asp Tyr Pro Phe Asp Lys Leu Val Asp Asp Leu Asp
        915                 920                 925

Pro His Arg Asp Leu Ser Arg Thr Pro Ile Phe Gln Val Met Met Gly
    930                 935                 940

Tyr Met Asn Met Pro Leu Met Val Ala Phe Arg Glu Ala Glu Val Arg
945                 950                 955                 960

Glu Arg Phe Val Arg His Lys Val Ala Arg Phe Asp Leu Thr Leu His
                965                 970                 975

Val Phe Glu Asp Glu Asp Gln Met Lys Ile Phe Phe Glu Tyr Asn Thr
            980                 985                 990

Asp Leu Phe Asp Glu Ser Thr Ile  Met Arg Trp Gln Asn  His Phe Glu
        995                 1000                1005

Thr Leu  Leu Gln Glu Ile Val  Ser Asn Pro Thr Lys  Arg Ile Ser
    1010                1015                1020

Glu Leu  Asn Ile Leu Thr Asn  Glu Glu Lys Tyr Glu  Ile Leu Glu
    1025                1030                1035

Met Asn  Asn Asn Ser Thr Glu  Tyr Pro Gln His Glu  Ser Val Ala
    1040                1045                1050

Glu Ile  Phe Arg Glu Thr Lys  Ile Lys His Gln Ala  Lys Leu Ala
    1055                1060                1065

Ile Thr  Tyr Lys Asp Arg Lys  Leu Thr Tyr Ala Glu  Leu Ser Glu
    1070                1075                1080

Lys Ala  Asn Ala Leu Ala His  Thr Leu Lys Arg Arg  Gly Val Ala
    1085                1090                1095

Gln His  Asp Val Val Gly Ile  Val Ala Glu Arg Ser  Pro Glu Thr
```

-continued

```
    1100                1105                1110

Ile Ile  Gly Ile Leu Ala Ile  Leu Lys Val Gly Ala  Ile Tyr Leu
    1115                1120                1125

Pro Ile  Asp Pro Lys Leu Pro  Gln Leu Thr Leu Gln  His Ile Trp
    1130                1135                1140

Arg Asp  Ser Gly Ala Lys Val  Leu Leu Gly Lys Asn  Glu Thr Thr
    1145                1150                1155

Val Glu  Val Gly Lys Glu Val  Pro Phe Val Asp Ile  Glu Gly Asp
    1160                1165                1170

Lys Gly  Lys Gln Glu Glu Leu  Val Cys Pro Ile Ser  Pro Glu Asp
    1175                1180                1185

Thr Ala  Tyr Ile Met Tyr Thr  Ser Gly Ser Thr Gly  Lys Pro Lys
    1190                1195                1200

Gly Val  Met Val Thr His Arg  Asn Ile Val Arg Leu  Val Lys Asn
    1205                1210                1215

Thr Asn  Phe Val Ser Leu Gln  Glu Gln Asp Val Leu  Leu Gln Thr
    1220                1225                1230

Gly Ser  Leu Thr Phe Asp Ala  Ala Thr Phe Glu Ile  Trp Gly Ala
    1235                1240                1245

Leu Leu  Asn Gly Leu Thr Leu  His Leu Val Glu Asp  Tyr Val Ile
    1250                1255                1260

Leu Asp  Gly Glu Ala Leu Gln  Glu Glu Ile Gln Gln  Asn Lys Ala
    1265                1270                1275

Thr Ile  Met Trp Val Ser Ala  Pro Leu Phe Asn Gln  Leu Ala Asp
    1280                1285                1290

Gln Asn  Pro Ala Met Phe Thr  Gly Ile Lys Gln Leu  Leu Ile Gly
    1295                1300                1305

Gly Asp  Val Leu Ser Pro Lys  His Ile Asn Lys Val  Met Asp His
    1310                1315                1320

Cys Ala  Pro Ile Asn Ile Ile  Asn Gly Tyr Gly Pro  Thr Glu Asn
    1325                1330                1335

Thr Thr  Phe Ser Thr Ser Phe  Val Ile Asp Gln Met  Tyr Gln Asp
    1340                1345                1350

Ser Ile  Pro Ile Gly Thr Pro  Ile Ala Asn Ser Ser  Ala Tyr Ile
    1355                1360                1365

Leu Asp  Val His Gln Asn Ile  Gln Pro Ile Gly Val  Val Gly Glu
    1370                1375                1380

Leu Cys  Val Gly Gly Asp Gly  Val Ala Lys Gly Tyr  Val Asn Leu
    1385                1390                1395

Glu Gln  Leu Thr Glu Glu Arg  Phe Ile Ala Asp Pro  Phe Leu Lys
    1400                1405                1410

Gly Ser  Thr Met Tyr Arg Thr  Gly Asp Tyr Val Lys  Leu Leu Pro
    1415                1420                1425

Asn Gly  Asn Ile Gln Tyr Ile  Gly Arg Val Asp Asn  Gln Val Lys
    1430                1435                1440

Ile Arg  Gly Phe Arg Ile Glu  Leu Glu Ala Ile Met  Asn Thr Leu
    1445                1450                1455

Lys Gln  Cys Glu Ser Ile Lys  Asp Val Ile Val Val  Val Gln Glu
    1460                1465                1470

Gln Asn  Gly Tyr Lys Thr Leu  Val Ala Tyr Val Val  Gly Glu Glu
    1475                1480                1485

Ser Leu  Ser Ile Glu Thr Val  Arg Ala Tyr Ala Lys  Lys His Leu
    1490                1495                1500
```

-continued

```
Ala Glu  Tyr Met Val Pro Ser  Gln Phe Ile Phe Ile  Glu Glu Ile
    1505                 1510                 1515

Pro Leu  Ser Ile Asn Gly Lys  Val Gln Tyr Ser Lys  Leu Pro Lys
    1520                 1525                 1530

Val Gln  Glu Val Leu His Lys  Lys Val Glu Thr Leu  Leu Pro Glu
    1535                 1540                 1545

Asn Arg  Leu Glu Glu Ile Ile  Leu Arg Val Tyr Arg  Asp Val Leu
    1550                 1555                 1560

Glu Lys  Glu Asp Phe Gly Val  Thr Asp Ser Phe Phe  Ala Tyr Gly
    1565                 1570                 1575

Gly Asp  Ser Leu Leu Ser Ile  Gln Val Val Ser Met  Leu Lys Lys
    1580                 1585                 1590

Glu Glu  Ile Ala Val Asp Pro  Lys Met Ile Phe Met  His Thr Thr
    1595                 1600                 1605

Val Arg  Glu Leu Ala Lys Ala  Cys Glu Asn Arg Pro  Val Met Glu
    1610                 1615                 1620

Glu Thr  Lys Arg Thr Glu Lys  Asp Tyr Leu Ile Gln  Met Arg Glu
    1625                 1630                 1635

Gly Ser  Glu Glu Asp Ser Cys  Ile Ile Phe Ala Pro  Pro Ala Gly
    1640                 1645                 1650

Gly Thr  Val Leu Gly Tyr Ile  Glu Leu Ala Arg Tyr  Phe Glu Gly
    1655                 1660                 1665

Ile Gly  Asn Val Tyr Gly Leu  Gln Ala Pro Gly Leu  Tyr Asp Asp
    1670                 1675                 1680

Glu Glu  Pro Thr Phe Leu Asp  Tyr Asp Glu Leu Val  Gln Val Phe
    1685                 1690                 1695

Leu Arg  Ser Ile Glu Gly Thr  Tyr Arg Pro Gly Gln  Asp Tyr Leu
    1700                 1705                 1710

Gly Gly  His Ser Leu Gly Gly  His Ile Ala Phe Gly  Met Cys Cys
    1715                 1720                 1725

Glu Leu  Ile Lys Gln Gly Lys  Ala Pro Lys Gly Leu  Leu Ile Leu
    1730                 1735                 1740

Asp Thr  Thr Pro Ser Leu Gln  Val Val Lys Gly Ala  Lys Asp Glu
    1745                 1750                 1755

Lys Ile  Ala Glu Glu Asp Phe  Lys Met Met Val Leu  Ala Ala Gly
    1760                 1765                 1770

Ile Gly  Asn Met Met Gly Val  Asp Pro Glu Glu Leu  Lys Gln Leu
    1775                 1780                 1785

Ser Tyr  Glu Glu Ala Lys Thr  Arg Val Val Ala Val  Ala Gln Lys
    1790                 1795                 1800

Asp Glu  Lys Leu Lys Thr Phe  Ile Asn Glu Thr Tyr  Leu Asp Lys
    1805                 1810                 1815

Tyr Leu  Lys Leu Gln Ile His  Ser Leu Leu Met Ser  Arg Thr Leu
    1820                 1825                 1830

Glu Leu  Glu Lys Thr Gln Leu  Asp Ile Pro Ile Lys  Val Phe Lys
    1835                 1840                 1845

Thr Gln  Phe His Thr Glu Glu  Leu Val Glu Arg Phe  Asp Ala Trp
    1850                 1855                 1860

His Asn  Tyr Thr Asn Gln Ala  Cys Thr Phe Ile Asp  Ile Pro Gly
    1865                 1870                 1875

Thr His  Thr Thr Met Met Arg  Leu Pro His Val Lys  Glu Val Ala
    1880                 1885                 1890
```

```
Lys Lys  Ile Glu Glu Gln Leu
    1895                1900


<210> SEQ ID NO 4
<211> LENGTH: 1020
<212> TYPE: PRT
<213> ORGANISM: Bacillus cereus

<400> SEQUENCE: 4

Val His Lys Thr Pro Ser Ala Thr Ala Leu Ile Tyr Arg Asn Lys Glu
1               5                   10                  15

Met Thr Tyr Glu Asp Val Asn Ala Gln Ala Asn Ala Leu Ala His Lys
            20                  25                  30

Leu Arg Asp Ala Gly Val Gly Pro Asn Gln Val Val Gly Val Leu Cys
        35                  40                  45

Asp Arg Ser Phe Glu Met Val Val Gly Ile Leu Ala Val Leu Lys Ala
    50                  55                  60

Gly Gly Ala Tyr Leu Pro Ile Asp Thr Ala Tyr Pro Met Gln Arg Thr
65                  70                  75                  80

Glu Tyr Val Leu Gln Asn Ser Glu Ala Thr Ile Leu Leu Thr Lys Glu
                85                  90                  95

Cys Tyr Leu Lys Glu Ser Leu Asp Phe Glu Gly Glu Val Phe Tyr Leu
            100                 105                 110

Asp Asp Ala Arg Leu Phe Glu Gly Asp Arg Arg Asp Leu Gln Asn Ile
        115                 120                 125

Asn Asn Pro Thr Asn Leu Ala Tyr Ile Ile Tyr Thr Ser Gly Ser Thr
    130                 135                 140

Gly Asn Pro Lys Gly Val Met Val Ala His Gln Ser Val Val Asn Leu
145                 150                 155                 160

Leu Leu Asp Leu Gln Glu Lys Tyr Pro Val Leu Ala Glu Asp Lys His
                165                 170                 175

Leu Leu Lys Thr Thr Tyr Thr Phe Asp Val Ser Val Ala Glu Ile Phe
            180                 185                 190

Gly Trp Phe His Ala Gly Gly Thr Leu Val Ile Ala Gly His Gly Asp
        195                 200                 205

Glu Lys Asp Pro Glu Lys Leu Ile Gln Leu Ile Gln Cys His Lys Val
    210                 215                 220

Thr His Ile Asn Phe Val Pro Ser Met Leu His Ala Met Leu Gln Ala
225                 230                 235                 240

Leu Asp Glu Lys Asp Phe Ala Ile Met Asn Arg Leu Lys Tyr Ile Ile
                245                 250                 255

Val Ala Gly Glu Ala Val Ser Pro Glu Leu Cys Asn Arg Leu Tyr Ala
            260                 265                 270

His Cys Pro Asn Val Lys Leu Glu Asn Leu Tyr Gly Pro Thr Glu Gly
        275                 280                 285

Thr Ile Tyr Ala Thr Gly Phe Ser Ile His Lys Glu Met Asn Val Ala
    290                 295                 300

Asn Val Pro Ile Gly Lys Pro Leu Ser His Val Glu Thr Tyr Ile Leu
305                 310                 315                 320

Asp Gln Asn Asn Gln Ile Val Pro Ile Gly Val Pro Gly Glu Leu Cys
                325                 330                 335

Leu Gly Gly Ile Cys Val Ala Lys Gly Tyr Met Lys Glu Pro Val Leu
            340                 345                 350

Thr Glu Glu Lys Phe Val Val Asn Pro Met Lys Gln Ser Glu Arg Met
        355                 360                 365
```

-continued

```
Tyr Arg Thr Gly Asp Leu Val Arg Trp Leu Ala Asp Gly Asn Ile Glu
    370                 375                 380

Tyr Leu Gly Arg Ile Asp Asn Gln Val Lys Ile Arg Gly Phe Arg Ile
385                 390                 395                 400

Glu Leu Gly Glu Ile Glu Ala Ala Ile Ala Ala Leu Glu Asp Val Val
                405                 410                 415

Gln Thr Ile Val Thr Thr Met Thr Asp His Lys Gly Ala Asn Lys Ile
            420                 425                 430

Val Ala Tyr Val Val Ser Glu Lys Tyr Asp Glu Glu Arg Ile Arg Glu
        435                 440                 445

His Val Lys Lys Thr Leu Pro Gln Tyr Met Val Pro Ser Tyr Phe Val
    450                 455                 460

Ser Met Lys Ala Leu Pro Leu Asn Lys Asn Gly Lys Val Asp Arg Lys
465                 470                 475                 480

Gln Leu His Ser Val Asp Leu Tyr Glu Thr Ser Met Asp Thr Val Ile
                485                 490                 495

Val Gly Pro Arg Asn Glu Lys Glu Ala Met Leu Ser Val Ile Trp Gln
            500                 505                 510

Glu Leu Leu Gly Leu Glu Asn Ile Ser Val His Asp Asn Phe Phe Lys
        515                 520                 525

Leu Gly Gly His Ser Ile Asn Ala Thr Gln Leu Val Ser Lys Ile Tyr
    530                 535                 540

Ser Val Cys Arg Val Arg Met Pro Leu Lys Asn Val Phe Gln Tyr Thr
545                 550                 555                 560

Thr Leu Ala Thr Met Ala Arg Val Leu Glu Glu Leu Leu Val Ser Ala
                565                 570                 575

Val Asp Glu Val Ala Val Thr Thr Glu Arg Ile Pro Lys Ile Leu Pro
            580                 585                 590

Arg Thr Tyr Tyr Asp Leu Ser Tyr Ser Gln Gln Arg Ile Tyr Phe Leu
        595                 600                 605

Ser Thr Met Glu Lys Glu Thr Asn Tyr Tyr Asn Ile Leu Gly Ala Trp
    610                 615                 620

Asp Ile Tyr Gly Lys Leu Asp Val Thr Leu Phe Glu Lys Ala Ile Gln
625                 630                 635                 640

Leu Leu Met Lys Lys His His Ser Leu Arg Ala Thr Phe Glu Ile Val
                645                 650                 655

Asp Gly Lys Pro Val Gln Ile Ile His Asp Asp Met Glu Ile Pro Val
            660                 665                 670

Gln Phe Ile Asp Leu Thr Val Met Pro Glu Gly Leu Arg Ile Glu Glu
        675                 680                 685

Val Asp Glu Leu Met Leu Lys Glu Ser Lys Arg Val Tyr Asn Leu Ala
    690                 695                 700

Asn Gly Pro Leu Met His Cys Thr Ile Val Lys Ile Lys Glu Gly Glu
705                 710                 715                 720

His Val Leu Leu Ile Gly Gln His His Ile Ile Ser Asp Gly Trp Ser
                725                 730                 735

Leu Gly Ile Phe Val Lys Glu Leu Asn Glu Met Tyr Asp Ala Phe Val
            740                 745                 750

Gln His Lys Pro Val Ala Glu Thr Pro Ser Thr Ile Ser Ile Met Asp
        755                 760                 765

Phe Thr Ala Trp His Asn Ser Lys Val Asp Glu Asp Gln Asp Asp Arg
    770                 775                 780
```

```
Gln Tyr Trp Leu Gln Arg Phe Glu Gly Glu Leu Pro Thr Leu Glu Leu
785                 790                 795                 800

Pro Thr Asp Arg Gln Arg Pro Leu Leu Lys Thr Tyr His Gly Asp Thr
                805                 810                 815

Leu Ser Tyr Lys Val Asn Ser Gln Leu His Gln Lys Leu Lys Asp Phe
            820                 825                 830

Ser His Ala Asn Gly Val Thr Met Phe Met Thr Leu Leu Thr Ala Tyr
        835                 840                 845

Asn Ile Met Leu Asn Lys Leu Thr Asn Glu Thr Asp Ile Val Val Gly
    850                 855                 860

Ser Pro Val Ala Gly Arg Asn Glu Pro Glu Ser Lys Asp Leu Ile Gly
865                 870                 875                 880

Met Phe Val Asn Thr Leu Ala Leu Arg Ser His Leu Gly Asp Asn Pro
                885                 890                 895

Thr Val Asp Val Leu Leu Lys Gln Ile Lys Gln Asn Thr Leu Glu Ala
            900                 905                 910

Tyr Asn His Gln Asp Tyr Pro Phe Asp Lys Leu Val Asp Asp Leu Asp
        915                 920                 925

Pro His Arg Asp Leu Ser Arg Thr Pro Ile Phe Gln Val Met Met Gly
    930                 935                 940

Tyr Met Asn Met Pro Leu Met Val Ala Phe Arg Glu Ala Glu Val Arg
945                 950                 955                 960

Glu Arg Phe Val Arg His Lys Val Ala Arg Phe Asp Leu Thr Leu His
                965                 970                 975

Val Phe Glu Asp Glu Asp Gln Met Lys Ile Phe Phe Glu Tyr Asn Thr
            980                 985                 990

Asp Leu Phe Asp Glu Ser Thr Ile  Met Arg Trp Gln Asn  His Phe Glu
        995                 1000                1005

Thr Leu  Leu Gln Glu Ile Val  Ser Asn Pro Thr Lys
    1010                 1015                 1020


<210> SEQ ID NO 5
<211> LENGTH: 880
<212> TYPE: PRT
<213> ORGANISM: Bacillus cereus

<400> SEQUENCE: 5

Arg Ile Ser Glu Leu Asn Ile Leu Thr Asn Glu Glu Lys Tyr Glu Ile
1               5                   10                  15

Leu Glu Met Asn Asn Asn Ser Thr Glu Tyr Pro Gln His Glu Ser Val
            20                  25                  30

Ala Glu Ile Phe Arg Glu Thr Lys Ile Lys His Gln Ala Lys Leu Ala
        35                  40                  45

Ile Thr Tyr Lys Asp Arg Lys Leu Thr Tyr Ala Glu Leu Ser Glu Lys
    50                  55                  60

Ala Asn Ala Leu Ala His Thr Leu Lys Arg Arg Gly Val Ala Gln His
65                  70                  75                  80

Asp Val Val Gly Ile Val Ala Glu Arg Ser Pro Glu Thr Ile Ile Gly
                85                  90                  95

Ile Leu Ala Ile Leu Lys Val Gly Ala Ile Tyr Leu Pro Ile Asp Pro
            100                 105                 110

Lys Leu Pro Gln Leu Thr Leu Gln His Ile Trp Arg Asp Ser Gly Ala
        115                 120                 125

Lys Val Leu Leu Gly Lys Asn Glu Thr Thr Val Glu Val Gly Lys Glu
    130                 135                 140
```

-continued

```
Val Pro Phe Val Asp Ile Glu Gly Asp Lys Gly Lys Gln Glu Glu Leu
145                 150                 155                 160

Val Cys Pro Ile Ser Pro Glu Asp Thr Ala Tyr Ile Met Tyr Thr Ser
                165                 170                 175

Gly Ser Thr Gly Lys Pro Lys Gly Val Met Val Thr His Arg Asn Ile
            180                 185                 190

Val Arg Leu Val Lys Asn Thr Asn Phe Val Ser Leu Gln Glu Gln Asp
        195                 200                 205

Val Leu Leu Gln Thr Gly Ser Leu Thr Phe Asp Ala Ala Thr Phe Glu
    210                 215                 220

Ile Trp Gly Ala Leu Leu Asn Gly Leu Thr Leu His Leu Val Glu Asp
225                 230                 235                 240

Tyr Val Ile Leu Asp Gly Glu Ala Leu Gln Glu Glu Ile Gln Gln Asn
                245                 250                 255

Lys Ala Thr Ile Met Trp Val Ser Ala Pro Leu Phe Asn Gln Leu Ala
            260                 265                 270

Asp Gln Asn Pro Ala Met Phe Thr Gly Ile Lys Gln Leu Leu Ile Gly
        275                 280                 285

Gly Asp Val Leu Ser Pro Lys His Ile Asn Lys Val Met Asp His Cys
    290                 295                 300

Ala Pro Ile Asn Ile Ile Asn Gly Tyr Gly Pro Thr Glu Asn Thr Thr
305                 310                 315                 320

Phe Ser Thr Ser Phe Val Ile Asp Gln Met Tyr Gln Asp Ser Ile Pro
                325                 330                 335

Ile Gly Thr Pro Ile Ala Asn Ser Ser Ala Tyr Ile Leu Asp Val His
            340                 345                 350

Gln Asn Ile Gln Pro Ile Gly Val Val Gly Glu Leu Cys Val Gly Gly
        355                 360                 365

Asp Gly Val Ala Lys Gly Tyr Val Asn Leu Glu Gln Leu Thr Glu Glu
    370                 375                 380

Arg Phe Ile Ala Asp Pro Phe Leu Lys Gly Ser Thr Met Tyr Arg Thr
385                 390                 395                 400

Gly Asp Tyr Val Lys Leu Leu Pro Asn Gly Asn Ile Gln Tyr Ile Gly
                405                 410                 415

Arg Val Asp Asn Gln Val Lys Ile Arg Gly Phe Arg Ile Glu Leu Glu
            420                 425                 430

Ala Ile Met Asn Thr Leu Lys Gln Cys Glu Ser Ile Lys Asp Val Ile
        435                 440                 445

Val Val Val Gln Glu Gln Asn Gly Tyr Lys Thr Leu Val Ala Tyr Val
    450                 455                 460

Val Gly Glu Glu Ser Leu Ser Ile Glu Thr Val Arg Ala Tyr Ala Lys
465                 470                 475                 480

Lys His Leu Ala Glu Tyr Met Val Pro Ser Gln Phe Ile Phe Ile Glu
                485                 490                 495

Glu Ile Pro Leu Ser Ile Asn Gly Lys Val Gln Tyr Ser Lys Leu Pro
            500                 505                 510

Lys Val Gln Glu Val Leu His Lys Lys Val Glu Thr Leu Leu Pro Glu
        515                 520                 525

Asn Arg Leu Glu Glu Ile Ile Leu Arg Val Tyr Arg Asp Val Leu Glu
    530                 535                 540

Lys Glu Asp Phe Gly Val Thr Asp Ser Phe Phe Ala Tyr Gly Gly Asp
545                 550                 555                 560
```

-continued

```
Ser Leu Leu Ser Ile Gln Val Val Ser Met Leu Lys Lys Glu Glu Ile
                565                 570                 575

Ala Val Asp Pro Lys Met Ile Phe Met His Thr Thr Val Arg Glu Leu
            580                 585                 590

Ala Lys Ala Cys Glu Asn Arg Pro Val Met Glu Glu Thr Lys Arg Thr
        595                 600                 605

Glu Lys Asp Tyr Leu Ile Gln Met Arg Glu Gly Ser Glu Glu Asp Ser
    610                 615                 620

Cys Ile Ile Phe Ala Pro Pro Ala Gly Gly Thr Val Leu Gly Tyr Ile
625                 630                 635                 640

Glu Leu Ala Arg Tyr Phe Glu Gly Ile Gly Asn Val Tyr Gly Leu Gln
                645                 650                 655

Ala Pro Gly Leu Tyr Asp Asp Glu Glu Pro Thr Phe Leu Asp Tyr Asp
            660                 665                 670

Glu Leu Val Gln Val Phe Leu Arg Ser Ile Glu Gly Thr Tyr Arg Pro
        675                 680                 685

Gly Gln Asp Tyr Leu Gly Gly His Ser Leu Gly Gly His Ile Ala Phe
    690                 695                 700

Gly Met Cys Cys Glu Leu Ile Lys Gln Gly Lys Ala Pro Lys Gly Leu
705                 710                 715                 720

Leu Ile Leu Asp Thr Thr Pro Ser Leu Gln Val Val Lys Gly Ala Lys
                725                 730                 735

Asp Glu Lys Ile Ala Glu Glu Asp Phe Lys Met Met Val Leu Ala Ala
            740                 745                 750

Gly Ile Gly Asn Met Met Gly Val Asp Pro Glu Glu Leu Lys Gln Leu
        755                 760                 765

Ser Tyr Glu Glu Ala Lys Thr Arg Val Val Ala Val Ala Gln Lys Asp
    770                 775                 780

Glu Lys Leu Lys Thr Phe Ile Asn Glu Thr Tyr Leu Asp Lys Tyr Leu
785                 790                 795                 800

Lys Leu Gln Ile His Ser Leu Leu Met Ser Arg Thr Leu Glu Leu Glu
                805                 810                 815

Lys Thr Gln Leu Asp Ile Pro Ile Lys Val Phe Lys Thr Gln Phe His
            820                 825                 830

Thr Glu Glu Leu Val Glu Arg Phe Asp Ala Trp His Asn Tyr Thr Asn
        835                 840                 845

Gln Ala Cys Thr Phe Ile Asp Ile Pro Gly Thr His Thr Thr Met Met
    850                 855                 860

Arg Leu Pro His Val Lys Glu Val Ala Lys Lys Ile Glu Glu Gln Leu
865                 870                 875                 880
```

```
<210> SEQ ID NO 6
<211> LENGTH: 11115
<212> TYPE: DNA
<213> ORGANISM: Bacillus cereus

<400> SEQUENCE: 6

tttataaaat caatgaatca gttgggaaaa tcaaaaaatt tacataatgg ggggatgatg      60

gagatgaaac gagtggaaga acatgatcac attcatgtgt taaatgaaat agaaaacgaa     120

tgcgaaagaa gatatgggag aagtaatatt gcaattatgc ttgaaaagca tggtgttcat     180

gaacagccgc ttcatataga agacttattt catgaggtag agatgcaaga acattcacga     240

gtatcgcgcc acgaaacagt tttgatgaca gataaacaat gtatagatga gagtggaaaa     300

ccgttagctc ttcgttttgg tgagccactt catcttgatg actgtacccc aaaaacacta     360
```

-continued caagaaattt taaagcgtgc cgctaagcaa gcaaaagata aagggatgac atttgtatat 420
gaagatggac atgaagagta cctctcctac caagagatgt tggcagatgc ggagcggtta 480
ctaaaagggt tgcgaaatct tggtatacaa ccaggagaaa gtattttgtt tcaatttaag 540
gacaataagc attttgttac tgcgttttgg gcatgtatac ttgggggatt tttaccaacg 600
ccgttaggaa cggcccctat ctatagtgag caaaatgcac aagtattaaa actttataac 660
acatggcagc tattagaaca accgattatt ttaacggaat ttgaattgaa agaagagatt 720
gctgcaattc gaacaacatt gcaacgtcaa gagattgtta tacatagtat tgagaatgtt 780
atggatacag cgcgcgatac aaactggttt ccttgtaccg aagatactat tgttttgaat 840
ttattaacgt ctggtagcac aggagtaccc aaatgtgtgc agcacaaaag taaatccatt 900
attgcgcgca cagtttccaa ttgtattgac cgccagctag atgaaaaaga agtatcgtta 960
aattggatgc cgcttgatca tgttggaggc atcgtaatgt gtcacattcg tgatacctat 1020
ttaatgtgcc aacaggtaaa ctgtcttatt tcggcattta ttgaaaatcc gctaaattgg 1080
ttgcactgga ttgatgctta ctcagcgaca tttacatggg cgccaaactt cgctttttca 1140
ttaattaacc agtatgaaga agagattaaa tcatcttcat ggaatctttc ttcgatgaga 1200
tacatcgtaa atggtgggga agctgttatt tcaagtgttg ggatgaaatt tttacaattg 1260
ttacagcaac atcaattgcc ttcgaactgt cttattccta cgtttgggat gtctgaagtt 1320
tcttcgggta ttattgaatg tcattcgttt tatacgcaaa cgacaaatac aggaatgttg 1380
tatgttgata agaattcttt agatggtaat ttacaattca catatgaggg gcaccaaaat 1440
gccattgttt ttacggaagt agggagaccg atgcctggta ttggcattcg tattgttgat 1500
gaggacaatc agtgcctgtc agaagatcgt attggacgat tccaaattca tggtccaacg 1560
gttatgaatg gttatttcaa aaatgatgaa gcaaatgcgg aaagttttac tgaagatggc 1620
tggttcgata gtggagatct ggggtttata cataacggta atcttgtcat tacaggaaga 1680
aaaaaggata tgattgttgt tcatggtgca aattactaca actatgaaat tgaagccttg 1740
gtagaacaag tacctggggt ggaaaccacg tttgtatgtg caacgagtgt gaagtcggct 1800
gaaggagcag aggaattagc tattttcttt gtcccagtaa ttaatcatgt ttctgtgatg 1860
tttgcgacga tgcaacaaat caaacaaatt gttgcgcgca aaatgggtat cacgccgaaa 1920
gtgattatac caattcagaa ggaagcattc tttaaaacgg atagtgggaa aataacgaga 1980
aatgcatttc aaaaacagtt tgagaacggg gcatatagag agattacaca aaagattgat 2040
tgccatttac aaaatgaaaa aacactatct cagtggtttt atcgtgaaaa attagtcgaa 2100
agtaagttgg gcaaaagcgt atcctcccaa aaagaaacgt atgttttctt tcgacaaggt 2160
aaatcatttc atcatgtcct aaaagaaaag ttaacgcaac attctgttgt tattgtggat 2220
gtaggagaaa cattcggtga gatccatcca aatcattatc aaattaatcc taaaaacaaa 2280
atggattacg ttcgattatt tgaagaactc gcaaaaagaa atgtagaaga tcaagttttt 2340
catctcttgc atgcttggaa ttattgcgat acagttccaa cttttagatc ggtagaagat 2400
ttagctaatg cgcaatatct tggtgtgttt agtgtgatgt tcgcacttca agctattatg 2460
catgcgaaat tgccactacg tcgtgttacg gtgattgcga caaatagtgt tggattagaa 2520
gcgaaggaaa tgaactattc atgttcaaca ttagaaggtt atgtgaaaac tttgccagct 2580
gagtttgaaa atttacaagt gaagtatatt gatatagaag gaaaagatat acagtttgat 2640
actgagaccg tatggaaaga acttcagcaa caagaaacca ttcctgtcgt attgtatcgt 2700

-continued

```
gatgagaaaa gatacaaaat aggtttagaa aaagtaccaa tgttagaaca gaaagaaaaa   2760
aatattccgt ttcaacagca agggttttac atcattacag gtggtcttgg tggtttgggg   2820
acgcttgtag ccaaattact tttagaacga tacagcgcaa atgttctttt acttggtcga   2880
acagaaattg aaacaaatgc agaaaaaatg cgccttcttg attcattaaa agagtatgaa   2940
caatatggtg gtacagtcca atataaaatg tgcaatgtaa tggatttaga tgcgatgcga   3000
aaagttgttc attcacagga agaacgtctg caacaaaagg taaatgggat tatccacctt   3060
gcagggatta ttcaagaaat actgatagaa aagcaaaccg aaaaagaact gcatgctatg   3120
tttgaagcta aggtatatgc atcttgggtg ctacatgaaa tcgtaaaaga aaggcaagat   3180
tgtctctaca ttacaacttc ttcagcaaga acgttgttac cggggatgac catctcagct   3240
tattgtagtg cgaatcgatt tgttgaaaat tttgcatatt atcaacgaag tcaaaatgta   3300
aatagctact gtttttcatg gagtttctgg aatgagattg gaatgggtac aaatttactt   3360
attaaaaatg cgttgatagc aaaaggattt caattgatcg atgatcaaaa aggtatatat   3420
tccctttttgg cgggattaaa agggaacgaa cctaatgttt ttgttggaat caatcatgaa   3480
aaagaagaaa tggctcatct gattggaacc gaggaacaag aaacacaaca attaacaatc   3540
tatattacac cagaatactt acatattctt gaagaagtgt tctctatact aaatagagaa   3600
gaatttggtg gattggagaa agagattgtc attctaccaa aattaccgct tgatgaatat   3660
ggtaaagtag atcaaactcg tttggctcat gcgtcggata gccgttttgg aaagaaacaa   3720
catatcgtac caagaaatga tatagaagag aaaattgcat tcatttggga aggtcttttg   3780
aataaaaagg atattagtgt acttgaccat ttcttcgaat taggtggtga ttctttaaaa   3840
gcgacacaaa tgatttctgc gttgaaaaag aattttgctg ttacgattac gcaacaggaa   3900
tttttttcaat cgagtacagt agaagagctt gctagtttag tagaaaagaa actttctcgt   3960
actcgtacgc atgaaatgga catagttact tttagtgacc gaggtaacgt agtagagatg   4020
tcttctgcac aaaagcggca atggttttta tatgaaatgg atcgagaaaa tccttattac   4080
aataatacac ttgtaattcg tttgacggga gaaattcatc ttcctatttt aagaagttct   4140
attattgagt tagtaaataa gcatgaaaca ttgcgaacaa catttgtgat ggtggatggt   4200
ataccatcac aaattattgc agatgaagag ttagttgaaa tagaggaaat tgatttgaaa   4260
cacctatctg ctgaggagac gttgcaaaaa ctagagggtt tacgacaacg ggaagcaaat   4320
acggcgttta aaatcgaaaa tagcgctttt cgtgcaaaag tgattttaat tgatgagaag   4380
agagtggaga ttttactttc cgtgcatcac attgtttcgg atggttggtc gatggggatt   4440
ttagtgaagg acattgcgga aatctatgaa gatattcggc agtgggggaga aagtaagcaa   4500
gagccattac cgattcaata cgcagattat actttgtggc aaaatgagtt tatgaaaggt   4560
gaggaattta gcaagcaact gtcttattgg aaggagaaat tagctgaaga tatacctgta   4620
cttgatcttc cgttagataa accacggcca ccaattcaaa catatcgtgg gaaggttaag   4680
actttcacgt tacatgaaaa catgacaagg atgctaaaag aaatatgtca agaagaagaa   4740
tgcacgctct ttatgttgtt actttcggct ttctcatcat tattacatcg ttatacaggt   4800
caggaggatc ttgttgttgg ttcgctagtt gcaaatcgaa accgtgagca aatcgagaaa   4860
ttgattggtt tctttgttaa tacgttaccg ctacgtatta atcttcatcg ggaaatgcaa   4920
tttactgaat tgctttcgca agtaaagaaa acgaccattg atgcatatga tcatcaagat   4980
gtgccttttg agctactagt cgatgaatta cagattgaga gagattcgag tcgtaatgcg   5040
ctattccaag tgttgtttgt cttacaaaac gcacaattac aagcagtaga cttagagaaa   5100
```

-continued

```
gcgacaatgg aactcgaaat tttagatagt gacacggcca agtttgatat gtcagtgcaa   5160
attttcgaat tggaggacac tttatctatc aaattagagt acaatacgga tttatttttt   5220
gatgatacaa tagaacgctt tcttgctcat tatgaaacca tattagcaag cgttattcat   5280
aatcaaaagg caaaaatagg ggaattgtca attttaccac aatctgaata tacgaaactt   5340
gtatctgagt ggaatgaaaa gagtgccact tataatggaa atcagtgtat tcatgaattg   5400
ttcgaagcag ctgttcacaa aacgccatct gcaacagcgc ttatttatcg caacaaagag   5460
atgacatacg aggatgttaa tgcgcaggca aatgcacttg cacataaatt aagagatgca   5520
ggtgttggac caaaccaggt agttggcgtg ttatgtgatc gctctttcga gatggttgtt   5580
ggtatattag ctgttttaaa agcaggtggt gcgtatttgc caattgatac agcgtacccg   5640
atgcaacgaa cagaatacgt cctgcaaaat agtgaggcaa ctattctctt aacaaaggaa   5700
tgttacctta aggagtcttt agattttgag gggaagtttt tttacttaga tgatgcaaga   5760
ctgtttgaag ggatagaaag agatttacaa aatatcaata atcctactaa ccttgcttat   5820
atcatttata catcaggatc cacgggaaat ccaaaaggtg ttatggtagc gcatcaaagt   5880
gttgtgaatt tgctactcga tttacaagag aaatatccgg tgctagcaga agataagcac   5940
ttgttaaaaa caacatatac gtttgatgtt tctgtagccg aaatttttgg atggtttcat   6000
gcaggtggca cacttgttat tgctggacat ggtgatgaaa aagacccaga gaaactgatt   6060
caattgattc aatgccacaa ggttacacat attaacttcg taccatcgat gctacatgca   6120
atgttacagg ccttggatga aaaagatttt gcaattatga atcggttgaa atatattatc   6180
gtcgcaggag aagctgtttc accagaactt tgtaatcgac tgtacgctca ttgtccaaat   6240
gtaaaactag aaaatctata tgggccaacg gaaggaacga tttatgcgac agggttttct   6300
attcataaag aaatgaatgt agctaatgta ccgattggaa aaccactttc tcatgtggaa   6360
acgtatattc ttgatcaaaa caatcaaatt gtaccaattg gtgtaccagg tgaattgtgt   6420
ctgggaggaa tatgtgtagc aaaaggttat atgaaagagc cggtgttaac agaagaaaaa   6480
ttcgtcgtca atcctatgaa acaaagtgaa agaatgtacc gaacgggtga tttggtacgc   6540
tggttagcag atgggaatat tgaatattta ggaagaatag ataaccaagt caagataaga   6600
ggcttccgaa ttgagcttgg tgaaattgaa gcggcaattg ctgcattaga agatgtagta   6660
caaacaattg ttacaacaat gacggatcat aaaggtgcga acaagattgt cgcatatgtt   6720
gtgagcgaaa agtatgatga agaacgaatt cgtgaacatg tgaaaaagac gttgccgcaa   6780
tatatggtac caagttattt cgtttcgatg aaggcattgc ctcttaataa aaatggaaaa   6840
gttgatcgca aacagttgca ttcggttgat ctttatgaaa cgagtatgga tacagtcatt   6900
gtgggaccaa gaaacgaaaa agaagcaatg ctttcggtta tttggcaaga gcttttggga   6960
ttagagaata tcagtgttca cgataatttc tttaagcttg gtggtcattc cattaatgcg   7020
acacaattgg tatcaaaaat ttatagtgtt tgccgagtga gaatgcctct taaaaatgtg   7080
tttcagtata caacgttagc tacaatggca cgggtgttag aagagttgtt ggtaagcgct   7140
gttgacgaag tagctgtaac aacggagcgc attccaaaga tactaccgag aacatattac   7200
gatttgtcgt attcacaaca aagaatttat ttcttatcta caatggagaa agaaaccaat   7260
tactataata ttcttggtgc ttgggatatt tatgggaaac tagatgttac gctatttgaa   7320
aaagcaatcc aactattaat gaagaaacac cattcattac gtgcaacatt tgaaatcgtg   7380
gacggcaaac ctgtgcaaat catccacgat gatatggaaa ttcctgtgca atttattgac   7440
```

-continued

```
cttactgtga tgccagaagg attacggata gaagaagtag atgaacttat gttaaaagag   7500
tctaaaagag tatacaatct cgcaaatggt ccgttaatgc attgtacaat tgttaagata   7560
aaagaaggtg agcatgtatt attgattgga caacatcata tcattagtga tggttggtca   7620
cttggtattt ttgtaaaaga gttaaatgaa atgtatgatg cctttgtgca acacaaacca   7680
gttgctgaaa caccatcaac aatctccatt atggacttta ctgcttggca caatagtaaa   7740
gtagatgaag atcaagatga tcgacaatat tggttacagc gatttgaggg agagttaccg   7800
acgttagagt tgccgacaga cagacaacgt ccacttttga aaacatatca tggtgacaca   7860
ttatcatata aggtgaattc tcaattgcat caaaaattaa aggactttag tcatgcaaat   7920
ggtgtaacga tgtttatgac gctattaacg gcgtataata ttatgttgaa taagttaaca   7980
aatgaaacag acattgttgt tggctcccct gtagcaggta gaaatgaacc agaatcaaaa   8040
gatttaatcg ggatgtttgt gaatacgtta gcgttacgtt cgcatttagg agataatccg   8100
acagttgatg tcttattaaa acaaataaaa cagaatactt tagaagcata caatcatcaa   8160
gattatccat ttgataagtt ggttgatgac ttggatccac atcgagattt aagtaggaca   8220
ccaattttcc aagtgatgat gggatatatg aatatgccat tgatggttgc atttcgtgaa   8280
gcagaggttc gcgaacgatt tgttcgacat aaagtcgcaa ggtttgattt aacacttcat   8340
gtgtttgaag atgaagatca gatgaaaata ttctttgagt ataatacaga tttatttgat   8400
gaatcaacga ttatgcgttg gcagaatcat ttcgaaacgc tattacagga aattgtatcg   8460
aatccgacaa aacgtatttc ggaattgaat atacttacaa atgaggagaa atatgaaatt   8520
ctagagatga acaataattc aacggagtat cctcagcatg aatctgttgc ggagattttt   8580
agagaaacga agataaagca tcaagcaaaa ctagcaatta cgtacaaaga tagaaagtta   8640
acgtatgcag agttgagtga aaaagcaaat gcgttggcac atacattgaa acgtcgaggt   8700
gttgcgcagc atgatgttgt tggaattgtc gcagagcgtt cgcctgaaac aattattgga   8760
atactcgcaa tcttaaaagt aggagcaatt tatttgccaa ttgatccaaa actaccgcaa   8820
ttaacactgc aacacatttg gcgagatagc ggtgcaaaag tcctcctagg gaaaaatgaa   8880
acaactgtag aagttggcaa ggaagttccg tttgtggaca tcgaagggga taaagggaag   8940
caagaggagt tagtgtgtcc aattagtcca gaagatacgg catatattat gtatacgtca   9000
ggcagtactg gaaaaccaaa aggggttatg gtgacacata gaaatattgt tcgtttagta   9060
aaaaatacga atttcgtttc tttgcaagag caagatgtgt tgttacagac aggttcgctt   9120
acttttgacg ctgcaacatt tgaaatttgg ggcgcattgc taaatggact tacgcttcat   9180
ttagtagaag attacgtaat tttagatggg gaggcgcttc aggaagagat tcagcagaac   9240
aaagcaacca ttatgtgggt gagtgcaccg ctgtttaatc aattggcgga tcaaaaccca   9300
gcgatgttta caggcattaa gcaattgctc attggtggtg atgttttatc gccaaaacat   9360
attaacaaag tgatggacca ttgtgcacca atcaatatca ttaatggata cggtccaaca   9420
gaaaatacga cgttctcgac gtcatttgta attgatcaaa tgtatcaaga cagcattccg   9480
attggaacac cgattgctaa ttctagtgct tacattttag atgtacatca aaatatacaa   9540
cctattggtg tagttggcga actatgtgtt ggtggtgatg gagttgcaaa aggttatgtg   9600
aaccttgaac aattaacaga agaacggttt atagcagatc cgttcctaaa gggttctaca   9660
atgtacagaa ccggcgatta tgtgaaatta ttgcctaatg gaaatattca atacattgga   9720
cgtgtggaca atcaagtgaa aattcgtgga ttccgcatcg aattagaagc cattatgaac   9780
acattaaaac aatgtgaatc aatcaaagat gtaattgttg ttgtacaaga acagaatggg   9840
```

```
tataaaacac tggttgcata tgttgtggga gaagaatcgc tttcaataga aacagtgagg   9900

gcctatgcaa aaaaacattt ggctgaatat atggtacctt ctcaatttat atttatagaa   9960

gaaattccgc tctcaataaa tgggaaagta cagtatagta agttaccgaa agtacaagaa  10020

gtattgcata aaaaagtaga aacgctgtta ccagaaaaca gattagaaga aattattcta  10080

cgtgtgtatc gtgatgtatt agagaaagaa gattttggcg taacagattc attcttcgct  10140

tatggtggtg actctttact aagtattcaa gtcgtttcga tgttgaaaaa agaggagatt  10200

gcagtagatc cgaaaatgat ttttatgcat acaacggtta gagagttagc aaaggcatgt  10260

gaaaatcgtc cggttatgga agaaacaaaa aggactgaga aggattattt aattcaaatg  10320

cgtgaaggta gtgaagaaga tagttgtatc atttttgctc ctccggcagg tggaacggta  10380

cttggatata tagaattagc aaggtatttc gagggaattg gcaatgttta cggcctacaa  10440

gcaccgggac tgtatgacga tgaagagcct acgttcttag attacgatga acttgtacaa  10500

gtgtttcttc gctcgattga agggacatat cgtccaggtc aagattattt aggtggccac  10560

tccttagggg gacatatcgc atttggaatg tgctgtgaac tgattaagca aggaaaggca  10620

ccaaagggat tgctaattct agatacaaca ccatcacttc aagttgtaaa gggggccaag  10680

gatgaaaaaa tagccgagga ggactttaaa atgatggtac tggctgccgg tatcggaaat  10740

atgatgggtg ttgatccaga agaattaaag caactgtcgt atgaagaagc aaaaacaaga  10800

gttgtcgcag tggcacaaaa ggatgaaaag ttaaaaactt ttataaatga aacatatttg  10860

gataagtatt tgaagttaca aattcatagt ttactaatgt cacgaacatt agaattggag  10920

aaaacacaat tagatattcc gattaaggta tttaaaacac agtttcatac agaagagcta  10980

gtagaaagat ttgatgcttg gcataactat acaaatcaag cctgcacatt cattgatata  11040

ccaggcacac atacgacgat gatgcgttta ccacatgtga aagaggtagc gaaaaaaata  11100

gaagaacagc tataa                                                   11115
```

```
<210> SEQ ID NO 7
<211> LENGTH: 5700
<212> TYPE: DNA
<213> ORGANISM: Bacillus cereus

<400> SEQUENCE: 7
```

```
cacaaaacgc catctgcaac agcgcttatt tatcgcaaca aagagatgac atacgaggat     60

gttaatgcgc aggcaaatgc acttgcacat aaattaagag atgcaggtgt tggaccaaac    120

caggtagttg gcgtgttatg tgatcgctct ttcgagatgg ttgttggtat attagctgtt    180

ttaaaagcag gtggtgcgta tttgccaatt gatacagcgt acccgatgca acgaacagaa    240

tacgtcctgc aaaatagtga ggcaactatt ctcttaacaa aggaatgtta ccttaaggag    300

tctttagatt ttgaggggga agttttttac ttagatgatg caagactgtt tgaaggggat    360

agaagagatt tacaaaatat caataatcct actaaccttg cttatatcat ttatacatca    420

ggatccacgg gaaatccaaa aggtgttatg gtagcgcatc aaagtgttgt gaatttgcta    480

ctcgatttac aagagaaata tccggtgcta gcagaagata agcacttgtt aaaaacaaca    540

tatacgtttg atgtttctgt agccgaaatt tttggatggt ttcatgcagg tggcacactt    600

gttattgctg gacatggtga tgaaaaagac ccagagaaac tgattcaatt gattcaatgc    660

cacaaggtta cacatattaa cttcgtacca tcgatgctac atgcaatgtt acaggccttg    720

gatgaaaaag attttgcaat tatgaatcgg ttgaaatata ttatcgtcgc aggagaagct    780
```

-continued

```
gtttcaccag aactttgtaa tcgactgtac gctcattgtc caaatgtaaa actagaaaat    840
ctatatgggc caacggaagg aacgatttat gcgacagggt tttctattca taaagaaatg    900
aatgtagcta atgtaccgat tggaaaacca ctttctcatg tggaaacgta tattcttgat    960
caaaacaatc aaattgtacc aattggtgta ccaggtgaat tgtgtctggg aggaatatgt   1020
gtagcaaaag gttatatgaa agagccggtg ttaacagaag aaaaattcgt cgtcaatcct   1080
atgaaacaaa gtgaaagaat gtaccgaacg ggtgatttgg tacgctggtt agcagatggg   1140
aatattgaat atttaggaag aatagataac caagtcaaga taagaggctt ccgaattgag   1200
cttggtgaaa ttgaagcggc aattgctgca ttagaagatg tagtacaaac aattgttaca   1260
acaatgacgg atcataaagg tgcgaacaag attgtcgcat atgttgtgag cgaaaagtat   1320
gatgaagaac gaattcgtga acatgtgaaa aagacgttgc cgcaatatat ggtaccaagt   1380
tatttcgttt cgatgaaggc attgcctctt aataaaaatg gaaaagttga tcgcaaacag   1440
ttgcattcgg ttgatcttta tgaaacgagt atggatacag tcattgtggg accaagaaac   1500
gaaaaagaag caatgctttc ggttatttgg caagagcttt tgggattaga gaatatcagt   1560
gttcacgata atttctttaa gcttggtggt cattccatta atgcgacaca attggtatca   1620
aaaatttata gtgtttgccg agtgagaatg cctcttaaaa atgtgtttca gtatacaacg   1680
ttagctacaa tggcacgggt gttagaagag ttgttggtaa gcgctgttga cgaagtagct   1740
gtaacaacgg agcgcattcc aaagatacta ccgagaacat attacgattt gtcgtattca   1800
caacaaagaa tttatttctt atctacaatg gagaaagaaa ccaattacta taatattctt   1860
ggtgcttggg atatttatgg gaaactagat gttacgctat ttgaaaaagc aatccaacta   1920
ttaatgaaga aacaccattc attacgtgca acatttgaaa tcgtggacgg caaacctgtg   1980
caaatcatcc acgatgatat ggaaattcct gtgcaattta ttgaccttac tgtgatgcca   2040
gaaggattac ggatagaaga agtagatgaa cttatgttaa aagagtctaa aagagtatac   2100
aatctcgcaa atggtccgtt aatgcattgt acaattgtta agataaaaga aggtgagcat   2160
gtattattga ttggacaaca tcatatcatt agtgatggtt ggtcacttgg tatttttgta   2220
aaagagttaa atgaaatgta tgatgccttt gtgcaacaca aaccagttgc tgaaacacca   2280
tcaacaatct ccattatgga ctttactgct tggcacaata gtaaagtaga tgaagatcaa   2340
gatgatcgac aatattggtt acagcgattt gagggagagt taccgacgtt agagttgccg   2400
acagacagac aacgtccact tttgaaaaca tatcatggtg acacattatc atataaggtg   2460
aattctcaat tgcatcaaaa attaaaggac tttagtcatg caaatggtgt aacgatgttt   2520
atgacgctat taacggcgta taatattatg ttgaataagt taacaaatga aacagacatt   2580
gttgttggct cccctgtagc aggtagaaat gaaccagaat caaaagattt aatcgggatg   2640
tttgtgaata cgttagcgtt acgttcgcat ttaggagata atccgacagt tgatgtctta   2700
ttaaaacaaa taaaacagaa tactttagaa gcatacaatc atcaagatta tccatttgat   2760
aagttggttg atgacttgga tccacatcga gatttaagta ggacaccaat tttccaagtg   2820
atgatgggat atatgaatat gccattgatg gttgcatttc gtgaagcaga ggttcgcgaa   2880
cgatttgttc gacataaagt cgcaaggttt gatttaacac ttcatgtgtt tgaagatgaa   2940
gatcagatga aaatattctt tgagtataat acagatttat ttgatgaatc aacgattatg   3000
cgttggcaga atcatttcga aacgctatta caggaaattg tatcgaatcc gacaaaacgt   3060
atttcggaat tgaatatact tacaaatgag gagaaatatg aaattctaga gatgaacaat   3120
aattcaacgg agtatcctca gcatgaatct gttgcggaga tttttagaga aacgaagata   3180
```

-continued

```
aagcatcaag caaaactagc aattacgtac aaagatagaa agttaacgta tgcagagttg   3240
agtgaaaaag caaatgcgtt ggcacataca ttgaaacgtc gaggtgttgc gcagcatgat   3300
gttgttggaa ttgtcgcaga gcgttcgcct gaaacaatta ttggaatact cgcaatctta   3360
aaagtaggag caatttattt gccaattgat ccaaaactac cgcaattaac actgcaacac   3420
atttggcgag atagcggtgc aaaagtcctc ctagggaaaa atgaaacaac tgtagaagtt   3480
ggcaaggaag ttccgtttgt ggacatcgaa ggggataaag ggaagcaaga ggagttagtg   3540
tgtccaatta gtccagaaga tacggcatat attatgtata cgtcaggcag tactggaaaa   3600
ccaaaagggg ttatggtgac acatagaaat attgttcgtt tagtaaaaaa tacgaatttc   3660
gtttctttgc aagagcaaga tgtgttgtta cagacaggtt cgcttacttt tgacgctgca   3720
acatttgaaa tttggggcgc attgctaaat ggacttacgc ttcatttagt agaagattac   3780
gtaattttag atggggaggc gcttcaggaa gagattcagc agaacaaagc aaccattatg   3840
tgggtgagtg caccgctgtt taatcaattg gcggatcaaa acccagcgat gtttacaggc   3900
attaagcaat tgctcattgg tggtgatgtt ttatcgccaa aacatattaa caaagtgatg   3960
gaccattgtg caccaatcaa tatcattaat ggatacggtc caacagaaaa tacgacgttc   4020
tcgacgtcat ttgtaattga tcaaatgtat caagacagca ttccgattgg aacaccgatt   4080
gctaattcta gtgcttacat tttagatgta catcaaaata tacaacctat tggtgtagtt   4140
ggcgaactat gtgttggtgg tgatggagtt gcaaaaggtt atgtgaacct tgaacaatta   4200
acagaagaac ggtttatagc agatccgttc ctaaagggtt ctacaatgta cagaaccggc   4260
gattatgtga aattattgcc taatggaaat attcaataca ttggacgtgt ggacaatcaa   4320
gtgaaaattc gtggattccg catcgaatta gaagccatta tgaacacatt aaaacaatgt   4380
gaatcaatca aagatgtaat tgttgttgta caagaacaga atgggtataa aacactggtt   4440
gcatatgttg tgggagaaga atcgctttca atagaaacag tgagggccta tgcaaaaaaa   4500
catttggctg aatatatggt accttctcaa tttatattta tagaagaaat tccgctctca   4560
ataaatggga aagtacagta tagtaagtta ccgaaagtac aagaagtatt gcataaaaaa   4620
gtagaaacgc tgttaccaga aaacagatta gaagaaatta ttctacgtgt gtatcgtgat   4680
gtattagaga aagaagattt tggcgtaaca gattcattct tcgcttatgg tggtgactct   4740
ttactaagta ttcaagtcgt ttcgatgttg aaaaaagagg agattgcagt agatccgaaa   4800
atgattttta tgcatacaac ggttagagag ttagcaaagg catgtgaaaa tcgtccggtt   4860
atggaagaaa caaaaaggac tgagaaggat tatttaattc aaatgcgtga aggtagtgaa   4920
gaagatagtt gtatcatttt tgctcctccg gcaggtggaa cggtacttgg atatatagaa   4980
ttagcaaggt atttcgaggg aattggcaat gtttacggcc tacaagcacc gggactgtat   5040
gacgatgaag agcctacgtt cttagattac gatgaacttg tacaagtgtt tcttcgctcg   5100
attgaaggga catatcgtcc aggtcaagat tatttaggtg gccactcctt agggggacat   5160
atcgcatttg gaatgtgctg tgaactgatt aagcaaggaa aggcaccaaa gggattgcta   5220
attctagata caacaccatc acttcaagtt gtaaaggggg ccaaggatga aaaaatagcc   5280
gaggaggact ttaaaatgat ggtactggct gccggtatcg gaaatatgat gggtgttgat   5340
ccagaagaat taaagcaact gtcgtatgaa gaagcaaaaa caagagttgt cgcagtggca   5400
caaaaggatg aaaagttaaa aacttttata aatgaaacat atttggataa gtatttgaag   5460
ttacaaattc atagtttact aatgtcacga acattagaat tggagaaaac acaattagat   5520
```

-continued

```
attccgatta aggtatttaa aacacagttt catacagaag agctagtaga aagatttgat   5580

gcttggcata actatacaaa tcaagcctgc acattcattg atataccagg cacacatacg   5640

acgatgatgc gtttaccaca tgtgaaagag gtagcgaaaa aaatagaaga acagctataa   5700
```

<210> SEQ ID NO 8
<211> LENGTH: 11115
<212> TYPE: RNA
<213> ORGANISM: Bacillus cereus

<400> SEQUENCE: 8

```
uuuauaaaau caaugaauca guugggaaaa ucaaaaaauu uacauaaugg ggggaugaug     60

gagaugaaac gaguggaaga acaugaucac auucaugugu uaaaugaaau agaaaacgaa    120

ugcgaaagaa gauaugggag aaguaauauu gcaauuaugc uugaaaagca ugguguucau    180

gaacagccgc uucauauaga agacuuauuu caugagguag agaugcaaga acauucacga    240

guaucgcgcc acgaaacagu uuugaugaca gauaaacaau guauagauga gaguggaaaa    300

ccguuagcuc uucguuuugg ugagccacuu caucuugaug acuguacccc aaaaacacua    360

caagaaauuu uaaagcgugc cgcuaagcaa gcaaaagaua aagggaugac auuuguauau    420

gaagauggac augaagagua ccucuccuac caagagaugu uggcagaugc ggagcgguua    480

cuaaaagggu ugcgaaaucu ugguauacaa ccaggagaaa guauuuuguu ucaauuuaag    540

gacaauaagc auuuuguuac ugcguuuugg gcauguauac uuggggggauu uuuaccaacg    600

ccguuaggaa cggccccuau cuauagugag caaaaugcac aaguauuaaa acuuuauaac    660

acauggcagc uauuagaaca accgauuauu uuaacggaau uugaauugaa agaagagauu    720

gcugcaauuc gaacaacauu gcaacgucaa gagauuguua uacauaguau ugagaauguu    780

auggauacag cgcgcgauac aaacugguuu ccuuguaccg aagauacuau uguuuugaau    840

uuauuaacgu cugguagcac aggaguaccc aaaugugugc agcacaaaag uaaauccauu    900

auugcgcgca caguuuccaa uuguauugac cgccagcuag augaaaaaga aguaucguua    960

aauuggaugc cgcuugauca uguuggaggc aucguaaugu gucacauucg ugauaccuau   1020

uuaaugugcc aacagguaaa cugucuuauu ucggcauuua uugaaaaucc gcuaaauugg   1080

uugcacugga uugaugcuua cucagcgaca uuuacauggg cgccaaacuu cgcuuuuuca   1140

uuaauuaacc aguaugaaga agagauuaaa ucaucuucau ggaaucuuuc uucgaugaga   1200

uacaucguaa augguggga agcuguuauu ucaaguguug ggaugaaauu uuuacaauug   1260

uuacagcaac aucaauugcc uucgaacugu cuuauuccua cguuugggau gucugaaguu   1320

ucuucgggua uuauugaaug ucauucguuu uauacgcaaa cgacaaauac aggaauguug   1380

uauguugaua agaauucuuu agaugguaau uuacaauuca cauaugaggg gcaccaaaau   1440

gccauuguuu uuacggaagu agggagaccg augccuggua uuggcauucg uauuguugau   1500

gaggacaauc agugccuguc agaagaucgu auuggacgau uccaaauuca ugguccaacg   1560

guuaugaaug guuauuucaa aaaugaugaa gcaaaugcgg aaaguuuuac ugaagauggc   1620

ugguucgaua guggagaucu gggguuuaua cauaacggua aucuugucau uacaggaaga   1680

aaaaaggaua ugauuguugu ucauggugca aauuacuaca acuaugaaau ugaagccuug   1740

guagaacaag uaccuggggu ggaaaccacg uuuguaugug caacgagugu gaagucggcu   1800

gaaggagcag aggaauuagc uauuuucuuu gucccaguaa uuaaucaugu uucugugaug   1860

uuugcgacga ugcaacaaau caaacaaauu guugcgcgca aaaugggguau cacgccgaaa   1920

gugauuauac caauucagaa ggaagcauuc uuuaaaacgg auagugggaa aauaacgaga   1980
```

-continued

```
aaugcauuuc aaaaacaguu ugagaacggg gcauauagag agauuacaca aaagauugau   2040
ugccauuuac aaaaugaaaa aacacuaucu caguggguuu aucgugaaaa auuagucgaa   2100
aguaaguugg gcaaaagcgu auccucccaa aaagaaacgu auguuuucuu ucgacaaggu   2160
aaaucauuuc aucauguccu aaaagaaaag uuaacgcaac auucuguugu uauuguggau   2220
guaggagaaa cauucgguga gauccaucca aaucauuauc aaauuaaucc uaaaaacaaa   2280
auggauuacg uucgauuauu ugaagaacuc gcaaaaagaa auguagaaga ucaaguuuuu   2340
caucucuugc augcuuggaa uuauugcgau acaguuccaa cuuuuagauc gguagaagau   2400
uuagcuaaug cgcaauaucu uggugugguu agugugaugu ucgcacuuca agcuauuaug   2460
caugcgaaau ugccacuacg ucguguuacg gugauugcga caaauagugu uggauuagaa   2520
gcgaaggaaa ugaacuauuc auguucaaca uuagaagguu augugaaaac uuugccagcu   2580
gaguuugaaa auuuacaagu gaaguauauu gauauagaag gaaaagauau acaguuugau   2640
acugagaccg uauggaaaga acuucagcaa caagaaacca uuccugucgu auuguaucgu   2700
gaugagaaaa gauacaaaau agguuuagaa aaaguaccaa uguuagaaca gaaagaaaaa   2760
aauauuccgu uucaacagca aggguuuuac aucauuacag guggucuugg ugguuugggg   2820
acgcuuguag ccaaauuacu uuuagaacga uacagcgcaa auguucuuuu acuuggucga   2880
acagaaauug aaacaaaugc agaaaaaaug cgccuucuug auucauuaaa agaguaugaa   2940
caauauggug guacagucca auauaaaaug ugcaauguaa uggauuuaga ugcgaugcga   3000
aaaguuguuc auucacagga agaacgucug caacaaaagg uaaaugggau uauccaccuu   3060
gcagggauua uucaagaaau acugauagaa aagcaaaccg aaaaagaacu gcaugcuaug   3120
uuugaagcua agguauaugc aucuugggug cuacaugaaa ucguaaaaga aaggcaagau   3180
ugucucuaca uuacaacuuc uucagcaaga acguuguuac cggggaugac caucucagcu   3240
uauuguagug cgaaucgauu uguugaaaau uuugcauauu aucaacgaag ucaaaaugua   3300
aauagcuacu guuuuucaug gaguuucugg aaugagauug gaaugguuac aaauuuacuu   3360
auuaaaaaug cguugauagc aaaaggauuu caauugaucg augaucaaaa agguauauau   3420
ucccuuuugg cgggauuaaa agggaacgaa ccuaauguuu uuguuggaau caaucaugaa   3480
aaagaagaaa uggcucaucu gauuggaacc gaggaacaag aaacacaaca auuaacaauc   3540
uauauuacac cagaauacuu acauauucuu gaagaagugu ucucuauacu aaauagagaa   3600
gaauuuggug gauuggagaa agagauuguc auucuaccaa aauuaccgcu ugaugaauau   3660
gguaaaguag aucaaacucg uuuggcucau gcgucggaua gccguuuugg aaagaaacaa   3720
cauaucguac caagaaauga uauagaagag aaaauugcau ucauuuggga aggucuuuug   3780
aauaaaaagg auauuagugu acuugaccau uucuucgaau uaggugguga uucuuuaaaa   3840
gcgacacaaa ugauuucugc guugaaaaag aauuuugcug uuacgauuac gcaacaggaa   3900
uuuuuucaau cgaguacagu agaagagcuu gcuaguuuag uagaaaagaa acuuucucgu   3960
acucguacgc augaaaugga cauaguuacu uuuagugacc gagguaacgu aguagagaug   4020
ucuucugcac aaaagcggca augguuuuua uaugaaaugg aucgagaaaa uccuuauuac   4080
aauaauacac uuguaauucg uuugacggga gaaauucauc uuccuauuuu aagaaguucu   4140
auuauugagu uaguaaauaa gcaugaaaca uugcgaacaa cauuugugau gguggauggu   4200
auaccaucac aaauuauugc agaugaagag uuaguugaaa uagaggaaau ugauuugaaa   4260
caccuaucug cugaggagac guugcaaaaa cuagaggguu uacgacaacg ggaagcaaau   4320
```

-continued

```
acggcguuua aaaucgaaaa uagcgcuuuu cgugcaaaag ugauuuuaau ugaugagaag   4380
agaguggaga uuuuacuuuc cgugcaucac auuguuucgg augguugguc gaugggggauu   4440
uuagugaagg acauugcgga aaucuaugaa gauauucggc aguggggaga aaguaagcaa   4500
gagccauuac cgauucaaua cgcagauuau acuuuguggc aaaaugaguu uaugaaaggu   4560
gaggaauuua gcaagcaacu gucuuauugg aaggagaaau uagcugaaga uauaccugua   4620
cuugaucuuc cguuagauaa accacggcca ccaauucaaa cauaucgugg gaagguuaag   4680
acuuucacgu uacaugaaaa caugacaagg augcuaaaag aaauauguca agaagaagaa   4740
ugcacgcucu uuauguuguu acuuucggcu uucucaucau uauuacaucg uuauacaggu   4800
caggaggauc uuguuguugg uucgcuaguu gcaaaucgaa accgugagca aaucgagaaa   4860
uugauugguu ucuuuguuaa uacguuaccg cuacguauua aucuucaucg ggaaaugcaa   4920
uuuacugaau ugcuuucgca aguaaagaaa acgaccauug augcauauga ucaucaagau   4980
gugccuuuug agcuacuagu cgaugaauua cagauugaga gagauucgag ucguaaugcg   5040
cuauuccaag uguuguuugu cuuacaaaac gcacaauuac aagcaguaga cuuagagaaa   5100
gcgacaaugg aacucgaaau uuuagauagu gacacggcca aguuugauau gucagugcaa   5160
auuuucgaau uggaggacac uuuaucuauc aaauuagagu acaauacgga uuuauuuuuu   5220
gaugauacaa uagaacgcuu ucuugcucau uaugaaacca uauuagcaag cguuauucau   5280
aaucaaaagg caaaaauagg ggaauuguca auuuuaccac aaucugaaua uacgaaacuu   5340
guaucugagu ggaaugaaaa gagugccacu uauaauggaa aucaguguau ucaugaauug   5400
uucgaagcag cuguucacaa aacgccaucu gcaacagcgc uuauuuaucg caacaaagag   5460
augacauacg aggauguuaa ugcgcaggca aaugcacuug cacauaaauu aagagaugca   5520
gguguuggac caaaccaggu aguuggcgug uuaugugauc gcucuuucga gaugguuguu   5580
gguauauuag cuguuuuaaa agcaggugga gcguauuugc caauugauac agcguacccg   5640
augcaacgaa cagaauacgu ccugcaaaau agugaggcaa cuauucucuu aacaaaggaa   5700
uguuaccuua aggagucuuu agauuuugag ggggaaguuu uuuacuuaga ugaugcaaga   5760
cuguuugaag gggauagaag agauuuacaa aauaucaaua auccuacuaa ccuugcuuau   5820
aucauuuaua caucaggauc cacgggaaau ccaaaaggug uuaugguagc gcaucaaagu   5880
guugugaauu ugcuacucga uuuacaagag aaauauccgg ugcuagcaga agauaagcac   5940
uuguuaaaaa caacauauac guuugauguu ucuguagccg aaauuuuugg augguuucau   6000
gcagguggca cacuuguuau ugcuggacau ggugaugaaa aagacccaga gaaacugauu   6060
caauugauuc aaugccacaa gguuacacau auuaacuucg uaccaucgau gcuacaugca   6120
auguuacagg ccuuggauga aaaagauuuu gcaauuauga aucgguugaa auauauuauc   6180
gucgcaggag aagcuguuuc accagaacuu uguaaucgac uguacgcuca uuguccaaau   6240
guaaaacuag aaaaucuaua ugggccaacg gaaggaacga uuuaugcgac aggguuuucu   6300
auucauaaag aaaugaaugu agcuaaugua ccgauuggaa aaccacuuuc ucauguggaa   6360
acguauauuc uugaucaaaa caaucaaauu guaccaauug guguaccagg ugaauugugu   6420
cugggaggaa uauguguagc aaaagguuau augaaagagc cgguguuaac agaagaaaaa   6480
uucgucguca auccuaugaa acaaagugaa agaauguacc gaacggguga uuugguacgc   6540
ugguuagcag augggaauau ugaauauuua ggaagaauag auaaccaagu caagauaaga   6600
ggcuuccgaa uugagcuugg ugaaauugaa gcggcaauug cugcauuaga agauguagua   6660
caaacaauug uuacaacaau gacggaucau aaaggugcga acaagauugu cgcauauguu   6720
```

-continued

```
gugagcgaaa aguaugauga agaacgaauu cgugaacaug ugaaaaagac guugccgcaa   6780
uauaugguac caaguuauuu cguuucgaug aaggcauugc cucuuaauaa aaauggaaaa   6840
guugaucgca aacaguugca uucgguugau cuuuaugaaa cgaguaugga uacagucauu   6900
gugggaccaa gaaacgaaaa agaagcaaug cuuucgguua uuuggcaaga gcuuuuggga   6960
uuagagaaua ucaguguuca cgauaauuuc uuuaagcuug guggucauuc cauuaaugcg   7020
acacaauugg uaucaaaaau uuauaguguu ugccgaguga gaaugccucu uaaaaaugug   7080
uuucaguaua caacguuagc uacaauggca cggguguuag aagaguuguu gguaagcgcu   7140
guugacgaag uagcuguaac aacggagcgc auuccaaaga uacuaccgag aacauauuac   7200
gauuugucgu auucacaaca aagaauuuau uucuuaucua caauggagaa agaaaccaau   7260
uacuauaaua uucuuggugc uugggauauu uaugggaaac uagauguuac gcuauuugaa   7320
aaagcaaucc aacuauuaau gaagaaacac cauucauuac gugcaacauu ugaaaucgug   7380
gacggcaaac cugugcaaau cauccacgau gauauggaaa uuccugugca auuuauugac   7440
cuuacugu ga ugccagaagg auuacggaua gaagaaguag augaacuuau guuaaaagag   7500
ucuaaaagag uauacaaucu cgcaaauggu ccguuaaugc auuguacaau uguuaagaua   7560
aaagaaggug agcauguauu auugauugga caacaucaua ucauuaguga ugguugguca   7620
cuugguauuu uuguaaaaga guuaaaugaa auguaugaug ccuuugugca acacaaacca   7680
guugcugaaa caccaucaac aaucuccauu auggacuuua cugcuuggca caauaguaaa   7740
guagaugaag aucaagauga ucgacaauau ugguuacagc gauuugaggg agaguuaccg   7800
acguuagagu ugccgacaga cagacaacgu ccacuuuuga aaacauauca uggugacaca   7860
uuaucauaua aggugaauuc ucaauugcau caaaaauuaa aggacuuuag ucaugcaaau   7920
gguguaacga uguuuaugac gcuauuaacg gcguauaaua uuauguugaa uaaguuaaca   7980
aaugaaacag acauuguugu uggcuccccu guagcaggua gaaaugaacc agaaucaaaa   8040
gauuuaaucg ggauguuugu gaauacguua gcguuacguu cgcauuuagg agauaauccg   8100
acaguugaug ucuuauuaaa acaaauaaaa cagaauacuu uagaagcaua caaucaucaa   8160
gauuauccau uugauaaguu gguugaugac uuggauccac aucgagauuu aaguaggaca   8220
ccaauuuucc aagugaugau gggauauaug aauaugccau ugaugguugc auuucgugaa   8280
gcagagguuc gcgaacgauu uguucgacau aaagucgcaa gguuugauuu aacacuucau   8340
guguuugaag augaagauca gaugaaaaua uucuuugagu auaauacaga uuuauuugau   8400
gaaucaacga uuaugcguug gcagaaucau uucgaaacgc uauuacagga aauuguaucg   8460
aauccgacaa aacguauuuc ggaauugaau auacuuacaa augaggagaa auaugaaauu   8520
cuagagauga acaauaauuc aacggaguau ccucagcaug aaucuguugc ggagauuuuu   8580
agagaaacga agauaaagca ucaagcaaaa cuagcaauua cguacaaaga uagaaaguua   8640
acguaugcag aguugaguga aaaagcaaau gcguuggcac auacauugaa acgucgaggu   8700
guugcgcagc augauguugu uggaauuguc gcagagcguu cgccugaaac aauuauugga   8760
auacucgcaa ucuuaaaagu aggagcaauu uauuugccaa uugauccaaa acuaccgcaa   8820
uuaacacugc aacacauuug gcgagauagc ggugcaaaag uccuccuagg gaaaaaugaa   8880
acaacuguag aaguuggcaa ggaaguuccg uuuguggaca ucgaagggga uaaagggaag   8940
caagaggagu uagugugucc aauuagucca gaagauacgg cauauauuau guauacguca   9000
ggcaguacug gaaaaccaaa aggggguuaug gugacacaua gaaauauugu ucguuuagua   9060
```

```
aaaaauacga auuucguuuc uuugcaagag caagaugugu uguuacagac agguucgcuu   9120

acuuuugacg cugcaacauu ugaaauuugg ggcgcauugc uaaauggacu uacgcuucau   9180

uuaguagaag auuacguaau uuuagauggg gaggcgcuuc aggaagagau ucagcagaac   9240

aaagcaacca uuaugugggu gagugcaccg cuguuuaauc aauuggcgga ucaaaaccca   9300

gcgauguuua caggcauuaa gcaauugcuc auuggugug auguuuuauc gccaaaacau   9360

auuaacaaag ugauggacca uugugcacca aucaauauca uuaauggaua cgguccaaca   9420

gaaaauacga cguucucgac gucauuugua auugaucaaa uguaucaaga cagcauuccg   9480

auuggaacac cgauugcuaa uucuagugcu uacauuuuag auguacauca aaauauacaa   9540

ccuauuggug uaguuggcga acuauguguu gguggugaug gaguugcaaa agguuaugug   9600

aaccuugaac aauuaacaga agaacgguuu auagcagauc cguuccuaaa ggguucuaca   9660

auguacagaa ccggcgauua ugugaaauua uugccuaaug gaaauauuca auacauugga   9720

cguguggaca aucaagugaa aauucgugga uuccgcaucg aauuagaagc cauuaugaac   9780

acauuaaaac aaugugaauc aaucaaagau guaauuguug uuguacaaga acagaauggg   9840

uauaaaacac ugguugcaua uguuguggga gaagaaucgc uuucaauaga aacagugagg   9900

gccuaugcaa aaaaacauuu ggcugaauau augguaccuu cucaauuuau auuuauagaa   9960

gaaauuccgc ucucaauaaa ugggaaagua caguauagua aguuaccgaa aguacaagaa  10020

guauugcaua aaaaaguaga aacgcuguua ccagaaaaca gauuagaaga aauuauucua  10080

cguguguauc gugauguauu agagaaagaa gauuuuggcg uaacagauuc auucuucgcu  10140

uaugguggug acucuuuacu aaguauucaa gucguuucga uguugaaaaa agaggagauu  10200

gcaguagauc cgaaaaugau uuuuaugcau acaacgguua gagaguuagc aaaggcaugu  10260

gaaaaucguc cgguuaugga agaaacaaaa aggacugaga aggauuauuu aauucaaaug  10320

cgugaaggua gugaagaaga uaguuguauc auuuuugcuc cuccggcagg uggaacggua  10380

cuuggauaua uagaauuagc aagguauuuc gagggaauug gcaauguuua cggccuacaa  10440

gcaccgggac uguaugacga ugaagagccu acguucuuag auuacgauga acuuguacaa  10500

guguuucuuc gcucgauuga agggacauau cguccagguc aagauuauuu agguggccac  10560

uccuuagggg gacauaucgc auuuggaaug ugcugugaac ugauuaagca aggaaaggca  10620

ccaaagggau ugcuaauucu agauacaaca ccaucacuuc aaguuguaaa gggggccaag  10680

gaugaaaaaa uagccgagga ggacuuuaaa augaugguac uggcugccgg uaucggaaau  10740

augaugggug uugauccaga agaauuaaag caacugucgu augaagaagc aaaaacaaga  10800

guugucgcag uggcacaaaa ggaugaaaag uuaaaaacuu uuauaaauga aacauauuug  10860

gauaaguauu ugaaguuaca aauucauagu uuacuaaugu cacgaacauu agaauuggag  10920

aaaacacaau uagauauucc gauuaaggua uuuaaaacac aguuucauac agaagagcua  10980

guagaaagau uugaugcuug gcauaacuau acaaaucaag ccugcacauu cauugauaua  11040

ccaggcacac auacgacgau gaugcguuua ccacauguga aagagguagc gaaaaaaaua  11100

gaagaacagc uauaa                                                   11115
```

<210> SEQ ID NO 9
<211> LENGTH: 5700
<212> TYPE: RNA
<213> ORGANISM: Bacillus cereus

<400> SEQUENCE: 9

```
cacaaaacgc caucugcaac agcgcuuauu uaucgcaaca aagagaugac auacgaggau     60
```

-continued

```
guuaaugcgc aggcaaaugc acuugcacau aaauuaagag augcaggugu uggaccaaac    120
cagguaguug gcguguuaug ugaucgcucu uucgagaugg uuguugguau auuagcuguu    180
uuaaaagcag guggugcgua uuugccaauu gauacagcgu acccgaugca acgaacagaa    240
uacguccugc aaaauaguga ggcaacuauu cucuuaacaa aggaauguua ccuuaaggag    300
ucuuuagauu uugaggggga aguuuuuuac uuagaugaug caagacuguu ugaaggggau    360
agaagagauu uacaaaauau caauaauccu acuaaccuug cuuauaucau uuauacauca    420
ggauccacgg gaaauccaaa agguguuaug guagcgcauc aaaguguugu gaauuugcua    480
cucgauuuac aagagaaaua uccggugcua gcagaagaua agcacuuguu aaaaacaaca    540
uauacguuug auguuucugu agccgaaauu uuuggauggu uucaugcagg uggcacacuu    600
guuauugcug gacauggugua ugaaaaagac ccagagaaac ugauucaauu gauucaaugc    660
cacaagguua cacauauuaa cuucguacca ucgaugcuac augcaauguu acaggccuug    720
gaugaaaaag auuuugcaau uaugaaucgg uugaaauaua uuaucgucgc aggagaagcu    780
guuucaccag aacuuuguaa ucgacuguac gcucauuguc caaauguaaa acuagaaaau    840
cuauaugggc caacggaagg aacgauuuau gcgacagggu uucuauucaa uaaagaaaug    900
aauguagcua auguaccgau uggaaaacca cuuucucaug uggaaacgua uauucuugau    960
caaaacaauc aaauuguacc aauuggugua ccaggugaau ugugucuggg aggaauaugu   1020
guagcaaaag guuauaugaa agagccggug uuaacagaag aaaaauucgu cgucaauccu   1080
augaaacaaa gugaaagaau guaccgaacg ggugauuugg uacgcugguu agcagauggg   1140
aauauugaau auuuaggaag aauagauaac caagucaaga uaagaggcuu ccgaauugag   1200
cuuggugaaa uugaagcggc aauugcugca uuagaagaug uaguacaaac aauuguuaca   1260
acaaugacgg aucauaaagg ugcgaacaag auugucgcau auguugugag cgaaaaguau   1320
gaugaagaac gaauucguga acaugugaaa aagacguugc cgcaauauau gguaccaagu   1380
uauuucguuu cgaugaaggc auugccucuu aauaaaaaug gaaaaguuga ucgcaaacag   1440
uugcauucgg uugaucuuua ugaaacgagu auggauacag ucauuguggg accaagaaac   1500
gaaaaagaag caaugcuuuc gguuauuugg caagagcuuu ugggauuaga gaauaucagu   1560
guucacgaua auuucuuuaa gcuugguggu cauuccauua augcgacaca auugguauca   1620
aaaauuuaua guguuugccg agugagaaug ccucuuaaaa auguguuuca guauacaacg   1680
uuagcuacaa uggcacgggu guuagaagag uuguugguaa gcgcuguuga cgaaguagcu   1740
guaacaacgg agcgcauucc aaagauacua ccgagaacau auuacgauuu gucguauuca   1800
caacaaagaa uuuauuucuu aucuacaaug gagaaagaaa ccaauuacua uaauauucuu   1860
ggugcuuggg auauuuaugg gaaacuagau guuacgcuau uugaaaaagc aauccaacua   1920
uuaaugaaga aacaccauuc auuacgugca acauuugaaa ucguggacgg caaaccugug   1980
caaaucaucc acgaugauau ggaaauuccu gugcaauuua uugaccuuac ugugaugcca   2040
gaaggauuac ggauagaaga aguagaugaa cuuauguuaa aagagucuaa aagaguauac   2100
aaucucgcaa augguccguu aaugcauugu acaauuguua agauaaaaga aggugagcau   2160
guauuauuga uuggacaaca ucauaucauu agugaugguu ggucacuugg uauuuuugua   2220
aaagaguuaa augaaaugua ugaugccuuu gugcaacaca aaccaguugc ugaaacacca   2280
ucaacaaucu ccauuaugga cuuuacugcu uggcacaaua guaaaguaga ugaagaucaa   2340
gaugaucgac aauauugguu acagcgauuu gagggagagu uaccgacguu agaguugccg   2400
```

-continued

```
acagacagac aacguccacu uuugaaaaca uaucauggug acacauuauc auauaaggug   2460
aauucucaau ugcaucaaaa auuaaaggac uuuagucaug caaaugguguu aacgauguuu   2520
augacgcuau uaacggcgua uaauauuaug uugaauaagu uaacaaauga aacagacauu   2580
guuguuggcu ccccuguagc agguagaaau gaaccagaau caaaagauuu aaucgggaug   2640
uuugugaaua cguuagcguu acguucgcau uuaggagaua auccgacagu ugaugucuua   2700
uuaaaacaaa uaaaacagaa uacuuuagaa gcauacaauc aucaagauua uccauuugau   2760
aaguugguug augacuugga uccacaucga gauuuaagua ggacaccaau uuuccaagug   2820
augaugggau auaugaauau gccauugaug guugcauuuc gugaagcaga gguucgcgaa   2880
cgauuuguuc gacauaaagu cgcaagguuu gauuuaacac uucauguguu ugaagaugaa   2940
gaucagauga aaauauucuu ugaguauaau acagauuuau uugaugaauc aacgauuaug   3000
cguuggcaga aucauuucga aacgcuauua caggaaauug uaucgaaucc gacaaaacgu   3060
auuucggaau ugaauauacu uacaaaugag gagaaauaug aaauucuaga gaugaacaau   3120
aauucaacgg aguauccuca gcaugaaucu guugcggaga uuuuuagaga aacgaagaua   3180
aagcaucaag caaaacuagc aauuacguac aaagauagaa aguuaacgua ugcagaguug   3240
agugaaaaag caaaugcguu ggcacauaca uugaaacguc gagguguugc gcagcaugau   3300
guuguuggaa uugucgcaga gcguucgccu gaaacaauua uuggaauacu cgcaaucuua   3360
aaaguaggag caauuuauuu gccaauugau ccaaaacuac cgcaauuaac acugcaacac   3420
auuuggcgag auagcggugc aaaaguccuc cuagggaaaa augaaacaac uguagaaguu   3480
ggcaaggaag uuccguuugu ggacaucgaa ggggauaaag ggaagcaaga ggaguuagug   3540
uguccaauua guccagaaga uacggcauau auuauguaua cgucaggcag uacuggaaaa   3600
ccaaaagggg uuauggugac acauagaaau auuguucguu uaguaaaaaa uacgaauuuc   3660
guuucuuugc aagagcaaga uguguuguua cagacagguu cgcuuacuuu ugacgcugca   3720
acauuugaaa uuuggggcgc auugcuaaau ggacuuacgc uucauuuagu agaagauuac   3780
guaauuuuag auggggaggc gcuucaggaa gagauucagc agaacaaagc aaccauuaug   3840
ugggugagug caccgcuguu uaaucaauug gcggaucaaa acccagcgau guuuacaggc   3900
auuaagcaau ugcucauugg uggugauguu uuaucgccaa aacauauuaa caaagugaug   3960
gaccauugug caccaaucaa uaucauuaau ggauacgguc caacagaaaa uacgacguuc   4020
ucgacgucau uuguaauuga ucaaauguau caagacagca uuccgauugg aacaccgauu   4080
gcuaauucua gugcuuacau uuuagaugua caucaaaaua uacaaccuau uggguguaguu   4140
ggcgaacuau guguuggugg ugauggaguu gcaaaagguu augugaaccu ugaacaauua   4200
acagaagaac gguuuauagc agauccguuc cuaaaggguu cuacaaugua cagaaccggc   4260
gauuauguga aauuauugcc uaauggaaau auucaauaca uuggacgugu ggacaaucaa   4320
gugaaaauuc guggauuccg caucgaauua gaagccauua ugaacacauu aaaacaaugu   4380
gaaucaauca aagauguaau uguuguugua caagaacaga augguauaa aacacugguu   4440
gcauauguug ugggagaaga aucgcuuuca auagaaacag ugagggccua ugcaaaaaaa   4500
cauuuggcug aauauauggu accuucucaa uuuauauuua uagaagaaau uccgcucuca   4560
auaaaauggga aaguacagua uaguaaguua ccgaaaguac aagaaguauu gcauaaaaaa   4620
guagaaacgc uguuaccaga aaacagauua gaagaaauua uucuacgugu guaucgugau   4680
guauuagaga aagaagauuu uggcguaaca gauucauucu ucgcuuaugg uggugacucu   4740
uuacuaagua uucaagucgu uucgauguug aaaaaagagg agauugcagu agauccgaaa   4800
```

```
augauuuuua ugcauacaac gguuagagag uuagcaaagg caugugaaaa ucguccgguu   4860

auggaagaaa caaaaaggac ugagaaggau uauuuaauuc aaaugcguga agguagugaa   4920

gaagauaguu guaucauuuu ugcuccuccg gcagguggaa cgguacuugg auauauagaa   4980

uuagcaaggu auuucgaggg aauuggcaau guuuacggcc uacaagcacc gggacuguau   5040

gacgaugaag agccuacguu cuuagauuac gaugaacuug uacaaguguu ucuucgcucg   5100

auugaaggga cauaucgucc aggucaagau uauuuaggug gccacuccuu agggggacau   5160

aucgcauuug gaaugugcug ugaacugauu aagcaaggaa aggcaccaaa gggauugcua   5220

auucuagaua caacaccauc acuucaaguu guaaaggggg ccaaggauga aaaaauagcc   5280

gaggaggacu uuaaaaugau gguacuggcu gccgguaucg gaaauaugau ggguguugau   5340

ccagaagaau uaaagcaacu gucguaugaa gaagcaaaaa caagaguugu cgcaguggca   5400

caaaaggaug aaaaguuaaa aacuuuuaua aaugaaacau auuuggauaa guauuugaag   5460

uuacaaauuc auaguuuacu aaugucacga acauuagaau uggagaaaac acaauuagau   5520

auuccgauua agguauuuaa aacacaguuu cauacagaag agcuaguaga aagauuugau   5580

gcuuggcaua acuauacaaa ucaagccugc acauucauug auauaccagg cacacauacg   5640

acgaugaugc guuuaccaca ugugaaagag guagcgaaaa aaauagaaga acagcuauaa   5700
```

```
<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:PCR primer
      for amplifying a DNA fragment unique to a cereulide synthetase
      gene

<400> SEQUENCE: 10

ggtgaattgt gtctgggagg                                              20


<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:PCR primer
      for amplifying a DNA fragment unique to a cereulide synthetase
      gene

<400> SEQUENCE: 11

atttttatta agaggcaatg                                              20


<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:PCR primer
      for amplifying a DNA fragment unique to a cereulide synthetase
      gene

<400> SEQUENCE: 12

gtcaagataa gaggcttccg aatt                                         24


<210> SEQ ID NO 13
<211> LENGTH: 20
<212> TYPE: DNA
<213> ORGANISM: Artificial Sequence
<220> FEATURE:
```

```
<223> OTHER INFORMATION: Description of Artificial Sequence:PCR primer
      for amplifying a DNA fragment unique to a cereulide synthetase
      gene

<400> SEQUENCE: 13

aatggaatga ccaccaagct                                                 20


<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:PCR primer
      for amplifying a DNA fragment unique to a cereulide synthetase
      gene

<400> SEQUENCE: 14

aggaagttcc gtttgtggac                                                 20


<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:PCR primer
      for amplifying a DNA fragment unique to a cereulide synthetase
      gene

<400> SEQUENCE: 15

cacataacct tttgcaactc                                                 20


<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:PCR primer
      for amplifying a DNA fragment unique to a cereulide synthetase
      gene

<400> SEQUENCE: 16

ggcgaactat gtgttggtgg                                                 20


<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:PCR primer
      for amplifying a DNA fragment unique to a cereulide synthetase
      gene

<400> SEQUENCE: 17

taaagagtca ccaccataag                                                 20


<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:PCR primer
      for amplifying a DNA fragment unique to a cereulide synthetase
      gene

<400> SEQUENCE: 18

acgtcaggca gtactggaaa                                                 20
```

-continued

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence : PCR prime r for amplifying aDNA fragment unique to a cereulide synthetase gene

<400> SEQUENCE: 19
ttcgatgcgg aatccacgaa 20

<210> SEQ ID NO 20
<211> LENGTH: 43
<212> TYPE: DNA
<213> ORGANISM: Artificial Sequence
<220> FEATURE:
<223> OTHER INFORMATION: Description of Artificial Sequence : PCR primer for amplifying a DNA fragment unique to a cereulide synthetase gene
<220> FEATURE:
<221> NAME/KEY: modified_base
<222> LOCATION: (14)..(14)
<223> OTHER INFORMATION: I
<220> FEATURE:
<221> NAME/KEY: modified_base
<222> LOCATION: (17)..(17)
<223> OTHER INFORMATION: I
<220> FEATURE:
<221> NAME/KEY: modified_base
<222> LOCATION: (26)..(26)
<223> OTHER INFORMATION: I

<400> SEQUENCE: 20
ggaattcctt aaaagcagga ggagcatatg tgccgcttga tcc 43

<210> SEQ ID NO 21
<211> LENGTH: 41
<212> TYPE: DNA
<213> ORGANISM: Artificial Sequence
<220> FEATURE:
<223> OTHER INFORMATION: Description of Artificial Sequence:PCR primer for amplifying a DNA fragment unique to a cereulide synthetase gene
<220> FEATURE:
<221> NAME/KEY: modified_base
<222> LOCATION: (12)..(12)
<223> OTHER INFORMATION: I
<220> FEATURE:
<221> NAME/KEY: modified_base
<222> LOCATION: (15)..(15)
<223> OTHER INFORMATION: I
<220> FEATURE:
<221> NAME/KEY: modified_base
<222> LOCATION: (18)..(18)
<223> OTHER INFORMATION: I
<220> FEATURE:
<221> NAME/KEY: modified_base
<222> LOCATION: (21)..(21)
<223> OTHER INFORMATION: I
<220> FEATURE:
<221> NAME/KEY: modified_base
<222> LOCATION: (27)..(27)
<223> OTHER INFORMATION: I
<220> FEATURE:
<221> NAME/KEY: modified_base
<222> LOCATION: (30)..(30)
<223> OTHER INFORMATION: I
<220> FEATURE:
<221> NAME/KEY: modified_base -continued

```
<222> LOCATION: (33)..(33)
<223> OTHER INFORMATION: I

<400> SEQUENCE: 21

ggaattcctt taggattacc agttgtacca gaagtgtaaa t                    41
```